United States Patent
Poddar et al.

(10) Patent No.: US 11,541,065 B2
(45) Date of Patent: Jan. 3, 2023

(54) COMPOSITIONS AND METHODS FOR TREATING BRAIN INJURY

(71) Applicants: UNM RAINFOREST INNOVATIONS, Albuquerque, NM (US); Ranjana Poddar, Albuquerque, NM (US); Surojit Paul, Albuquerque, NM (US)

(72) Inventors: Ranjana Poddar, Albuquerque, NM (US); Surojit Paul, Albuquerque, NM (US)

( * ) Notice: Subject to any disclaimer, the term of this patent is extended or adjusted under 35 U.S.C. 154(b) by 0 days.

(21) Appl. No.: 16/973,825

(22) PCT Filed: Jul. 8, 2019

(86) PCT No.: PCT/US2019/040769
§ 371 (c)(1),
(2) Date: Dec. 10, 2020

(87) PCT Pub. No.: WO2020/014102
PCT Pub. Date: Jan. 16, 2020

(65) Prior Publication Data
US 2021/0252026 A1      Aug. 19, 2021

Related U.S. Application Data

(60) Provisional application No. 62/695,346, filed on Jul. 9, 2018.

(51) Int. Cl.
| | | |
|---|---|---|
| A61K 31/675 | (2006.01) | |
| A61P 9/10 | (2006.01) | |
| A61K 31/18 | (2006.01) | |
| A61K 31/415 | (2006.01) | |
| A61K 31/497 | (2006.01) | |
| A61P 7/00 | (2006.01) | |

(52) U.S. Cl.
CPC ............ *A61K 31/675* (2013.01); *A61K 31/18* (2013.01); *A61K 31/415* (2013.01); *A61K 31/497* (2013.01); *A61P 7/00* (2018.01); *A61P 9/10* (2018.01)

(58) Field of Classification Search
CPC .. A61K 31/675; A61K 31/497; A61K 31/415; A61K 31/18; A61P 9/10; A61P 25/00
See application file for complete search history.

(56) References Cited

U.S. PATENT DOCUMENTS

2010/0048653 A1*   2/2010   Wang .................... A61P 9/00
                                                              514/561

FOREIGN PATENT DOCUMENTS

WO      2020/014102      1/2020

OTHER PUBLICATIONS

Auberson et al., "5-Phosphonomethylquinoxalinediones as competitive NMDA receptor antagonists with a preference for the human 1A/2A, rather than 1A/2B receptor composition", 2002, Bioorganic & Medicinal Chemistry Letters, vol. 12, Issue 7, pp. 1099-1102. (doi.org/10.1016/S0960-894X(02)00074-4). (Year: 2002).*
Romero-Hernandez et al., "Novel Mode of Antagonist Binding in NMDA Receptors Revealed by the Crystal Structure of the GluN1-GluN2A Ligand-Binding Domain Complexed to NVP-AAM077", 2017, Molecular Pharmacology, vol. 92, Issue 1, pp. 22-29. (doi.org/10.1124/mol.116.107912). (Year: 2017).*
Zhou et al, "Involvement of the GluN2A and GluN2B Subunits in Synaptic and Extrasynaptic N-methyl-o-aspartate Receptor Function and Neuronal Excitotoxicity", 2013, The Journal of Biological Chemistry, vol. 288, No. 33, pp. 24151-24159. (DOI 10.1 074/jbc. MI 13.482000) (Year: 2013).*
Wyllie et al., "Influence of GluN2 subunit identity on NMDA receptor function", 2013, Neuropharmacology, 74, pp. 4-17. (dx.doi.org/10.1016/j.neuropharm.2013.0I.016) (Year: 2013).*
Sun et al., "Identifying the Role of GluN2A in Cerebral Ischemia", 2017, Frontiers in Molecular Neuroscience, vol. 10, Article 12, pp. 1-4. (doi: 10.3389/fnmol.2017.00012) (Year: 2017).*
Jindal et al., "Hyperhomocysteinemia leads to exacerbation of ischemic brain damage: Role of GluN2A NMDA receptors", 2019, Neurobiology of Disease, 127, pp. 287-302. (doi.org/10.1016/j.nbd.2019.03.012) (Year: 2019).*
International Search Report and Written Opinion for PCT/US2019/040769, dated Oct. 24, 2019. 9 pages.
International Preliminary Report on Patentability for PCT/US2019/040769, dated Jan. 21, 2021. 7 pages.
Poddar, Ranjana, "Molecular basis of hyperhomocysteinemia induced brain injury in ischemic stroke," Grant Abstract, Grant No. NS083914 [online]. National Institutes of Health, project dates May 1, 2014 to Apr. 30, 2019 [retrieved on Mar. 19, 2022]. Retrieved from the Internet: URL: reporter.nih.gov/search/WisFhNW88EGFttUaVEMAfA/project-details/8757399; 4 pgs.
Paul, Surojit, "Role of Brain Specific Tyrosne Phosphatase STEP in Neuroprotection and Death," Grant Abstract, Grant No. NS059962 [online]. National Institutes of Health, project dates Apr. 1, 2008 to Mar. 31, 2024 [retrieved on Mar. 19, 2022]. Retrieved from the Internet: URL: reporter.nih.gov/search/ihrj8geFp0iohsFVejS4mw/project-details/9963368; 4 pgs.
Ansari et al., Hyperhomocysteinemia and neurologic disorders: a review. J Clin Neurol 10, 281-288 (2014).
Arundine et al., Molecular mechanisms of calcium-dependent neurodegeneration in excitotoxicity. Cell Calcium 34, 325-337 (2003).
Auberson et al., 5-Phosphonomethylquinoxalinediones as competitive NMDA receptor antagonists with a preference for the human 1A/2A, rather than 1A/2B receptor composition.

(Continued)

*Primary Examiner* — My-Chau T. Tran
(74) *Attorney, Agent, or Firm* — Mueting Raasch Group

(57) ABSTRACT

A method for treating a hyperhomocysteinemic subject having cerebral ischemic stroke generally includes administering to the hyperhomocysteinemic subject, following cerebral stroke, a composition that includes an inhibitor or an antagonist of a GluN2A-containing N-methyl-D-aspartate receptor (NMDAR) in an amount effective to ameliorate at least one symptom or clinical sign of cerebral stroke.

8 Claims, 45 Drawing Sheets

(56) References Cited

OTHER PUBLICATIONS

Austin et al., Role of hyperhomocysteinemia in endothelial dysfunction and atherothrombotic disease. Cell Death Differ 11 Suppl 1, S56-64 (2004).
Balkaya et al., Assessing post-stroke behavior in mouse models of focal ischemia. J Cereb Blood Flow Metab 33, 330-338 (2013).
Bartlett et al., Induction of cyclooxygenase-2 expression in human myometrial smooth muscle cells by interleukin-1 beta: involvement of p38 mitogen-activated protein kinase. J Physiol 520 Pt 2, 399-406 (1999).
Bazan et al., Prostaglandins and other lipid mediators in Alzheimer's disease. Prostaglandins Other Lipid Mediat 68-69, 197-210 (2002).
Bazan et al., Hypoxia signaling to genes: significance in Alzheimer's disease. Mol Neurobiol 26, 283-298 (2002).
Bonventre, Roles of phospholipases A2 in brain cell and tissue injury associated with ischemia and excitotoxicity. J Lipid Mediat Cell Signal 14, 15-23 (1996).
Bouet et al., The adhesive removal test: a sensitive method to assess sensorimotor deficits in mice. Nat Protoc 4, 1560-1564 (2009).
Bouet et al., Sensorimotor and cognitive deficits after transient middle cerebral artery occlusion in the mouse. Exp Neurol 203, 555-567 (2007).
Breder et al., Characterization of inducible cyclooxygenase in rat brain. J Comp Neurol 355, 296-315 (1995).
Brigman et al., Impaired discrimination learning in mice lacking the NMDA receptor NR2A subunit. Learn Mem 15, 50-54 (2008).
Candelario-Jalil et al., Wide therapeutic time window for nimesulide neuroprotection in a model of transient focal cerebral ischemia in the rat. Brain Res 1007, 98-108 (2004).
Candelario-Jalil et al., Post-ischaemic treatment with the cyclooxygenase-2 inhibitor nimesulide reduces blood-brain barrier disruption and leukocyte infiltration following transient focal cerebral ischaemia in rats. J Neurochem 100, 1108-1120 (2007).
Chaperon et al., Substitution for PCP, disruption of prepulse inhibition and hyperactivity induced by N-methyl-D-aspartate receptor antagonists: preferential involvement of the NR2B rather than NR2A subunit. Behav Pharmacol 14, 477-487 (2003).
Chen et al., Cyclooxygenase-2 regulates prostaglandin E2 signaling in hippocampal long-term synaptic plasticity. J Neurophysiol 87, 2851-2857 (2002).
Chen et al., Intraperitoneal infusion of homocysteine increases intimal hyperplasia in balloon-injured rat carotid arteries. Atherosclerosis 160, 103-114 (2002).
Chen et al., Differential roles of NMDA receptor subtypes in ischemic neuronal cell death and ischemic tolerance. Stroke 39, 3042-3048 (2008).
Cheng et al., Emergence of excitotoxicity in cultured forebrain neurons coincides with larger glutamate-stimulated [Ca (2)+)](i) increases and NMDA receptor mRNA levels. Brain Res 849, 97-108 (1999).
Chin et al., The global burden of neurologic diseases. Neurology 83, 349-351 (2014).
Christie et al., Enhanced hippocampal long-term potentiation in rats after chronic exposure to homocysteine. Neurosci Lett 373, 119-124 (2005).
Clemens et al., Reactive glia express cytosolic phospholipase A2 after transient global forebrain ischemia in the rat. Stroke 27, 527-535 (1996).
Colucci-D'Amato et al., Chronic activation of ERK and neurodegenerative diseases. Bioessays 25, 1085-1095 (2003).
Connor et al., Sustained dendritic gradients of Ca2+ induced by excitatory amino acids in CA1 hippocampal neurons. Science 240, 649-653 (1988).
Da Cunha et al., Chronic hyperhomocysteinemia increases inflammatory markers in hippocampus and serum of rats. Neurochem Res 37, 1660-1669 (2012).
Da Cunha et al., Increased inflammatory markers in brain and blood of rats subjected to acute homocysteine administration Metab Brain Dis 25, 199-206 (2010).
Dalton et al., NMDA GluN2A and GluN2B receptors play separate roles in the induction of LTP and LTD in the amygdala and in the acquisition and extinction of conditioned fear. Neuropharmacology 62, 797-806 (2012).
Daxhelet et al., Spectrofluorometry of dyes with DNAs of different base composition and conformation. Anal Biochem 179, 401-403 (1989).
Dayal et al., Cerebral vascular dysfunction mediated by superoxide in hyperhomocysteinemic mice. Stroke 35, 1957-1962 (2004).
Dayal et al., Murine models of hyperhomocysteinemia and their vascular phenotypes. Arterioscler Thromb Vasc Biol 28, 1596-1605 (2008).
De Erausquin et al., Gangliosides normalize distorted single-cell intracellular free Ca2+ dynamics after toxic doses of glutamate in cerebellar granule cells. Proc Natl Acad Sci U S A 87, 8017-8021 (1990).
Dean et al., p38 mitogen-activated protein kinase regulates cyclooxygenase-2 mRNA stability and transcription in lipopolysaccharide-treated human monocytes. J Biol Chem 274, 264-269 (1999).
Deb et al., Neuroprotective role of a brain-enriched tyrosine phosphatase, STEP, in focal cerebral ischemia. J Neurosci 33, 17814-17826 (2013).
Deep et al., GluN2A-NMDA receptor-mediated sustained Ca(2+) influx leads to homocysteine-induced neuronal cell death. J Biol Chem 294, 11154-11165 (2019).
Deridder et al., Traumatic mechanical injury to the hippocampus in vitro causes regional caspase-3 and calpain activation that is influenced by NMDA receptor subunit composition. Neurobiol Dis 22, 165-176 (2006).
Dewil et al., Microglia in amyotrophic lateral sclerosis. Acta Neurol Belg 107, 63-70 (2007).
Dingledine et al., The glutamate receptor ion channels. Pharmacol Rev 51, 7-61 (1999).
Duan et al., Dietary folate deficiency and elevated homocysteine levels endanger dopaminergic neurons in models of Parkinson's disease. J Neurochem 80, 101-110 (2002).
Dunham et al., A note on a simple apparatus for detecting neurological deficit in rats and mice. J Am Pharm Assoc Am Pharm Assoc 46, 208-209 (1957).
Edman et al., TCN 201 selectively blocks GluN2A-containing NMDARs in a GluN1 co-agonist dependent but non-competitive manner. Neuropharmacology 63, 441-449 (2012).
Endres et al., Folate deficiency increases postischemic brain injury. Stroke 36, 321-325 (2005).
Farooqui et al., Involvement of phospholipase A2 in neurodegeneration. Neurochem Int 30, 517-522 (1997).
Farooqui et al., Phospholipase A2 and its role in brain tissue. J Neurochem 69, 889-901 (1997).
Fischer et al., Ro 25-6981, a highly potent and selective blocker of N-methyl-D-aspartate receptors containing the NR2B subunit. Characterization in vitro. J Pharmacol Exp Ther 283, 1285-1292 (1997).
Rall et al., Intrahippocampal infusion of a cyclooxygenase-2 inhibitor attenuates memory acquisition in rats. Brain Res 968, 273-276 (2003).
Ramos et al., Low folate status is associated with impaired cognitive function and dementia in the Sacramento Area Latino Study on Aging Am J Clin Nutr 82, 1346-1352 (2005).
Randall et al., Glutamate-induced calcium transient triggers delayed calcium overload and neurotoxicity in rat hippocampal neurons J Neurosci 12, 1882-1895 (1992).
Refsum et al., Homocysteine and cardiovascular disease. Annu Rev Med 49, 31-62 (1998).
Riccio et al., What a privilege to reside at the synapse: NMDA receptor signaling to CREB. Nat Neurosci 5, 389-390 (2002).
Ricciotti et al., Prostaglandins and inflammation. Arterioscler Thromb Vasc Biol 31, 986-1000 (2011).
Ridley et al., A p38 MAP kinase inhibitor regulates stability of interieukin-1-induced cyclooxygenase-2 mRNA. FEBS Lett 439, 75-80 (1998).

(56) References Cited

OTHER PUBLICATIONS

Robles et al., Hyperhomocysteinemia in patients with mild chronic renal failure. Eur J Intern Med 16, 334-338 (2005).
Rockwell et al., A cyclooxygenase metabolite of anandamide causes inhibition of interieukin-2 secretion in murine splenocytes. J Pharmacol Exp Ther 311, 683-690 (2004).
Rogers et al., Neuroinflammation in Alzheimer's disease and Parkinson's disease: are microglia pathogenic in either iisorder? Int Rev Neurobiol 82, 235-246 (2007).
Rose et al., Inflammatory cell expression of cyclooxygenase-2 in the multiple sclerosis lesion. J Neuroimmunol 149, 40-49 (2004).
Sakimura et al., Reduced hippocampal LTP and spatial learning in mice lacking NMDA receptor epsilon 1 subunit. Nature 373, 151-155 (1995).
Sapirstein et al., Phospholipases A2 in ischemic and toxic brain injury. Neurochem Res 25, 745-753 (2000).
Schaar et al., Functional assessments in the rodent stroke model. Exp Transl Stroke Med 2, 13 (2010).
Schaefer et al., Diffusion-weighted MR imaging of the brain. Radiology 217, 331-345 (2000).
Scherer et al., Mild hyperhomocysteinemia increases brain acetylcholinesterase and proinflammatory cytokine levels in different tissues Mol Neurobiol 50, 589-596 (2014).
Schonbeck et al., Augmented expression of cyclooxygenase-2 in human atherosclerotic lesions. Am J Pathol 155, 1281-1291 (1999).
Scimemi et al., NR2B-containing receptors mediate cross talk among hippocampal synapses. J Neurosci 24, 4767-4777 (2004).
Seibert et al., Mediation of inflammation by cyclooxygenase-2. Agents Actions Suppl 46, 41-50 (1995).
Seibert et al., Distribution of COX-1 and COX-2 in normal and inflamed tissues. Adv Exp Med Biol 400A, 167-170 (1997).
Selhub et al., Association between plasma homocysteine concentrations and extracranial carotid-artery stenosis. N Engl J Med 332,286-291 (1995).
Selhub et al., Serum total homocysteine concentrations in the third National Health and Nutrition Examination Survey (1991-1994): population reference ranges and contribution of vitamin status to high serum concentrations. Ann Intern Med 131, 331-339 (1999).
Seshadri et al., Plasma homocysteine as a risk factor for dementia and Alzheimer's disease. N Engl J Med 346, 476-483 (2002).
Sharma et al., Hyperhomocysteinemia: Impact on Neurodegenerative Diseases. Basic Clin Pharmacol Toxicol 117, 287-296 (2015).
Shaw et al., Deficits in spatial learning and synaptic plasticity induced by the rapid and competitive broad-spectrum cyclooxygenase inhibitor ibuprofen are reversed by increasing endogenous brain-derived neurotrophic factor. Eur J Neurosci 17, 2438-2446 (2003).
Shen et al., The use of MRI apparent diffusion coefficient (ADC) in monitoring the development of brain infarction. BMC Med Imaging 11, 2 (2011).
Shi et al., L-homocysteine sulfinic acid and other acidic homocysteine derivatives are potent and selective metabotropic glutamate receptor agonists. J Pharmacol Exp Ther 305, 131-142 (2003).
Sibarov et al., GluN2A Subunit-Containing NMDA Receptors Are the Preferential Neuronal Targets of Homocysteine Front Cell Neurosci 10, 246 (2016).
Smith et al., Cyclooxygenases: structural, cellular, and molecular biology. Annu Rev Biochem 69, 145-182 (2000).
Sood et al., Increased apparent diffusion coefficients on MRI linked with matrix metalloproteinases and edema in white matter after bilateral carotid artery occlusion in rats. J Cereb Blood Flow Metab 29, 308-316 (2009).
Soria et al., Extrasynaptic glutamate release through cystine/glutamate antiporter contributes to ischemic damage. J Clin Invest 124, 3645-3655 (2014).
Sotak, The role of diffusion tensor imaging in the evaluation of ischemic brain injury—a review. NMR Biomed 15, 561-569 (2002).
Stephenson et al., Cytosolic phospholipase A2 (cPLA2) immunoreactivity is elevated in Alzheimer's disease brain. Neurobiol Dis 3, 51-63 (1996).
Stocca et al., Increased contribution of NR2A subunit to synaptic NMDA receptors in developing rat cortical neurons. J Physiol 507 ( Pt 1), 13-24 (1998).
Svensson et al., Spinal p38 MAP kinase is necessary for NMDA-induced spinal PGE(2) release and thermal hyperalgesia. Neuroreport 14, 1153-1157 (2003).
Swanson et al., A semiautomated method for measuring brain infarct vol. J Cereb Blood Flow Metab 10, 290-293 (1990).
Taheri et al., Partial vol. effect compensation for improved reliability of quantitative blood-brain barrier permeability. Magn Reson Imaging 25, 613-625 (2007).
Tak et al., NF-kappaB: a key role in inflammatory diseases. J Clin Invest 107, 7-11 (2001).
Takemiya et al., Roles of prostaglandin synthesis in excitotoxic brain diseases. Neurochem Int 51, 112-120 (2007).
Teather et al., Post-training cyclooxygenase-2 (COX-2) inhibition impairs memory consolidation. Learn Mem 9, 41-47 (2002).
Terasaki et al., Activation of NR2A receptors induces ischemic tolerance through CREB signaling. J Cereb Blood Flow Metab 30, 1441-1449 (2010).
Terlain et al., [Inducible cyclooxygenase. New relationships between non-steroidal anti-inflammatory agents and inhibition of synthesis of prostaglandins]. Presse Med 24, 491-496 (1995).
Tigaret et al., Subunit dependencies of N-methyl-D-aspartate (NMDA) receptor-induced alpha-amino-3-hydroxy-5-methyl-4-isoxazolepropionic acid (AMPA) receptor internalization. Mol Pharmacol 69, 1251-1259 (2006).
Tovar et al., The incorporation of NMDA receptors with a distinct subunit composition at nascent hippocampal synapses in vitro. J Neurosci 19, 4180-4188 (1999).
Tymianski, Cytosolic calcium concentrations and cell death in vitro. Adv Neurol 71, 85-105 (1996).
Tymianski et al., Normal and abnormal calcium homeostasis in neurons: a basis for the pathophysiology of traumatic and ischemic central nervous system injury. Neurosurgery 38, 1176-1195 (1996).
Ueda et al., Hippocampal gene network analysis in an experimental model of posttraumatic epilepsy. Neurochem Res 36, 1323-1328 (2011).
Ueno et al., Coupling between cyclooxygenases and terminal prostanoid synthases. Biochem Biophys Res Commun 338, 70-76 (2005).
Ungvari et al., Dysfunction of nitric oxide mediation in isolated rat arterioles with methionine diet-induced hyperhomocysteinemia. Arterioscler Thromb Vase Biol 19, 1899-1904 (1999).
Vane et al., Cyclooxygenases 1 and 2. Annu Rev Pharmacol Toxicol 38, 97-120 (1998).
Vicini et al., Functional and pharmacological differences between recombinant N-methyl-D-aspartate receptors. J Neurophysiol 79, 555-566 (1998).
Wang et al., Cdk5 activation induces hippocampal CA1 cell death by directly phosphorylating NMDA receptors. Nat Neurosci 6, 1039-1047 (2003).
Wang et al., Glutamate signaling to Ras-MAPK in striatal neurons: mechanisms for inducible gene expression and plasticity. Mol Neurobiol 29, 1-14 (2004).
Wang et al., The inflammatory response in stroke. J Neuroimmunol 184, 53-68 (2007).
Wang et al., A comprehensive analysis of gait impairment after experimental stroke and the therapeutic effect of environmental enrichment in rats. J Cereb Blood Flow Metab 28, 1936-1950 (2008).
Xiang et al., Cyclooxygenase-2 promotes amyloid plaque deposition in a mouse model of Alzheimer's disease neuropathology Gene Expr 10, 271-278 (2002).
Yagami et al., Pathophysiological Roles of Cyclooxygenases and Prostaglandins in the Central Nervous System. Mol Neurobiol 53, 4754-4771 (2016).
Yamagata et al., Expression of a mitogen-inducible cyclooxygenase in brain neurons: regulation by synaptic activity and glucocorticoids Neuron 11, 371-386 (1993).
Yang et al., Eady inhibition of MMP activity in ischemic rat brain promotes expression of tight junction proteins and angiogenesis during recovery. J Cereb Blood Flow Metab 33, 1104-1114 (2013).

(56) References Cited

OTHER PUBLICATIONS

Yenari et al., Microglial activation in stroke: therapeutic targets. Neurotherapeutics 7, 378-391 (2010).
Yu et al., BQ-869, a novel NMDA receptor antagonist, protects against excitotoxicity and attenuates cerebral ischemic injury in stroke Int J Clin Exp Pathol 8, 1213-1225 (2015).
Zhang et al., NMDA receptor-mediated activation of NADPH oxidase and glomerulosclerosis in hyperhomocysteinemic rats. Antioxid Redox Signal 13, 975-986 (2010).
Zhang et al., Decoding NMDA receptor signaling: identification of genomic programs specifying neuronal survival and death. Neuron 53, 549-562 (2007).
Zhou et al., Involvement of the GluN2A and GluN2B subunits in synaptic and extrasynaptic N-methyl-D-aspartate receptor function and neuronal excitotoxicity. J Biol Chem 288, 24151-24159 (2013).
Zhuang et al., A death-promoting role for extracellular signal-regulated kinase. J Pharmacol Exp Ther 319, 991-997 (2006).
Zieminska et al., Role of group I metabotropic glutamate receptors and NMDA receptors in homocysteine-evoked acute neurodegeneration of cultured cerebellar granule neurones. Neurochem Int 43, 481-492 (2003).
Zoccolella et al., Homocysteine levels and amyotrophic lateral sclerosis: A possible link. Amyotroph Lateral Scler 11, 140-147 (2010).
Zoccolella et al., Hyperhomocysteinemia in movement disorders: Current evidence and hypotheses. Curr Vase Pharmacol 4, 237-243 (2006).
Poddar et al., Role of AMPA receptors in homocysteine-NMDA receptor-induced crosstalk between ERK and p38 MAPK. J Neurochem 142, 560-573 (2017).
Lin et al., cPLA2 is phosphorylated and activated by MAP kinase. Cell 72, 269-278 (1993).
Lind et al., Structural basis of subunit selectivity for competitive NMDA receptor antagonists with preference for GluN2A over GluN2B subunits. Proc Natl Acad Sci U S A 114, E6942-E6951 (2017).
Lindgren et al., Plasma homocysteine in the acute and convalescent phases after stroke. Stroke 26, 795-800 (1995).
Lipton et al., Neurotoxicity associated with dual actions of homocysteine at the N-methyl-D-aspartate receptor. Proc Natl Acad Sci U S A 94, 5923-5928 (1997).
Lipton et al., Excitatory amino acids as a final common pathway for neurologic disorders. N Engl J Med 330, 613-622 (1994).
Liu et al., Role of NMDA receptor subtypes in governing the direction of hippocampal synaptic plasticity. Science 304, 1021-1024 (2004).
Liu et al., Quantitative gait analysis of long-term locomotion deficits in classical unilateral striatal intracerebral hemorrhage rat model. Behav Brain Res 257, 166-177 (2013).
Liu et al., NMDA receptor subunits have differential roles in mediating excitotoxic neuronal death both in vitro and in vivo. J Neurosci 27, 2846-2857 (2007).
Longa et al., Reversible middle cerebral artery occlusion without craniectomy in rats. Stroke 20, 84-91 (1989).
Lynch et al., Excitotoxicity: perspectives based on N-methyl-D-aspartate receptor subtypes. J Pharmacol Exp Ther 300, 717-723 (2002).
Mandrekar-Colucci et al., Microglia and inflammation in Alzheimer's disease. CNS Neurol Disord Drug Targets 9, 156-167(2010).
Mao et al., Regulation of MAPK/ERK phosphorylation via ionotropic glutamate receptors in cultured rat striatal neurons. Eur J Neurosci 19, 1207-1216 (2004).
Martel et al., The subtype of GluN2 C-terminal domain determines the response to excitotoxic insults. Neuron 74, 543-556 (2012).
Martel et al., In developing hippocampal neurons, NR2B-containing N-methyl-D-aspartate receptors (NMDARs) can mediate signaling to neuronal survival and synaptic potentiation, as well as neuronal death. Neuroscience 158, 334-343 (2009).
Martin et al., Blocking the deadly effects of the NMDA receptor in stroke. Cell 140, 174-176 (2010).
Massey et al., Differential roles of NR2A and NR2B-containing NMDA receptors in cortical long-term potentiation and long-term depression. J Neurosci 24, 7821-7828 (2004).
Mattson et al., Folate and homocysteine metabolism in neural plasticity and neurodegenerative disorders. Trends Neurosci 26, 137-146 (2003).
McCully, Homocysteine, vitamins, and vascular disease prevention. Am J Clin Nutr 86, 1563S-1568S (2007).
Miller et al., Homocysteine, cysteine, and risk of incident colorectal cancer in the Women's Health Initiative observational cohort Am J Clin Nutr 97, 827-834 (2013).
Minghetti, Cyclooxygenase-2 (COX-2) in inflammatory and degenerative brain diseases. J Neuropathol Exp Neurol 63, 901-910 (2004).
Minghetti, Role of COX-2 in inflammatory and degenerative brain diseases. Subcell Biochem 42, 127-141 (2007).
Morikawa et al., Attenuation of focal ischemic brain injury in mice deficient in the epsilon1 (NR2A) subunit of NMDA receptor. J Neurosci 18, 9727-9732 (1998).
Morita et al., Diet-induced hyperhomocysteinemia exacerbates neointima formation in rat carotid arteries after balloon injury. Circulation 103, 133-139 (2001).
Mukaka, Statistics corner: A guide to appropriate use of correlation coefficient in medical research. Malawi Med J 24, 69-71 (2012).
Muralikrishna Adibhatla et al., Phospholipase A2, reactive oxygen species, and lipid peroxidation in cerebral ischemia. Free Radic Biol Med 40, 376-387 (2006).
Mutel et al., In vitro binding properties in rat brain of [3H]Ro 25-6981, a potent and selective antagonist of NMDA receptors containing NR2B subunits. J Neurochem 70, 2147-2155 (1998).
Muzio et al., Multifaceted aspects of inflammation in multiple sclerosis: the role of microglia. J Neuroimmunol 191, 39-44 (2007).
Nakamura, Regulating factors for microglial activation. Biol Pharm Bull 25, 945-953 (2002).
Nogawa et al., Cyclo-oxygenase-2 gene expression in neurons contributes to ischemic brain damage. J Neurosci 17, 2746-2755 (1997).
O'Banion, Cyclooxygenase-2: molecular biology, pharmacology, and neurobiology. Crit Rev Neurobiol 13, 45-82 (1999).
Obeid et al., Mechanisms of homocysteine neurotoxicity in neurodegenerative diseases with special reference to dementia. FEBS Lett 580, 2994-3005 (2006).
Ong et al., Involvement of cytosolic phospholipase A(2), calcium independent phospholipase A(2) and plasmalogen selective phospholipase A(2) in neurodegenerative and neuropsychiatric conditions. Curr Med Chem 17, 2746-2763 (2010).
Owada et al., Molecular cloning of rat cDNA for cytosolic phospholipase A2 and the increased gene expression in the dentate gyrus following transient forebrain ischemia [Molecular Brain Research 25 (1994) 364-368]. Brain Res Mol Brain Res 27, 355 (1994).
Palumbo et al., The cyclooxygenase-2 pathway via the PGE(2) EP2 receptor contributes to oligodendrocytes apoptosis in cuprizone-induced demyelination. J Neurochem 121, 418-427 (2012).
Park et al., Rottierin enhances IL-1 beta-induced COX-2 expression through sustained p38 MAPK activation in MDA-MB-231 human breast cancer cells. Exp Mol Med 43, 669-675 (2011).
Parkkinen et al., Gait impairment in a rat model of focal cerebral ischemia. Stroke Res Treat 2013, 410972 (2013).
Parsons et al., Glutamate in CNS disorders as a target for drug development: an update. Drug News Perspect 11, 523-569 (1998).
Paul et al., NR2B-NMDA receptor-mediated increases in intracellular Ca2+ concentration regulate the tyrosine phosphatase, STEP, and ERK MAP kinase signaling. J Neurochem 114, 1107-1118 (2010).
Paul et al., NMDA-mediated activation of the tyrosine phosphatase STEP regulates the duration of ERK signaling. Nat Neurosci 6, 34-42 (2003).
Perry et al., Prospective study of serum total homocysteine concentration and risk of stroke in middle-aged British men. Lancet 346, 1395-1398 (1995).
Phillis et al., The role of phospholipases, cyclooxygenases, and lipoxygenases in cerebral ischemic/traumatic injuries. Crit Rev Neurobiol 15, 61-90 (2003).

(56) References Cited

OTHER PUBLICATIONS

Pikarsky et al., NF-kappaB functions as a tumour promoter in inflammation-associated cancer. Nature 431, 461-466 (2004).

Pitkonen et al., Long-term evolution of diffusion tensor indices after temporary experimental ischemic stroke in rats. Brain Res 1445, 103-110 (2012).

Poddar et al., NR2B-NMDA receptor mediated modulation of the tyrosine phosphatase STEP regulates glutamate nduced neuronal cell death. J Neurochem 115, 1350-1362 (2010).

Poddar et al., Homocysteine-NMDA receptor-mediated activation of extracellular signal-regulated kinase leads to neuronal cell death. J Neurochem 110, 1095-1106 (2009).

Poddar et al., Novel crosstalk between ERK MAPK and p38 MAPK leads to homocysteine-NMDA receptor-mediated neuronal cell death. J Neurochem 124, 558-570 (2013).

Poddar et al., Homocysteine induces expression and secretion of monocyte chemoattractant protein-1 and interleukin-8 in human aortic endothelial cells: implications for vascular disease Circulation 103, 2717-2723 (2001).

Quan et al., EP2 receptor signaling pathways regulate classical activation of microglia. J Biol Chem 288, 9293-9302 (2013).

Raivich et al., Neuroglial activation repertoire in the injured brain: graded response, molecular mechanisms and cues to physiological function. Brain Res Brain Res Rev 30, 77-105 (1999).

Rajagopal et al., Role of GluN2A NMDA receptor in homocysteine-induced prostaglandin E2 release from neurons. J Neurochem 150, 44-55 (2019).

Fisher et al.. Update of the stroke therapy academic industry roundtable preclinical recommendations. Stroke 40, 2244-2250 (2009).

Fitzgerald, COX-2 and beyond: Approaches to prostaglandin inhibition in human disease. Nat Rev Drug Discov 2, 879-890 (2003).

Foster et al., Distinct roles of NR2A and NR2B cytoplasmic tails in long-term potentiation. J Neurosci 30, 2676-2685 (2010).

Fox et al., Contribution of NR2A and NR2B NMDA subunits to bidirectional synaptic plasticity in the hippocampus in vivo. Hippocampus 16, 907-915 (2006).

Ganapathy et al., The role of N-methyl-D-aspartate receptor activation in homocysteine-induced death of retinal ganglion cells. Invest Ophthalmol Vis Sci 52, 5515-5524 (2011).

Gilfix et al., Novel reductant for determination of total plasma homocysteine. Clin Chem 43, 687-688 (1997).

Glaum et al., Acute- and long-term glutamate-mediated regulation of [Ca++]i in rat hippocampal pyramidal neurons in vitro. J Pharmacol Exp Ther 253, 1293-1302 (1990).

Gogas, Glutamate-based therapeutic approaches: NR2B receptor antagonists. Curr Opin Pharmacol 6, 68-74 (2006).

Griswold et al., Constitutive cyclooxygenase (COX-1) and inducible cyclooxygenase (COX-2): rationale for selective inhibition and progress to date. Med Res Rev 16, 181-206 (1996).

Grynkiewicz et al., A new generation of Ca2+ indicators with greatly improved fluorescence properties. J Biol Chem 260, 3440-3450 (1985).

Guo et al., Activation of the p38 MAPK/NF-kappaB pathway contributes to doxorubicin-induced inflammation and cytotoxicity in H9c2 cardiac cells. Mol Med Rep 8, 603-608 (2013).

Gupta et al., Mouse models of cystathionine beta-synthase deficiency reveal significant threshold effects of hperhomocysteinemia. Faseb J 23, 883-893 (2009).

Habeeb et al., Design and synthesis of 4,5-diphenyl-4-isoxazolines: novel inhibitors of cyclooxygenase-2 with analgesic and antiinflammatory activity. J Med Chem 44, 2921-2927 (2001).

Hankey et al., Homocysteine and stroke. Curr Opin Neurol 14, 95-102 (2001).

Hardingham et al., The Yin and Yang of NMDA receptor signalling. Trends Neurosci 26, 81-89 (2003).

Hardingham et al., Extrasynaptic NMDARs oppose synaptic NMDARs by triggering CREB shut-off and cell death pathways. Nat Neurosci 5, 405-414 (2002).

Holscher, Inhibitors of cyclooxygenases produce amnesia for a passive avoidance task in the chick. Eur J Neurosci 7, 1360-1365 (1995).

Huang et al., SOD1 down-regulates NF-kappaB and c-Myc expression in mice after transient focal cerebral ischemia. J Cereb Blood Flow Metab 21, 163-173 (2001).

Hyrc et al., Ionized intracellular calcium concentration predicts excitotoxic neuronal death: observations with low-affinity fluorescent calcium indicators. J Neurosci 17, 6669-6677 (1997).

Ivanov et al., Opposing role of synaptic and extrasynaptic NMDA receptors in regulation of the extracellular signal-regulated kinases (ERK) activity in cultured rat hippocampal neurons. J Physiol 572, 789-798 (2006).

Jacobsen et al., Rapid HPLC determination of total homocysteine and other thiols in serum and plasma: sex differences and correlation with cobalamin and folate concentrations in healthy subjects. Clin Chem 40, 873-881 (1994).

Janson et al., Prevalence of hyperhomocysteinemia in an elderly population. Am J Hypertens 15, 394-397 (2002).

Jara-Prado et al., Homocysteine-induced brain lipid peroxidation: effects of NMDA receptor blockade, antioxidant treatment, and nitric oxide synthase inhibition. Neurotox Res 5, 237-243 (2003).

Jindal et al., Hyperhomocysteinemia leads to exacerbation of ischemic brain damage: Role of GluN2A NMDA receptors. Neurobiol Dis 127, 287-302 (2019).

Johnson et al., Myxobacteria versus sponge-derived alkaloids: the bengamide family identified as potent immune modulating agents by scrutiny of LC-MS/ELSD libraries. Bioorg Med Chem 20, 4348-4355 (2012).

Johnston et al., Global variation in stroke burden and mortality: estimates from monitoring, surveillance, and modelling. Lancet Neurol 8, 345-354 (2009).

Kaltschmidt et al., Cyclooxygenase-2 is a neuronal target gene of NF-kappaB. BMC Mol Biol 3, 16 (2002).

Kang et al., Hyperhomocyst(e)inemia as a risk factor for occlusive vascular disease. Annu Rev Nutr 12, 279-298 (1992).

Kang et al., Cyclooxygenase-2 gene transcription in a macrophage model of inflammation. J Immunol 177, 8111-8122 (2006).

Karim et al., Differential cyclooxygenase-2 enzyme expression in radiosensitive versus radioresistant glioblastoma multiforme cell lines. Anticancer Res 25, 675-679 (2005).

Karin et al., Phosphorylation meets ubiquitination: the control of NF-[kappa]B activity. Annu Rev Immunol 18, 621-663 (2000).

Karin et al., The IKK NF-kappa B system: a treasure trove for drug development. Nat Rev Drug Discov 3, 17-26 (2004).

Kaufmann et al., Cyclooxygenases and the central nervous system. Prostaglandins 54, 601-624 (1997).

Kaufmann et al., Cyclooxygenase-2 expression during rat neocortical development and in Rett syndrome. Brain Dev 19, 25-34 (1997).

Kim et al., Roles of ERK and p38 mitogen-activated protein kinases in phorbol ester-induced NF-kappaB activation and COX-2 expression in human breast epithelial cells. Chem Biol Interact 171, 133-141 (2008).

Kim et al., Differential roles of NR2A- and NR2B-containing NMDA receptors in Ras-ERK signaling and AMPA receptoi trafficking. Neuron 46, 745-760 (2005).

Kinarsky et al., Identification of subunit- and antagonist-specific amino acid residues in the N-Methyl-D-aspartate receptor glutamate-binding pocket. J Pharmacol ExpTher 313, 1066-1074 (2005).

Kirkby et al., Systematic study of constitutive cyclooxygenase-2 expression: Role of NF-kappaB and NFAT transcriptional pathways. Proc Natl Acad Sci U S A 113, 434-439 (2016).

Kirkby et al., Cyclooxygenase-1, not cyclooxygenase-2, is responsible for physiological production of prostacyclin in the cardiovascular system. Proc Natl Acad Sci U S A 109, 17597-17602 (2012).

Kramer et al., p38 mitogen-activated protein kinase phosphorylates cytosolic phospholipase A2 (cPLA2) in thrombin-stimulated platelets. Evidence that proline-directed phosphorylation is not required for mobilization of arachidonic acid by cPLA2. J Biol Chem 271, 27723-27729 (1996).

Kruman et al., Homocysteine elicits a DNA damage response in neurons that promotes apoptosis and hypersensitivity to excitotoxicity. J Neurosci 20, 6920-6926 (2000).

(56) References Cited

OTHER PUBLICATIONS

Kruman et al., Folic acid deficiency and homocysteine impair DNA repair in hippocampal neurons and sensitize them to amyloid toxicity in experimental models of Alzheimer's disease. J Neurosci 22, 1752-1762 (2002).

Laemmli, Cleavage of structural proteins during the assembly of the head of bacteriophage T4. Nature 227, 680-685 (1970).

Lai et al., Stroke intervention pathways: NMDA receptors and beyond. Trends Mol Med 17, 266-275 (2011).

Lasa et al., Regulation of cyclooxygenase 2 mRNA stability by the mitogen-activated protein kinase p38 signaling cascade. Mol Cell Biol 20, 4265-4274 (2000).

Lazarewicz et al., Homocysteine-evoked 45Ca release in the rabbit hippocampus is mediated by both NMDA and group I metabotropic glutamate receptors: in vivo microdialysis study Neurochem Res 28, 259-269 (2003).

Lee et al., The changing landscape of ischaemic brain injury mechanisms. Nature 399, A7-14 (1999).

Li et al., Differential regulation of synaptic and extra-synaptic NMDA receptors. Nat Neurosci 5, 833-834 (2002).

Li et al., Developmental changes in localization of NMDA receptor subunits in primary cultures of cortical neurons. Eur J Neurosci 10, 1704-1715 (1998).

Li et al., Distinct roles for Ras-guanine nucleotide-releasing factor 1 (Ras-GRF1) and Ras-GRF2 in the induction of long-term potentiation and long-term depression. J Neurosci 26, 1721-1729 (2006).

\* cited by examiner

A)

B)

A)

A)

B)

(a)

(b)

(c)

(d)

(a)

(b)

(B)

(C)

(a)

(b)

(c)

(d)

MPX-007

MPX-004

(a)

(b)

(c)

(a)

(b)

(c)

(a)

(b)

(c)

(d)

COMPOSITIONS AND METHODS FOR TREATING BRAIN INJURY

CROSS-REFERENCE TO RELATED APPLICATION

This application is the § 371 U.S. National Stage of International Application No. PCT/US2019/040769, filed Jul. 8, 2019, which claims the benefit of U.S. Provisional Patent Application No. 62/695,346, filed Jul. 9, 2018, each of which is incorporated herein by reference in its entirety.

GOVERNMENT FUNDING

This invention was made with government support under NS083914 and NS059962 awarded by the national Institutes of Health. The government has certain rights in the invention.

SUMMARY

This disclosure describes, in one aspect, a method for treating a hyperhomocysteinemic subject having cerebral ischemic stroke. Generally the method includes administering to the hyperhomocysteinemic subject, following cerebral stroke, a composition that includes an inhibitor or an antagonist of a GluN2A-containing N-methyl-D-aspartate receptor (NMDAR) in an amount effective to ameliorate at least one symptom or clinical sign of cerebral stroke.

In some embodiments, the inhibitor of GluN2A-NMDAR includes NVP-AAM077.

In some embodiments, the antagonist of GluN2A-NMDAR includes {(S)-5-[(R)-2-amino-2-carboxyethyl]-1-[4-(3-fluoropropyl) phenyl]-4,5-dihydro-1H-pyrazole-3-carboxylic acid} (ST3), {(S)-5-[(R)-2-amino-2-carboxyethyl]-1-(4-fluorophenyl)-4,5-dihydro-1H-pyrazole-3-carboxylic acid} (ST1), {(S)-5-[(R)-2-amino-2-carboxyethyl]-1-(4-bromophenyl)-4,5-dihydro-1H-pyrazole-3-carboxylic acid} (ST6), {(S)-5-[(R)-2-amino-2-carboxyethyl]-1-phenyl-4,5-dihydro-1H-pyrazole-3-carboxylic acid} (FRA-19), 3-chloro-4-fluoro-N-[(4-{[2-phenylcarbonyl)hydrazine]carbonyl}phenyl)methyl}benzenesulfonamide) (TCN-201), 5-(((3-chloro-4-fluorophenyl)sulfonamido)methyl)-N-((2-methylthiazol-5-yl)methyl)pyrazine-2-carboxamide (MPX-004), 5-(((3,4-difluorophenyl)sulfonamido)methyl)-6-methyl-N-((2-methylthiazol-5-yl)methyl)pyrazine-2-carboxamide (MPX-007), or a derivative of TCN-201.

In another aspect, this disclosure describes a method for treating a hyperhomocysteinemic subject having a neurological disorder exacerbated by homocysteine-induced neuroinflammation. Generally, the method includes administering to the hyperhomocysteinemic subject a composition that includes an inhibitor or an antagonist of a GluN2A-containing N-methyl-D-aspartate receptor (NMDAR) in an amount effective to decrease neuroinflammation.

In some embodiments, the neurological disorder can include ischemic stroke, traumatic brain injury, or vascular dementia.

In some embodiments, the inhibitor of GluN2A-NMDAR can include NVP-AAM077.

In some embodiments, the antagonist of GluN2A-NMDAR can include {(S)-5-[(R)-2-amino-2-carboxyethyl]-1-[4-(3-fluoropropyl) phenyl]-4,5-dihydro-1H-pyrazole-3-carboxylic acid} (ST3), {(S)-5-[(R)-2-amino-2-carboxyethyl]-1-(4-fluorophenyl)-4,5-dihydro-1H-pyrazole-3-carboxylic acid} (ST1), {(S)-5-[(R)-2-amino-2-carboxyethyl]-1-(4-bromophenyl)-4,5-dihydro-1H-pyrazole-3-carboxylic acid} (ST6), {(S)-5-[(R)-2-amino-2-carboxyethyl]-1-phenyl-4,5-dihydro-1H-pyrazole-3-carboxylic acid} (FRA-19), 3-chloro-4-fluoro-N-[(4-{[2-phenylcarbonyl)hydrazine]carbonyl}phenyl)methyl}benzenesulfonamide) (TCN-201), 5-(((3-chloro-4-fluorophenyl)sulfonamido)methyl)-N-((2-methylthiazol-5-yl)methyl)pyrazine-2-carboxamide (MPX-004), 5-(((3,4-difluorophenyl)sulfonamido)methyl)-6-methyl-N-((2-methylthiazol-5-yl)methyl)pyrazine-2-carboxamide (MPX-007), or a derivative of TCN-201.

In some embodiments, the neuroinflammation can be mediated by prostaglandin E2 (PGE2).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

*p<0.001 from corresponding control. (G) Quantitative analysis of cells with pyknotic DNA following Hoechst DNA staining of rat cortical neuron cultures exposed to OGD in the absence or presence of L-Hcy (50 μM) for 2 h followed by re-oxygenation for 22 hr. Values are mean±SEM (n=1500 cells/condition from 4 experiments). *p<0.001 from control and **p<0.001 from OGD/ReOx.

Figure 10:
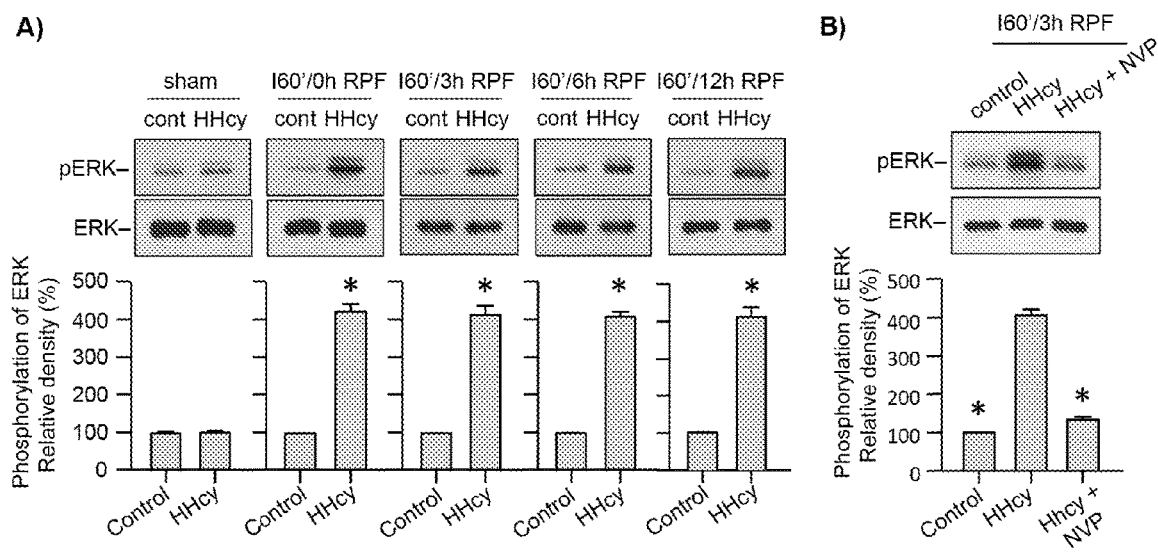

FIG. 10. ERK MAPK phosphorylation. (A) Control and hyperhomocysteinemic (HHcy) rats were subjected to MCAO for 60 min followed by reperfusion (sham, 0, 3, 6, 12 h). Cortical tissue lysates from the ipsilateral hemisphere were analyzed by immunoblotting, using anti-pERK and anti-ERK antibodies. (B) Control, HHcy and HHcy rats treated with NVP-AAM077 (HHcy+NVP) were subjected to MCAO for 60 min followed by reperfusion for 3 h. Cortical tissue lysates from the ipsilateral hemisphere were analyzed by immunoblotting, using anti-pERK and anti-ERK antibodies. The extent of ERK MAPK phosphorylation was quantified using computer-assisted densitometry and Image J analysis. Values are mean±SEM (n=5). (A) *p<0.001 from corresponding control. (B) *p<0.001 from HHcy.

Figure 11:
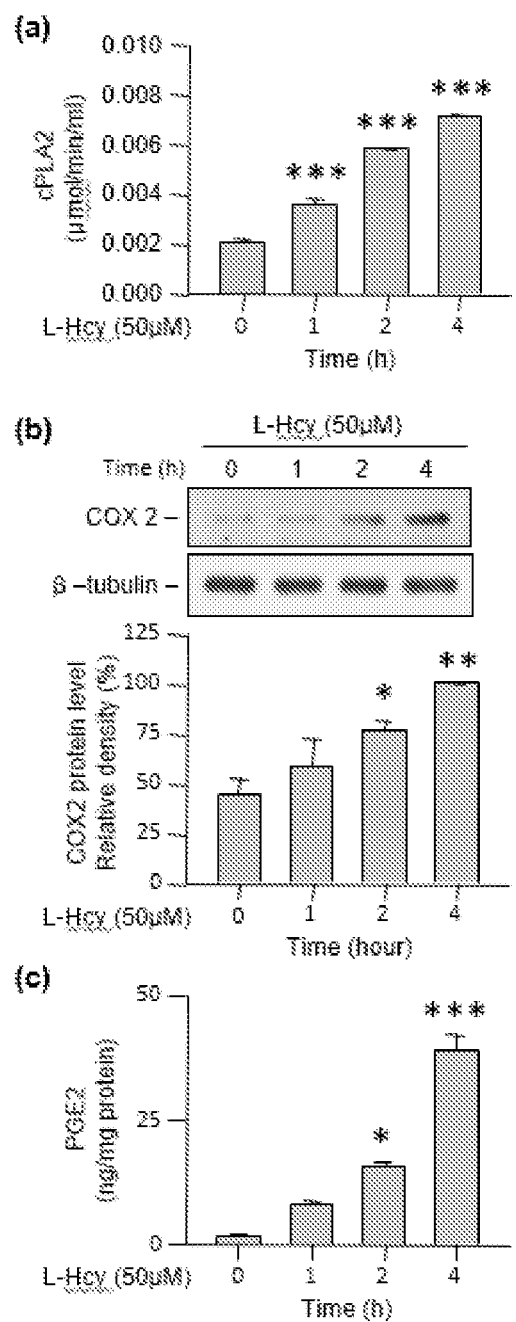

FIG. 11. Homocysteine induces cPLA2 activity, COX2 protein expression and PGE2 release in neurons. Neuron cultures were treated with 50 μM L-homocysteine (L-Hcy) for the specified times. (A) Equal amount of protein from cell lysates prepared in PBS was analyzed for cPLA2 activity using enzymatic assay. (B) Equal amount of protein from cell lysates of each sample was processed for immunoblot analysis using anti-COX2 (upper panel) and β-tubulin (lower panel) antibodies. Quantification of COX2 protein expression from the immunoblots by computer-assisted densitometry and Image J analysis is shown. (C) Equal amounts of culture media from each sample were analyzed for PGE2 levels using enzyme immunoassay to estimate PGE2 release from neurons. Values are represented as mean±SEM (n=5). *p<0.05, p<0.001 and *p<0.0001 from 0 min homocysteine treatment.

Figure 2:
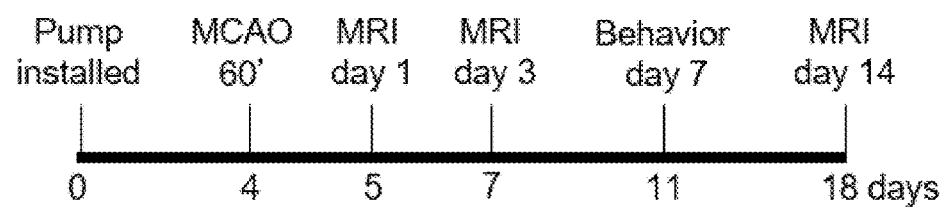
FIG. 2. Exacerbation of ischemic brain damage in hyperhomocysteinemic rats at 24 hours post-occlusion evaluated from T2 maps. (A) Schematic representation of the timeline of implantation of osmotic pumps, MCAO, MRI scans and behavioral assessments. (B) Quantitative analysis of stroke mortality rate (%) in control and hyperhomocysteinemic (HHcy) rats. (C) Representative T2 maps acquired from sham control and HHcy rats, as well as control and HHcy rats subjected to MCAO (60 minutes) and reperfusion (24 hours). (D) Quantitative analysis of ischemic lesion volume in control and HHcy rats subjected to ischemic insult and reperfusion, expressed as mean±SEM (control: n=11, HHcy: n=15); *$p<0.0001$ for control vs. HHcy rats.
Figure 2:
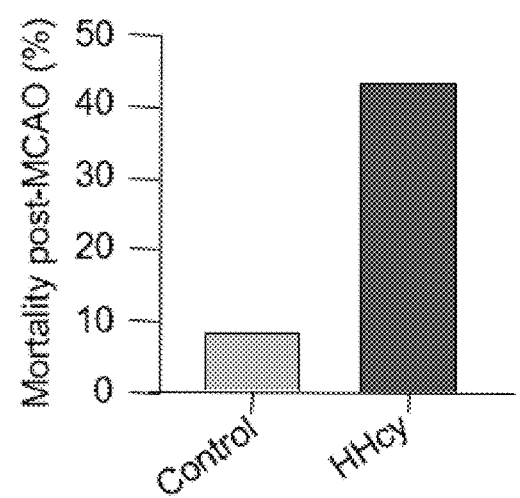
Figure 2:
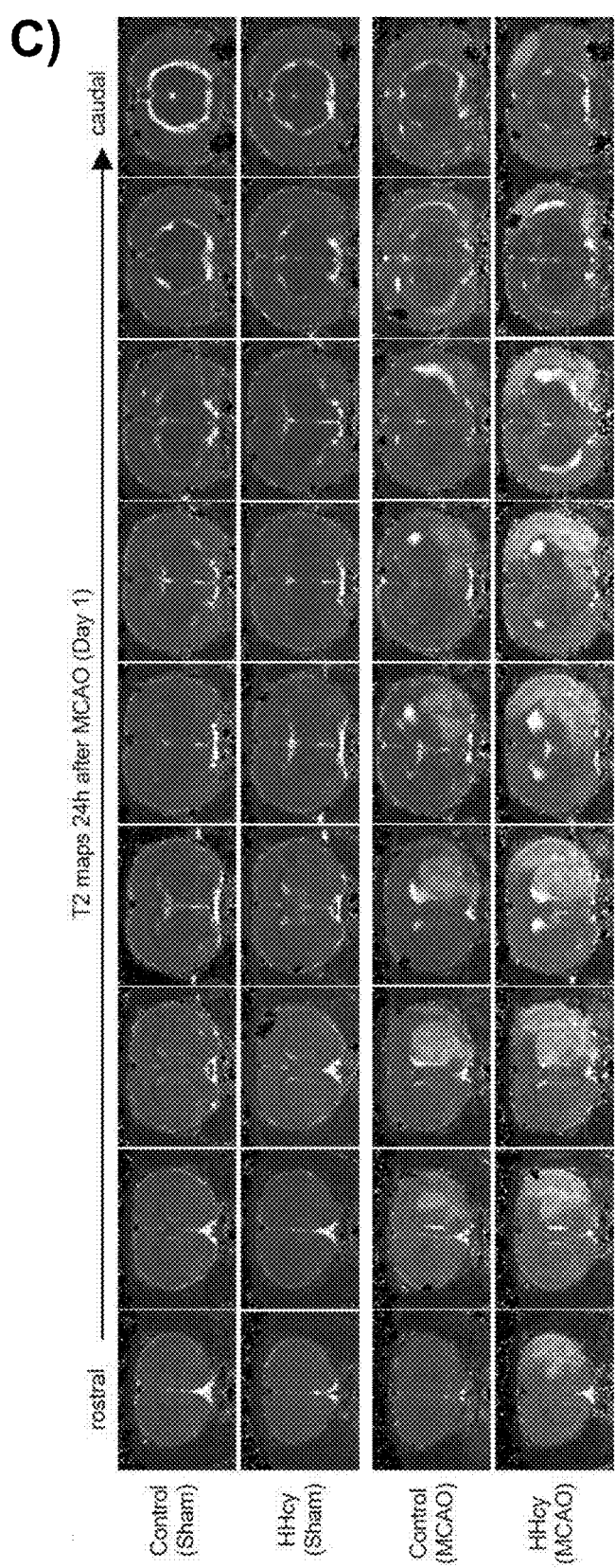
Figure 2:
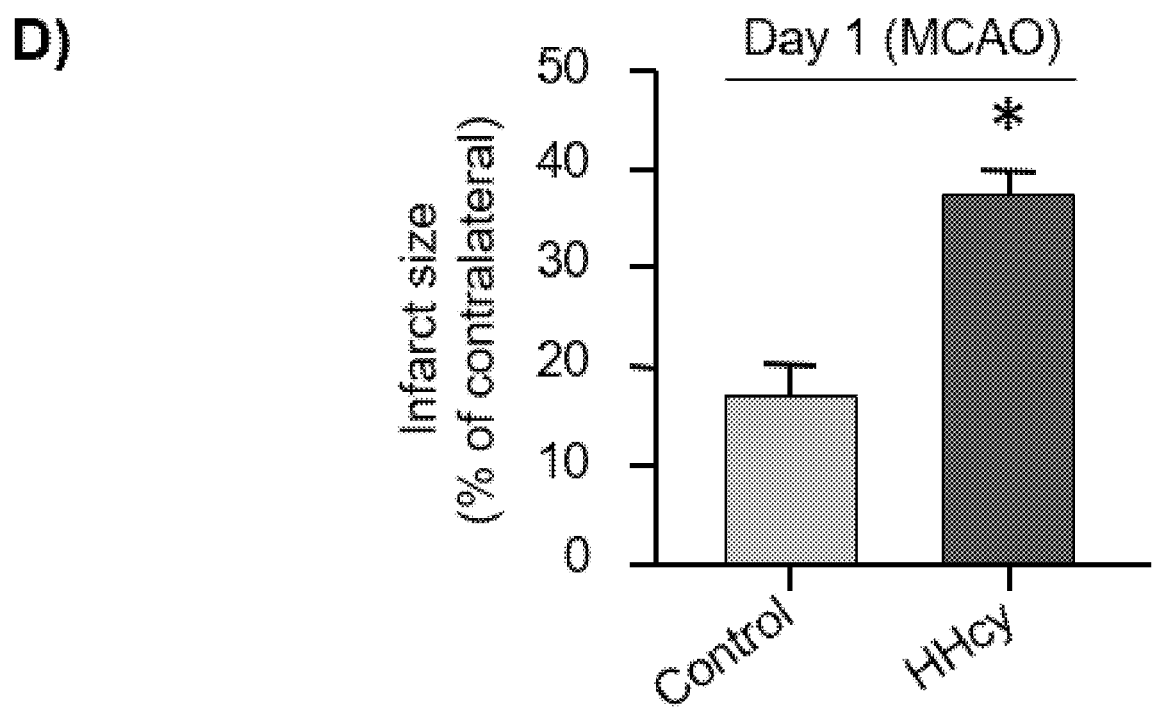
Figure 12:
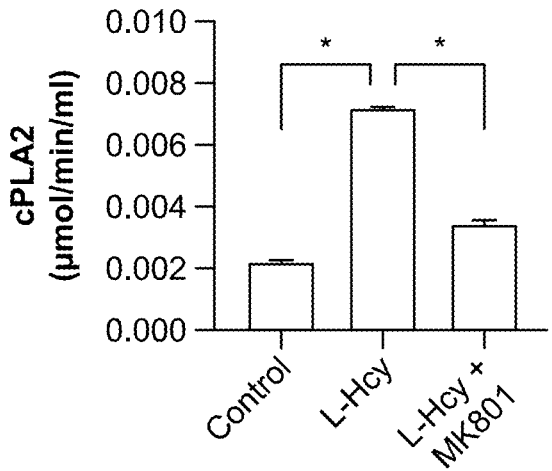
Figure 12:
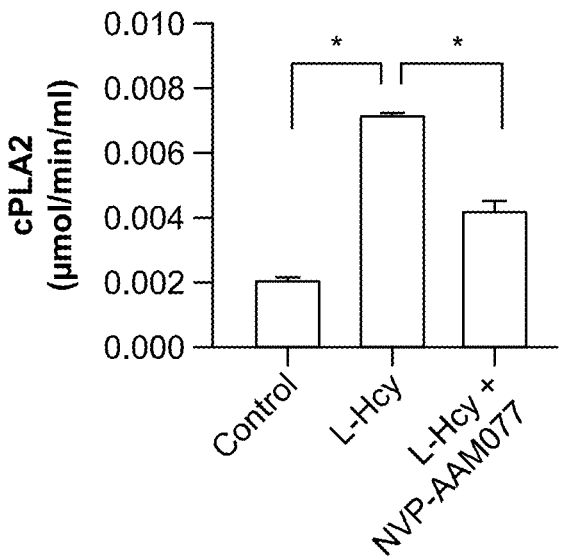
Figure 12:
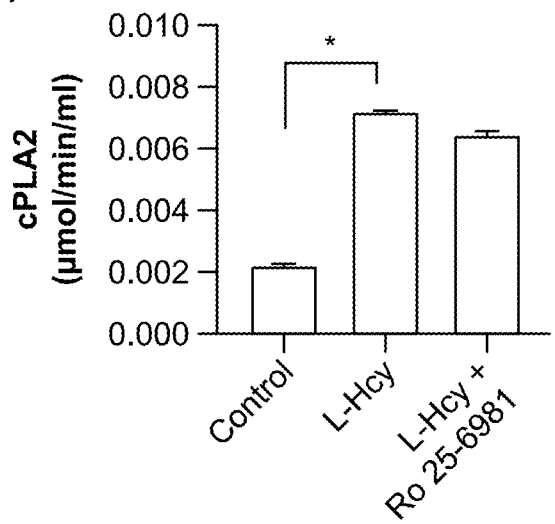
Figure 12:
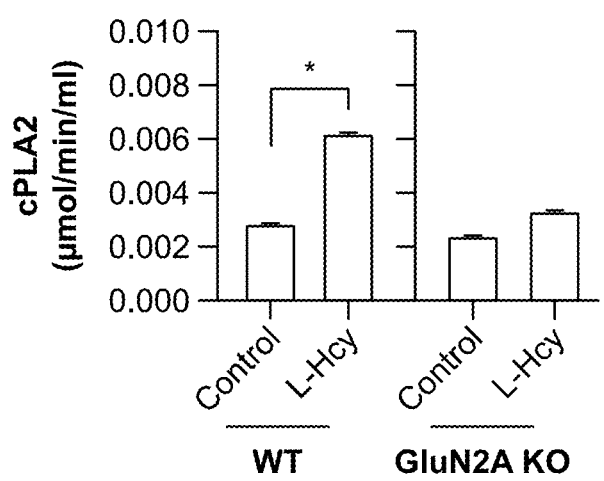

FIG. 12 (Raj FIG. 2). Role of GluN2A-NMDAR in homocysteine-induced cPLA2 activation in neurons. (A) Rat neuronal cultures were treated with 50 μM L-homocysteine (L-Hcy) for four hours in the absence or presence of MK801 (10 μM). (B) Rat neuronal cultures were treated with 50 μM L-homocysteine (L-Hcy) for four hours in the absence or presence of NVP-AAM077 (30 nM). (C) Rat neuronal cultures were treated with 50 μM L-homocysteine (L-Hcy) for four hours in the absence or presence of Ro 25-6981 (1 μM). (D) WT and GluN2A-KO mice neuronal cultures were treated with 50 μM L-Hcy for four hours. Equal amounts of protein from each sample were analyzed for cPLA2 activity using enzymatic assay. Values are expressed as mean±SEM (n=5). *p<0.0001 from four-hour homocysteine treatment.

Figure 3:
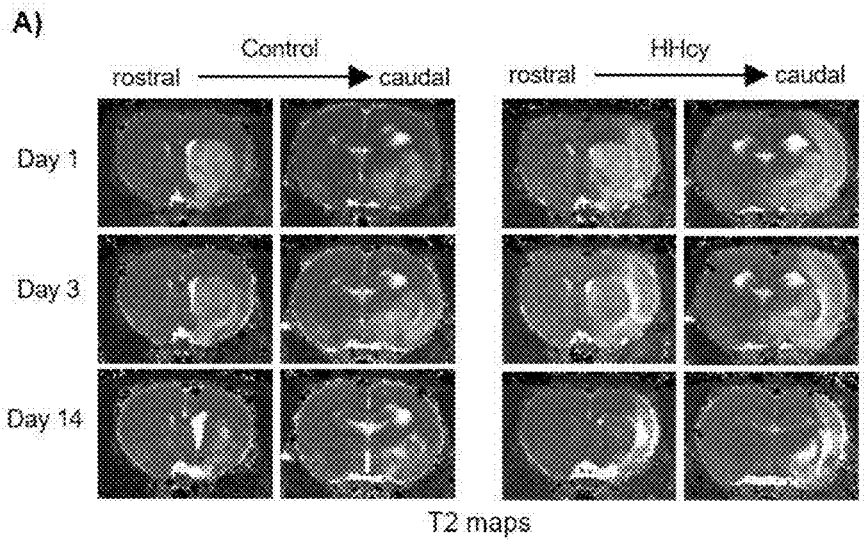
FIG. 3. Temporal evolution of ischemic brain damage in hyperhomocysteinemic rats evaluated from T2, ADC and FA maps. (A) Representative T2 maps from day 1, day 3, and day 14 after MCAO, acquired from control and hyperhomocysteinemic rats (HHcy) showing changes in ischemic lesion size from rostral to caudal regions of the brain. Corresponding bar diagram provide quantitative analysis of total infarct volume, expressed as mean±SEM (on day 1 and day 3—control: n=11, HHcy: n=15; on day 14—control: n=10, HHcy: n=14). (B) Representative ADC maps acquired from control and HHcy rats at day 14 post-MCAO featuring hyperintense areas that co-localize with the lesion area in the T2 maps at day 14 post-MCAO. Quantitative analysis of ADC values in the lesion area, expressed as mean±SEM (control: n=10, HHcy: n=14). (C) Representative FA maps acquired from the same slices as ADC and T2 maps at 14 days post-MCAO as well as quantitative analysis of FA values expressed as mean±SEM (control: n=10, HHcy: n=14). (D) Representative cresyl violet stained images of rostral and caudal regions of the brain from control and HHcy rats 14 days after MCAO. *p<0.05, p<0.01 and *p<0.001 for control vs. HHcy rats.
Figure 3:
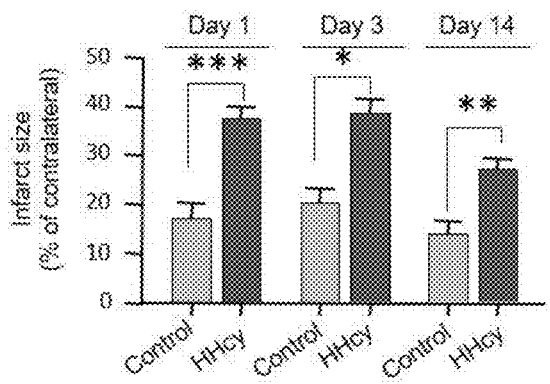
Figure 3:
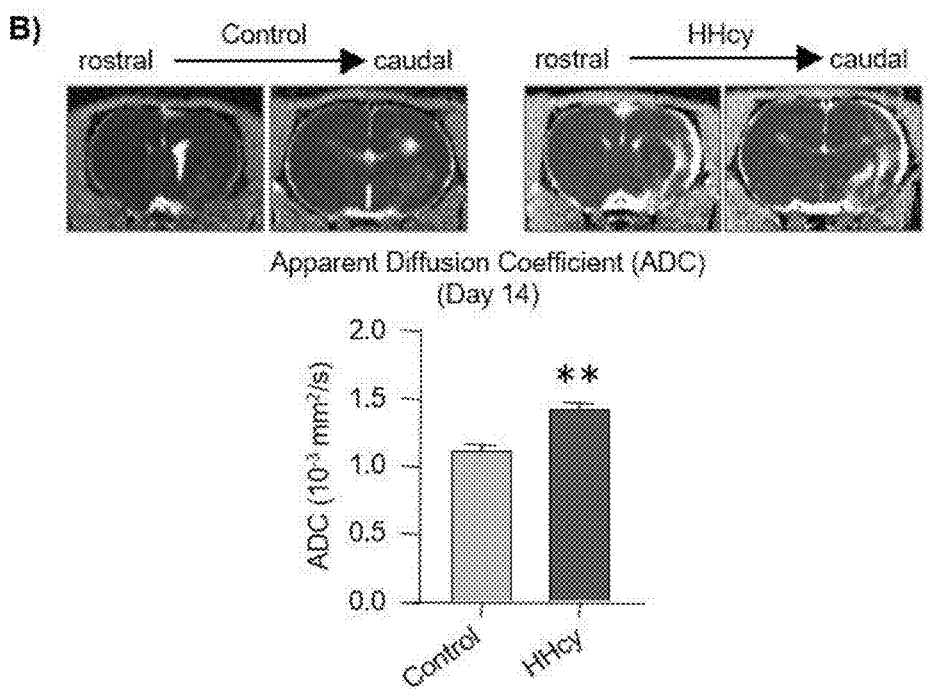
Figure 3:
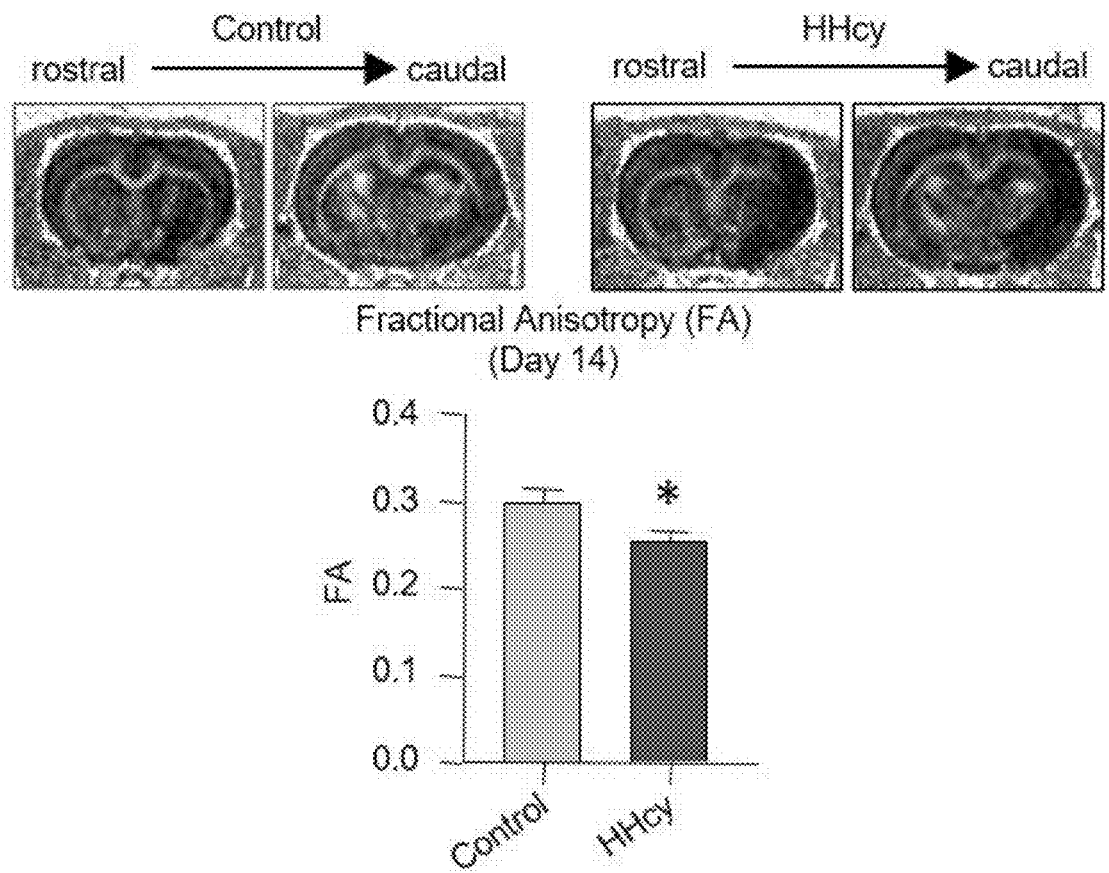
Figure 3:
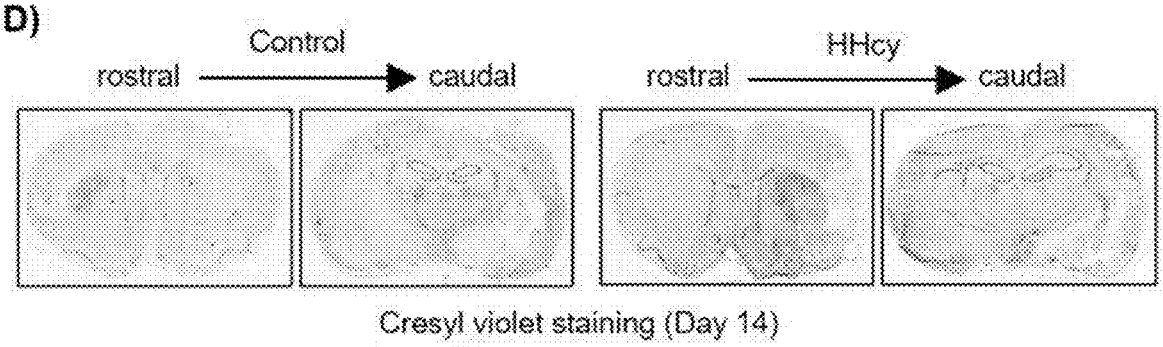
Figure 13:
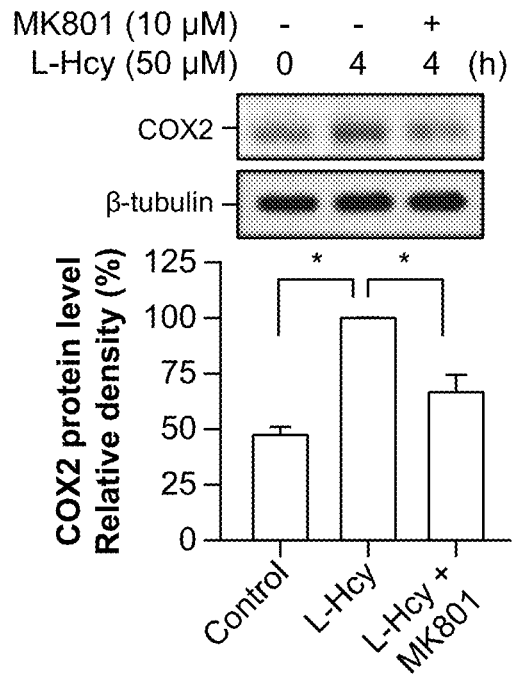
Figure 13:
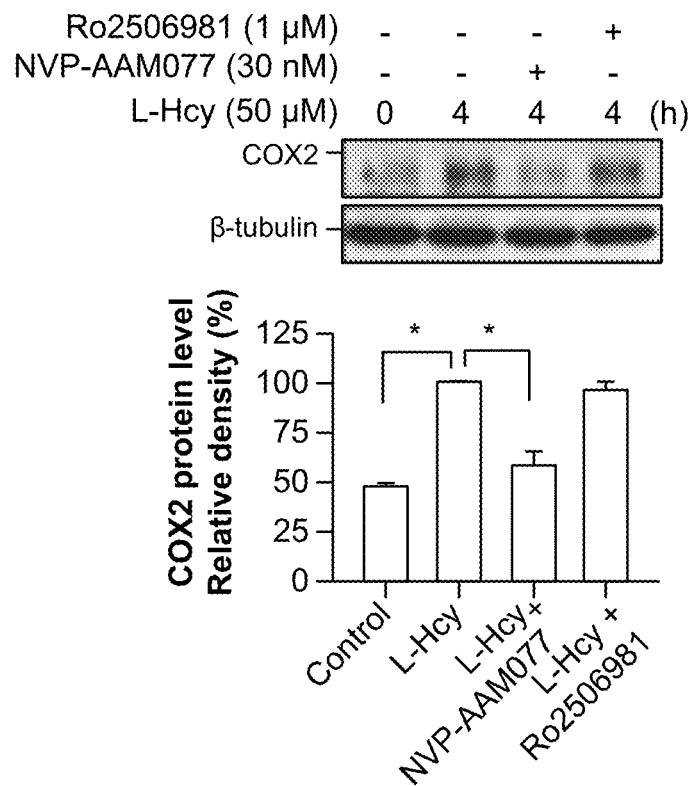
Figure 13:
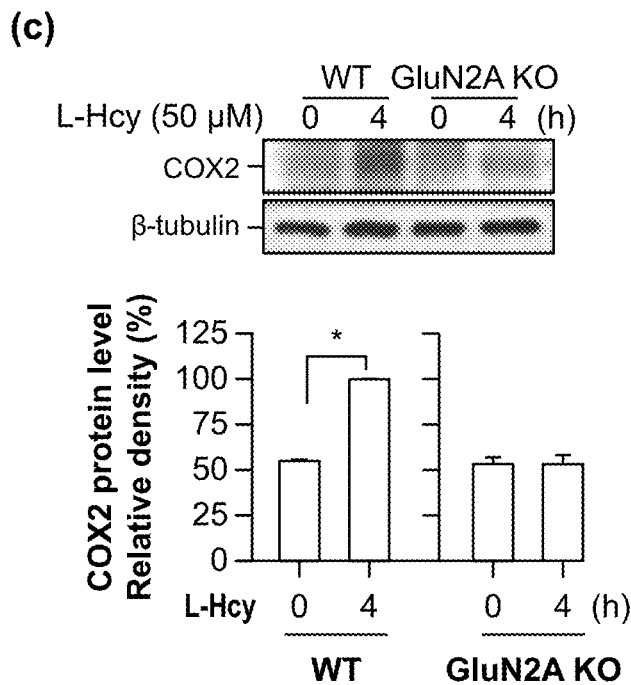

FIG. 13. (Raj FIG. 3). Role of GluN2A-NMDAR in homocysteine-mediated increase in COX2 protein level in neurons. (A) Rat neuronal cultures were treated with 50 μM L-homocysteine (L-Hcy) for four hours in the absence or presence of MK801 (10 μM) or (b) NVP-AAM077 (30 nM). (B) Rat neuronal cultures were treated with 50 μM L-homocysteine (L-Hcy) for four hours in the absence or presence of Ro 25-6981 (1 μM). (C) WT and GluN2A-KO mice neuronal cultures were treated with 50 μM L-Hcy for four hours. Cell lysates were analyzed by immunoblotting with anti-COX2 (upper panels) and β-tubulin (lower panels) antibodies. COX2 protein levels were quantified using computer-assisted densitometry and Image J analysis. Values are mean±±SEM (n=5). *p<0.001 from four-hour homocysteine treatment.

Figure 14:
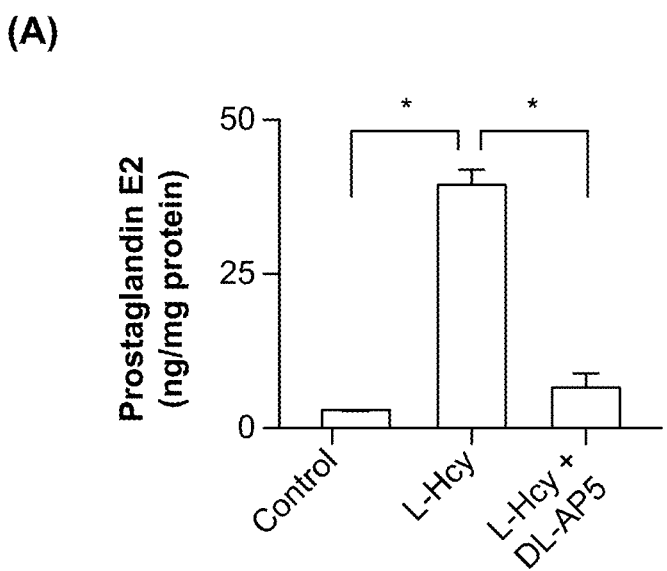
Figure 14:
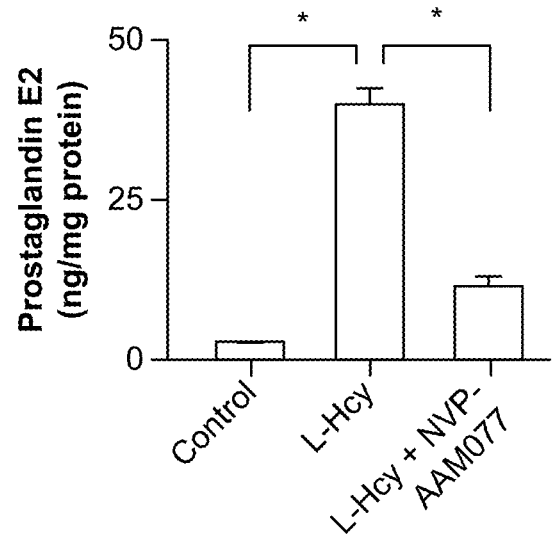
Figure 14:
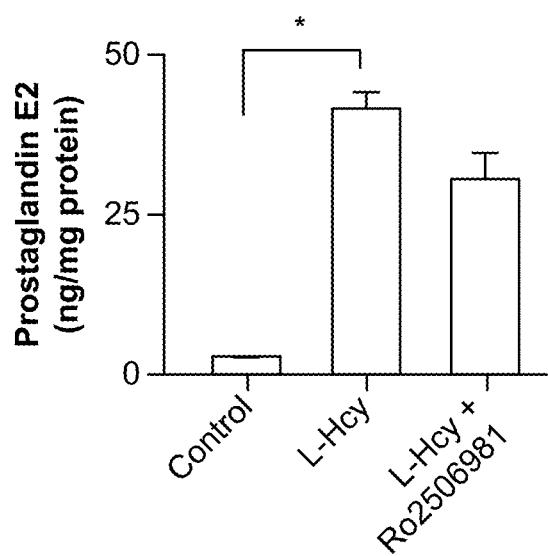

FIG. 14. Homocysteine-induced PGE2 release from neurons is GluN2A-NMDAR dependent. (A) Neuron cultures obtained from rat embryos were treated with 50 μM L-homocysteine (L-Hcy) for four hours in the absence or presence of DL-AP5 (200 μM). (B) Neuron cultures obtained from rat embryos were treated with 50 μM L-homocysteine (L-Hcy) for four hours in the absence or presence of NVP-AAM077 (30 nM). (C) Neuron cultures obtained from rat embryos were treated with 50 μM L-homocysteine (L-Hcy) for four hours in the absence or presence of Ro 2506981 (1 μM). Equal amounts of culture media from each sample were analyzed for PGE2 levels using enzyme immunoassay to estimate PGE2 released from neurons. Values are represented as mean±SEM (n=5). *p<0.0001 from four-hour homocysteine treatment.

Figure 15:
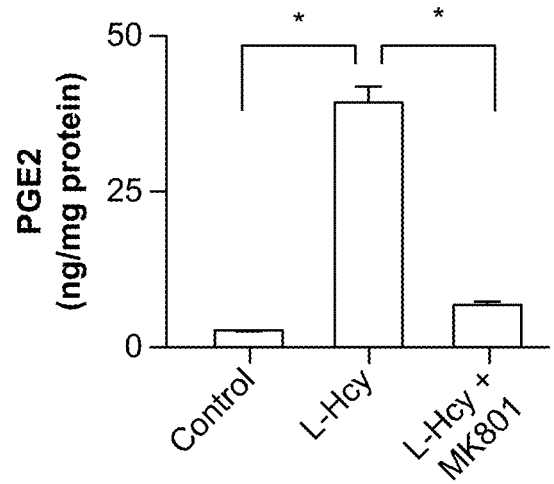
Figure 15:
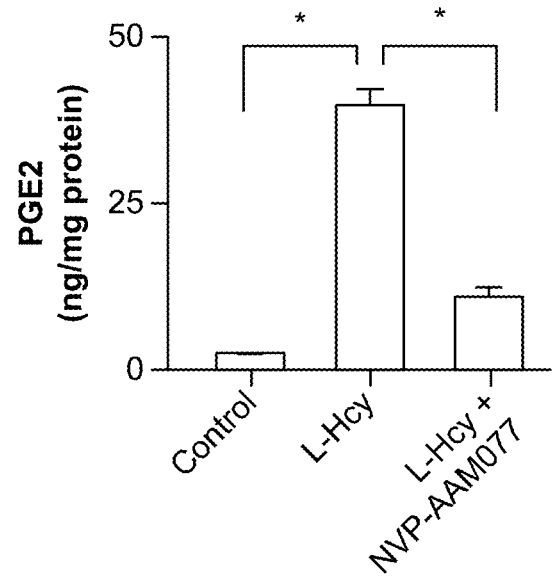
Figure 15:
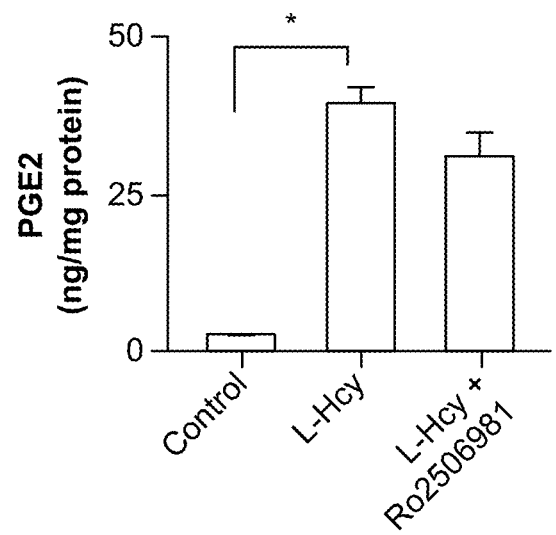
Figure 15:
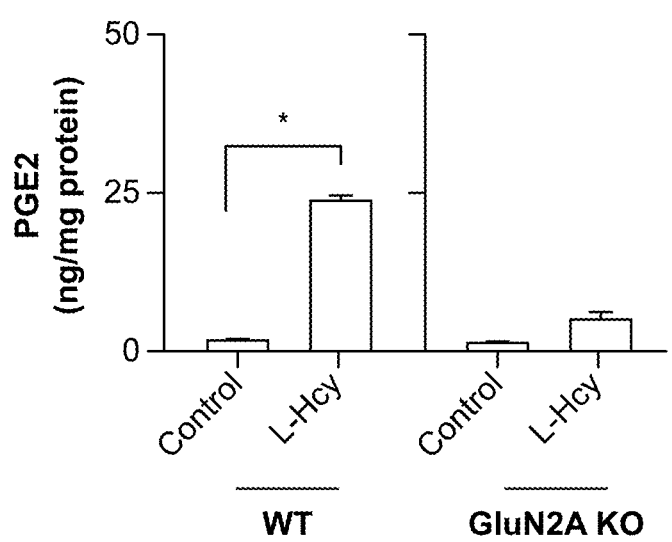

FIG. 15. Role of GluN2A-NMDAR in homocysteine-induced PGE2 release from neurons. (A) Rat neuronal cultures were treated with 50 μM L-homocysteine (L-Hcy) for four hours in the absence or presence of MK801 (10 μM). (B) Rat neuronal cultures were treated with 50 μM L-homocysteine (L-Hcy) for four hours in the absence or presence of NVP-AAM077 (30 nM). (C) Rat neuronal cultures were treated with 50 μM L-homocysteine (L-Hcy) for four hours in the absence or presence of Ro2506981 (1 μM). (D) WT and GluN2A-KO mice neuronal cultures were treated with 50 μM L-Hcy for four hours. Equal amounts of culture media from each sample were analyzed for PGE2 levels using ELISA. Values are represented as mean SD (number of independent cell culture experiments=4-7). *p<0.0001 from four-hour homocysteine treatment.

Figure 16:
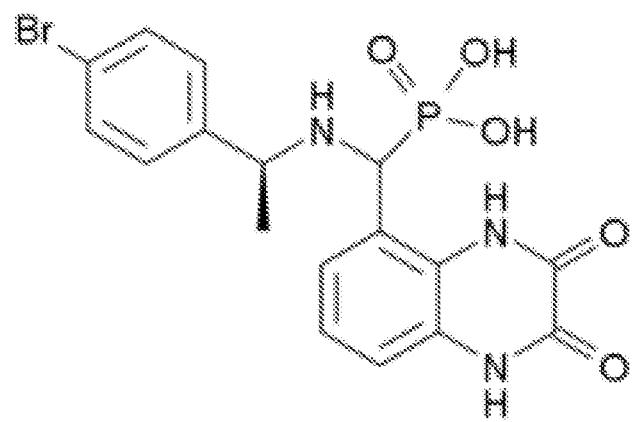

FIG. 16. Chemical structure of NVP-AAM077 ({[(1S)-1-(4-bromophenyl)ethyl]amino}-(2,3-dioxo-1,4-dihydroquinoxalin-5-yl)methyl)phosphonic acid.

Figure 17:
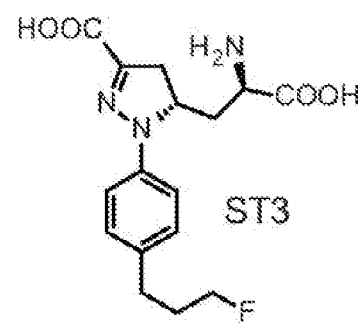

FIG. 17. Chemical structure of ST3 {(S)-5-[(R)-2-amino-2-carboxyethyl]-1-[4-(3-fluoropropyl) phenyl]-4,5-dihydro-1H-pyrazole-3-carboxylic acid}.

Figure 18:
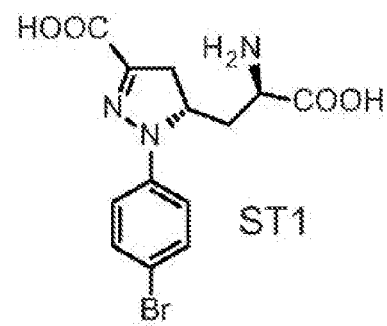

FIG. 18. Chemical structure of ST {(S)-5-[(R)-2-amino-2-carboxyethyl]-1-(4-fluorophenyl)-4,5-dihydro-1H-pyrazole-3-carboxylic acid}.

Figure 19:
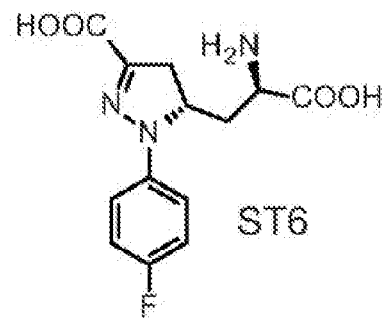

FIG. 19. Chemical structure of ST6 {(S)-5-[(R)-2-amino-2-carboxyethyl]-1-(4-bromophenyl)-4,5-dihydro-1H-pyrazole-3-carboxylic acid}.

Figure 20:
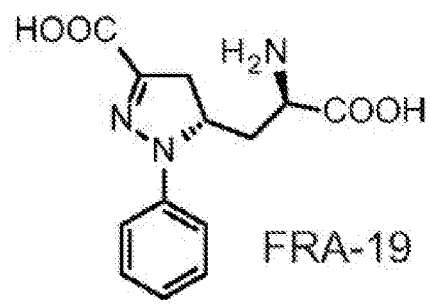

FIG. 20. Chemical structure of FRA-19 {(S)-5-[(R)-2-amino-2-carboxyethyl]-1-phenyl-4,5-dihydro-1H-pyrazole-3-carboxylic acid}.

Figure 21:
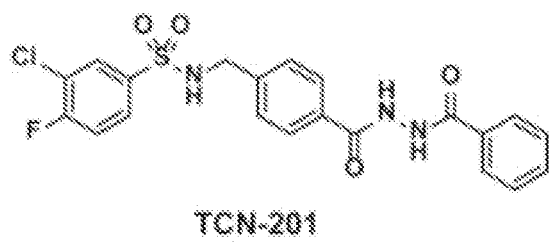

FIG. 21. Chemical structure of TCN-201 3-chloro-4-fluoro-N-[(4-{[2-phenylcarbonyl)hydrazine] carbonyl}phenyl)methyl}benzenesulfonamide).

Figure 22:
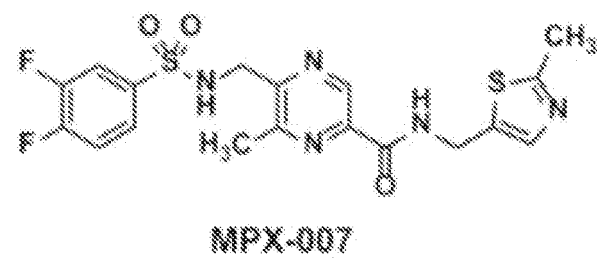

FIG. 22. Chemical structure of MPX-007 (5-(((3,4-difluorophenyl)sulfonamido)methyl)-6-methyl-N-((2-methylthiazol-5-yl)methyl)pyrazine-2-carboxamide.

Figure 23:
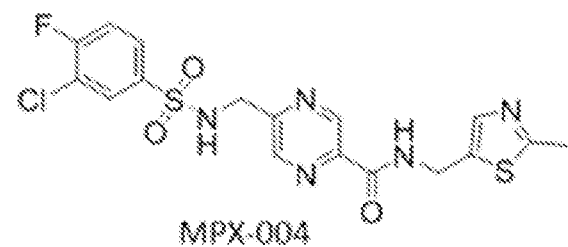

FIG. 23. Chemical structure of MPX-004 5-(((3-chloro-4-fluorophenyl)sulfonamido)methyl)-N-((2-methylthiazol-5-yl)methyl)pyrazine-2-carboxamide.

Figure 24:
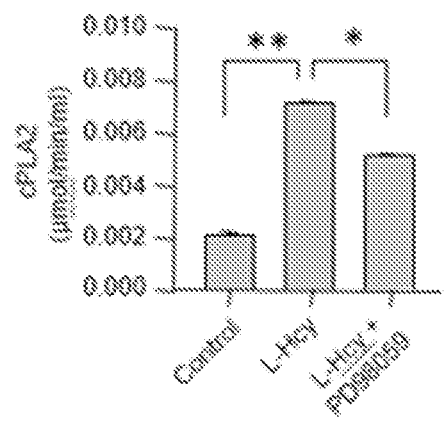
Figure 24:
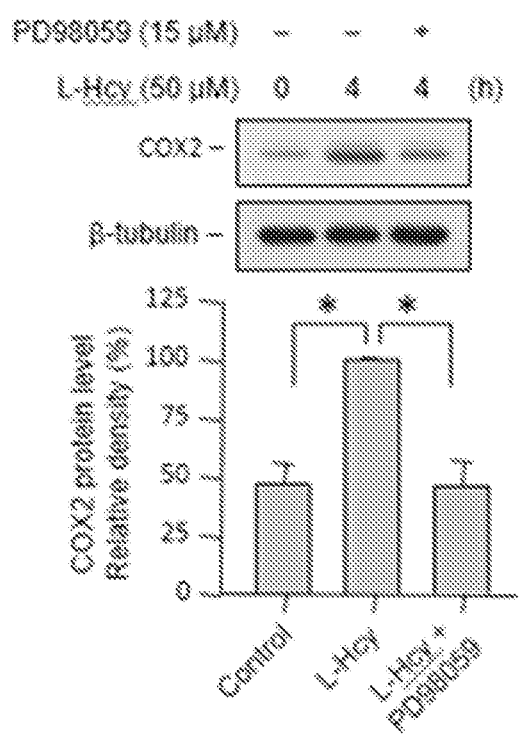
Figure 24:
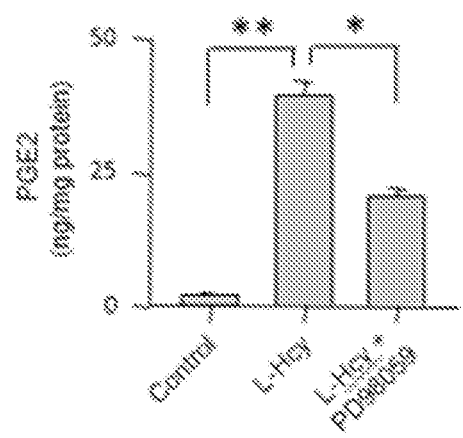

FIG. 24. Role of ERK MAPK in homocysteine-GuN2A-NMDAR dependent activation of cPLA2-COX2-PGE2 pathway in neurons. Rat neuronal cultures were treated with 50 μM L-homocysteine (L-Hcy) for four hours in the absence or presence of PD98059 (15 μM). (A) Equal amounts of protein from cell lysates was analyzed for cPLA2 activity using an enzymatic assay. (B) Immunoblot analysis of equal protein from neuronal lysates using anti-COX2 (upper panel) and β-tubulin (lower panel) antibodies. COX2 protein levels were quantified using computer-assisted densitometry and Image J analysis. (C) Equal amounts of culture media from each sample were analyzed for PGE2 levels using ELISA. Values are represented as mean±SEM (n=5). *p<0.05 and **p<0.0001 from four-hour homocysteine treatment.

Figure 25:
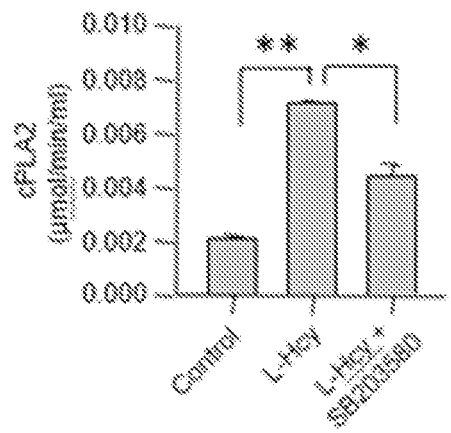
Figure 25:
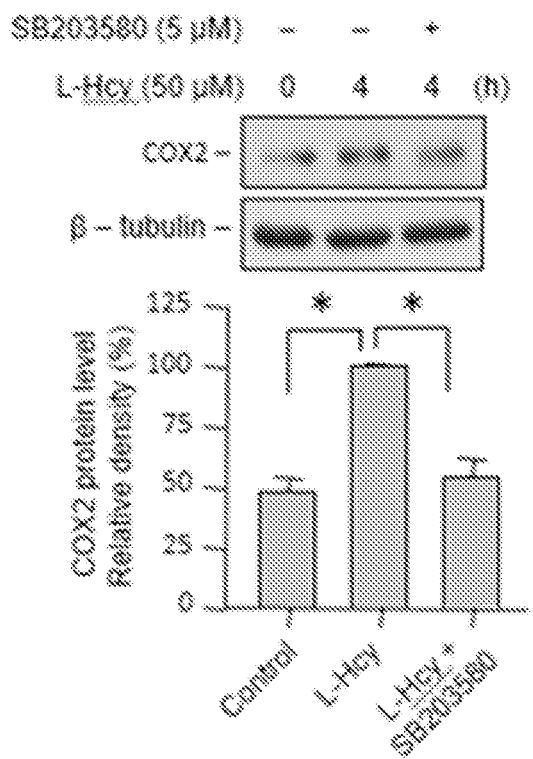
Figure 25:
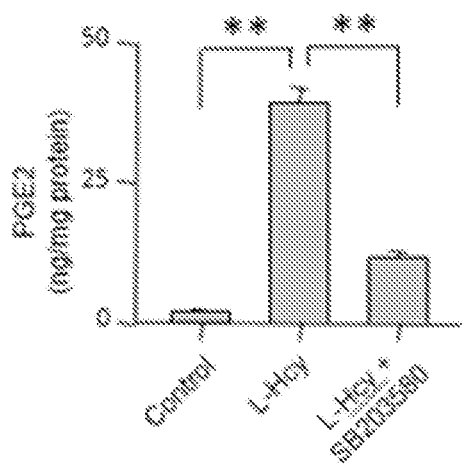

FIG. 25. Role of p38 MAPK in homocysteine-GuN2A-NMDAR dependent activation of cPLA2-COX2-PGE2 pathway in neurons. Rat neuronal cultures were treated with 50 μM L-homocysteine (L-Hcy) for four hours in the absence or presence of SB203580 (5 μM). (A) Equal amounts of protein from cell lysates was analyzed for cPLA2 activity using an enzymatic assay. (B) Immunoblot analysis of equal protein from neuronal lysates using anti-COX2 (upper panel) and β-tubulin (lower panel) antibodies. COX2 protein levels were quantified using computer-assisted densitometry and Image J analysis. (C) Equal amounts of culture media from each sample were analyzed for PGE2 levels using ELISA. Values are represented as mean±SEM (n=5). *p<0.05 and **p<0.0001 from four-hour homocysteine treatment.

Figure 26:
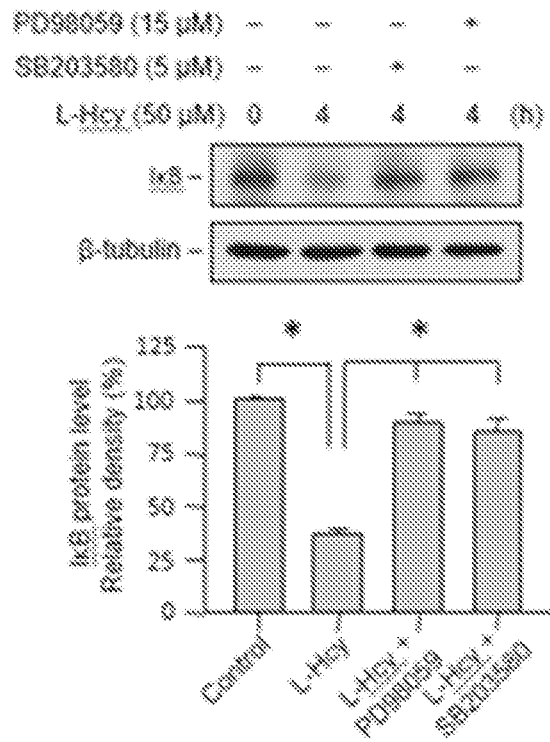
Figure 26:
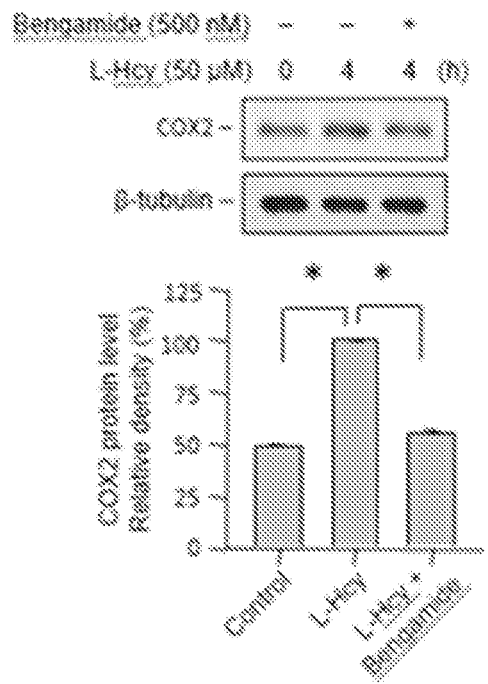
Figure 26:
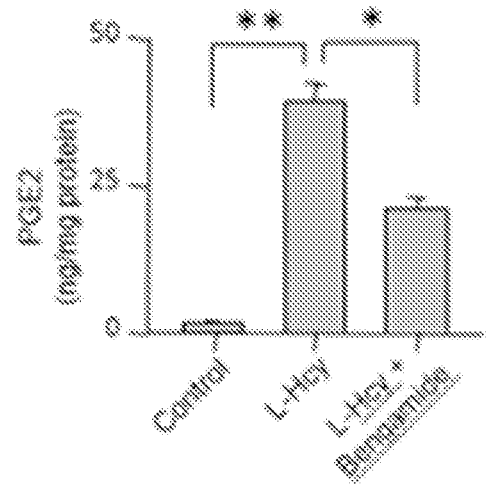
Figure 26:
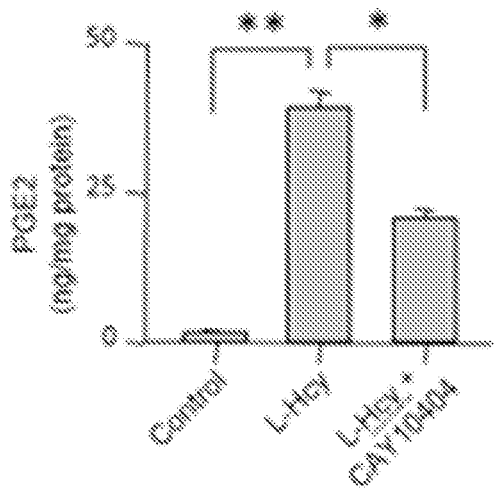

FIG. 26. NFκB regulates ERK-p38 MAPK dependent neuronal PGE2 release. (A) Rat neuronal cultures were treated with 50 μM L-homocysteine (L-Hcy) for four hours in the absence or presence of PD98059 (15 μM) or SB203580 (5 μM). (B) Rat neuronal cultures were treated with 50 μM L-homocysteine (L-Hcy) for four hours in the absence or presence of Bengamide B (500 nM). (C) Rat neuronal cultures were treated with 50 μM L-homocysteine (L-Hcy) for four hours in the absence or presence of Bengamide B (500 nM). (D) Rat neuronal cultures were treated with 50 μM L-homocysteine (L-Hcy) for four hours in the absence or presence of CAY10404 (100 μM). Immunoblot analysis of equal protein from neuronal lysates with anti-IκB ((A), upper panel) and β-tubulin ((A), lower panel) antibodies, or anti-COX2 ((B), upper panel) and β-tubulin ((B), lower panel) antibodies. IκB and COX2 protein levels were quantified using computer-assisted densitometry and Image J analysis. Equal amounts of culture media from each sample were analyzed for PGE2 levels using ELISA (C and D). Values are represented as mean±SEM (n=5). *p<0.001 and **p<0.0001 from four-hour homocysteine treatment.

Figure 27:
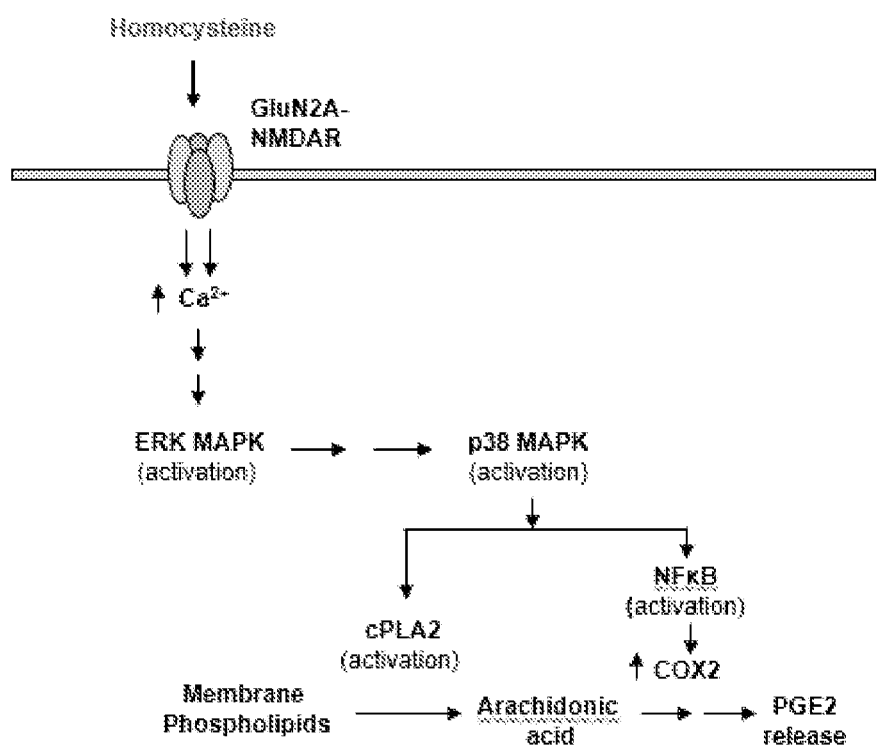

FIG. 27. Schematic representation of the signaling cascade involved in homocysteine induced neuronal PGE2 release. Homocysteine induced GluN2A-NMDAR stimulation leads to sequential activation of ERK and p38 MAPKs resulting in concomitant increase in cPLA2 and NFκB activity that eventually leads to COX2 mediated PGE2 biosynthesis and release from neurons.

Figure 28:
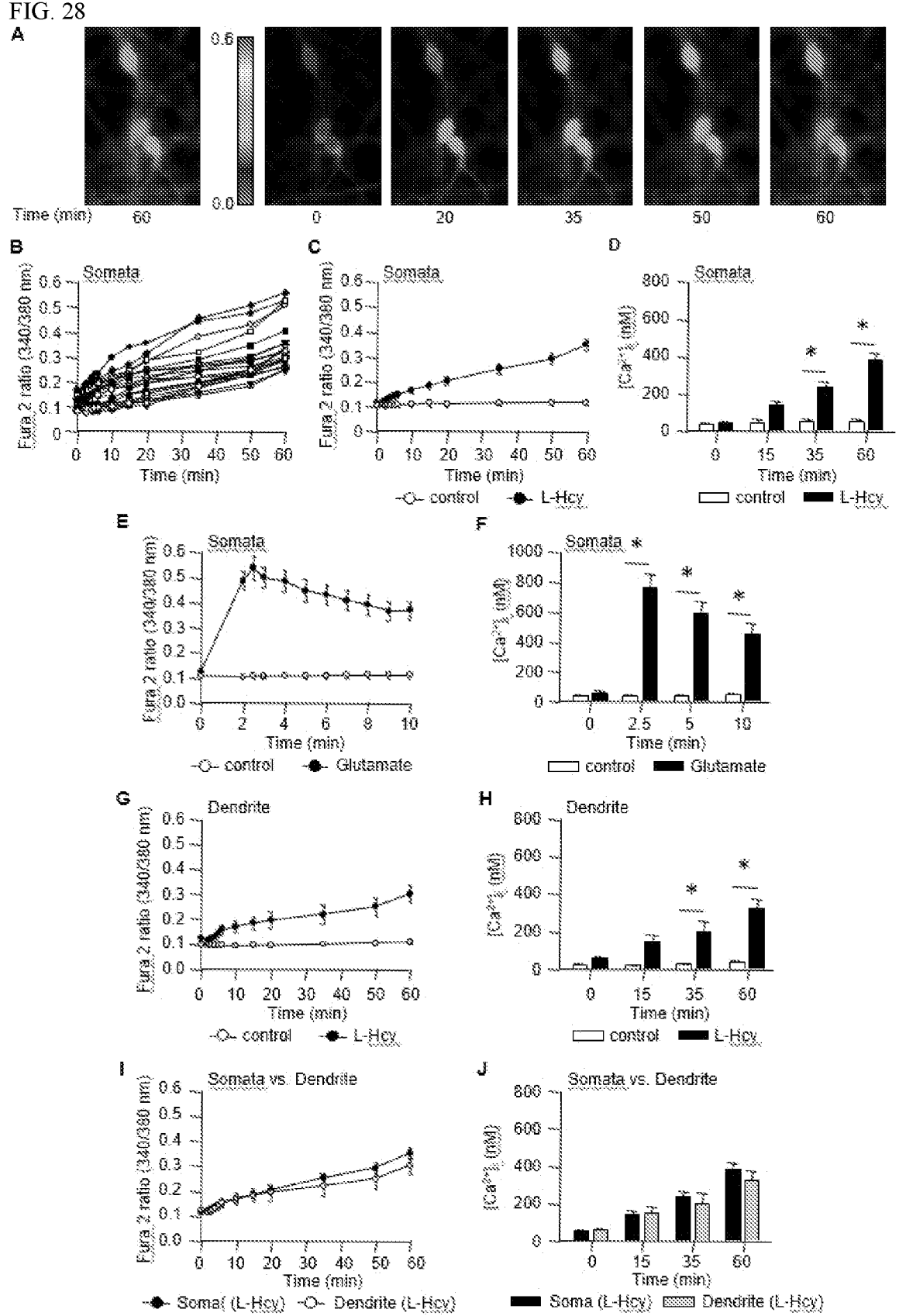

FIG. 28. Time course of homocysteine and glutamate induced changes in $[Ca^{2+}]_i$ neurons. (A) Representative micrographs of neurons showing $[Ca^{2+}]_i$ changes over time measured with Fura2 following exposure to L-homocysteine (50 μM). Both black and white (60 min) and false color images (0-60 min) are shown. (B) Individual responses in soma of 20 neurons showing the range of increase in Fura2 fluorescence ratio over time following exposure to L-homocysteine (L-Hcy). (C) Temporal profile of increase in Fura2 fluorescent ratio in L-Hcy-treated and untreated cells (control). Values are mean±SEM (n=17-20). (D) Temporal profile of increase in $[Ca^{2+}]_i$ in L-Hcy-treated and untreated cells (control). Values are mean±SEM (n=17-20). (E) Temporal profile of increase in Fura2 fluorescent ratio in glutamate (50 μM)-treated and control cells. Values are mean±SEM (n=17-20). (F) Temporal profile of increase in $[Ca^{2+}]_i$ in glutamate (50 μM)-treated and control cells. Values are mean±SEM (n=17-20). (G) Time-dependent changes in Fura2 fluorescence ratio in dendrites of L-Hcy-treated and control cells. Values are mean±SEM (n=10-13). (H) Time-dependent changes in $[Ca^{2+}]_i$ in dendrites of L-Hcy-treated and control cells. Values are mean±SEM (n=10-13). (I) Comparison of changes in Fura2 fluorescence ratio between soma and dendrites of L-Hcy-treated cells. Values are mean±SEM (n=13-20 cells). *p<0.0001 and #p<0.01 from control cells at the given time point. (J) Comparison of changes in $[Ca^{2+}]_i$ between soma and dendrites of L-Hcy-treated cells. Values are mean±SEM (n=13-20 cells). *p<0.0001 and #p<0.01 from control cells at the given time point.

Figure 29:
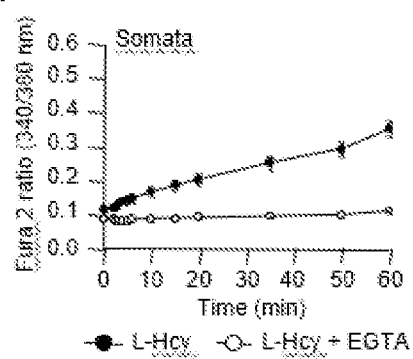
Figure 29:
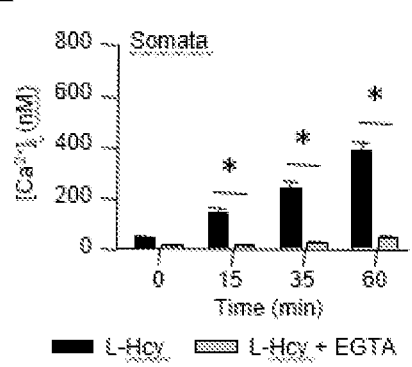
Figure 29:
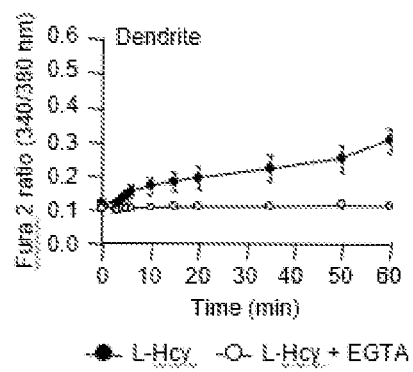
Figure 29:
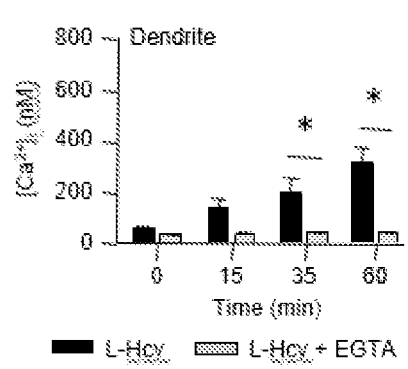
Figure 29:
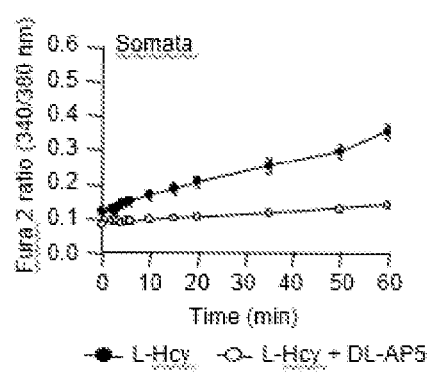
Figure 29:
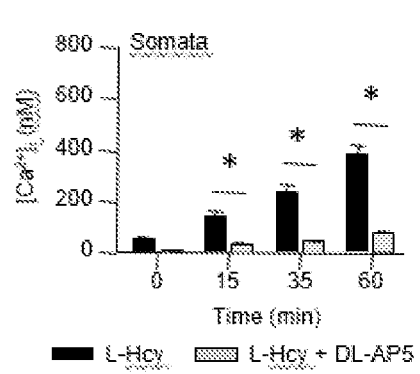
Figure 29:
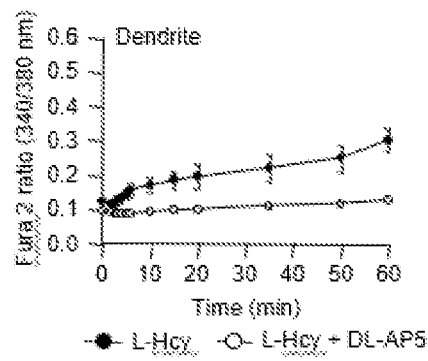
Figure 29:
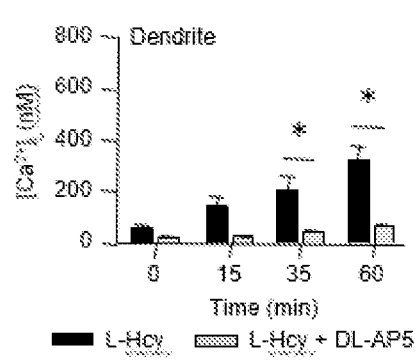

FIG. 29. Homocysteine-induced $Ca^{2+}$ influx is NMDAR-dependent. (A) Changes in Fura2 fluorescent ratio in somata of cells treated with L-Hcy (50 μM) in the presence or absence of EGTA (2 mM). (B) Changes in $[Ca^{2+}]_i$ in somata of cells treated with L-Hcy (50 μM) in the presence or absence of EGTA (2 mM). (C) Changes in Fura2 fluorescent ratio in dendrites of cells treated with L-Hcy (50 μM) in the presence or absence of EGTA (2 mM). (D) Changes in $[Ca^{2+}]_i$ in dendrites of cells treated with L-Hcy (50 μM) in the presence or absence of EGTA (2 mM). (E) Changes in Fura2 fluorescent ratio in somata of cells treated with L-Hcy (50 μM) in the presence or absence of DL-AP5 (200 μM). Values are mean±SEM (n=10-20 cells). *p<0.001 from control cells at the given time point. (F) Changes in $[Ca^{2+}]_i$ in somata of cells treated with L-Hcy (50 μM) in the presence or absence of DL-AP5 (200 μM). Values are mean±SEM (n=10-20 cells). *p<0.001 from control cells at the given time point. (G) Changes in Fura2 fluorescent ratio in dendrites of cells treated with L-Hcy (50 μM) in the presence or absence of DL-AP5 (200 μM). Values are mean±SEM (n=10-20 cells). *p<0.001 from control cells at the given time point. (H) Changes in $[Ca^{2+}]_i$ in dendrites of cells treated with L-Hcy (50 μM) in the presence or absence of DL-AP5 (200 μM). Values are mean±SEM (n=10-20 cells). *p<0.001 from control cells at the given time point.

Figure 30:
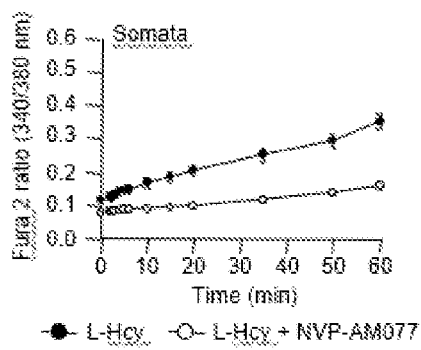
Figure 30:
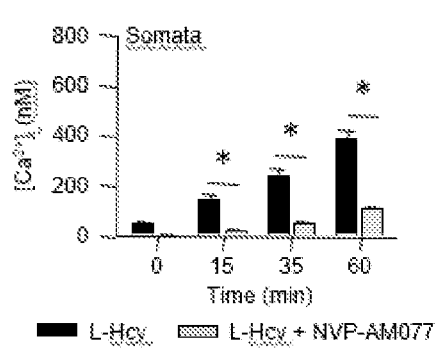
Figure 30:
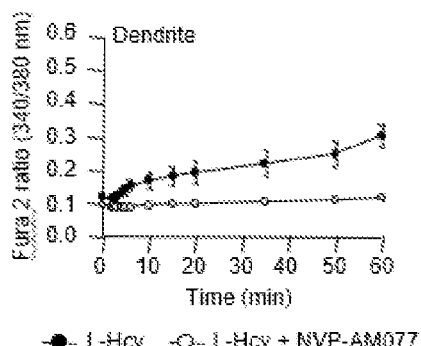
Figure 30:
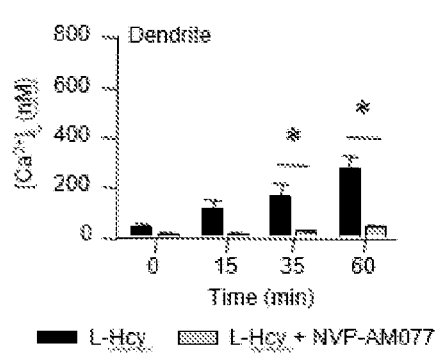
Figure 30:
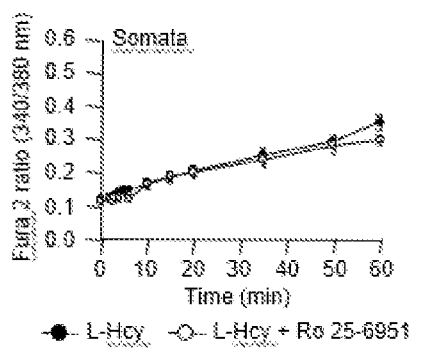
Figure 30:
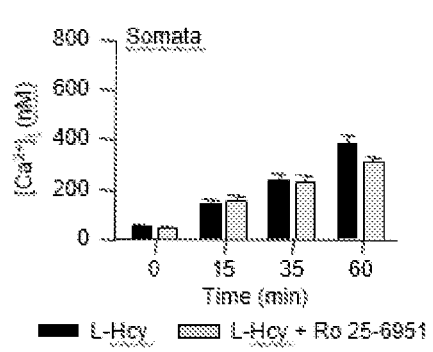
Figure 30:
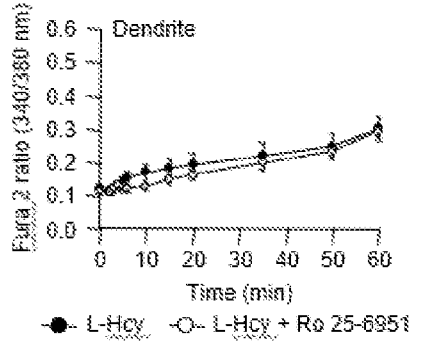
Figure 30:
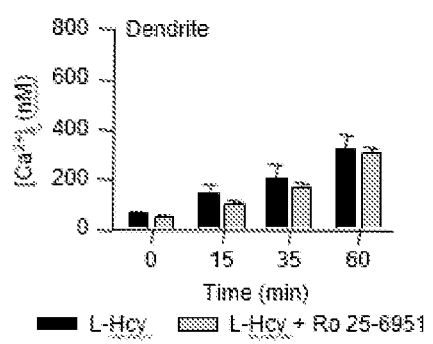

FIG. 30. Pharmacological inhibition of GluN2A-NMDAR attenuates homocysteine-induced $Ca^{2+}$ influx. (A) Changes in Fura2 fluorescent ratio in somata of cells treated with L-Hcy (50 μM) in the presence or absence of NVP-AAM077 (30 nM). (B) Changes in $[Ca^{2+}]_i$ in somata of cells treated with L-Hcy (50 μM) in the presence or absence of NVP-AAM077 (30 nM). (C) Changes in Fura2 fluorescent ratio in dendrites of cells treated with L-Hcy (50 μM) in the presence or absence of NVP-AAM077 (30 nM). (D) Changes in $[Ca^{2+}]_i$ in dendrites of cells treated with L-Hcy (50 μM) in the presence or absence of NVP-AAM077 (30 nM). (E) Changes in Fura2 fluorescent ratio in somata of cells treated with L-Hcy (50 μM) in the presence or absence of Ro 25 6981 (1 μM). (F) Changes in $[Ca^{2+}]_i$ in somata of cells treated with L-Hcy (50 μM) in the presence or absence of Ro 25 6981 (1 μM). (G) Changes in Fura2 fluorescent ratio in dendrites of cells treated with L-Hcy (50 μM) in the presence or absence of Ro 25 6981 (1 μM). (H) Changes in $[Ca^{2+}]_i$ in dendrites of cells treated with L-Hcy (50 μM) in the presence or absence of Ro 25 6981 (1 μM). Values are mean±SEM (n=10-20 cells). *p<0.001 from control cells at the given time point.

Figure 31:
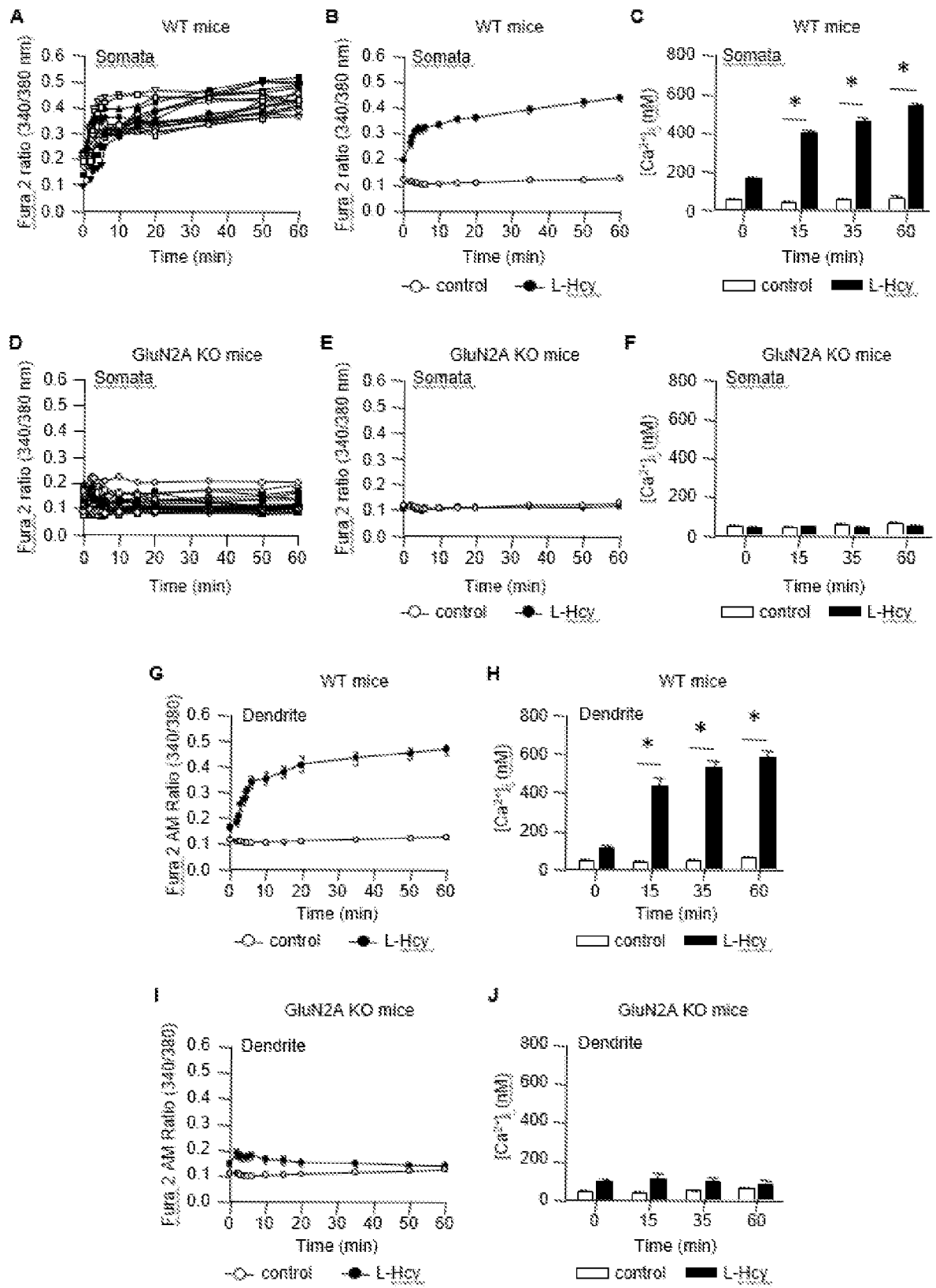

FIG. 31. Knockdown of GluN2A subunit blocks homocysteine-induced $Ca^{2+}$ influx. (A) Individual responses in soma of 16-18 neurons obtained from WT mice showing the range of increase in Fura2 fluorescence ratio over time following exposure to L-homocysteine (L-Hcy, 50 μM). (B) Temporal profile of increase in Fura2 fluorescent ratio in the somata of L-Hcy-treated and control cells from WT mice. (C) Temporal profile of increase in $[Ca^{2+}]_i$ in the somata of L-Hcy-treated and control cells from WT mice. (D) Individual responses in soma of 16-18 neurons obtained from GluN2A KO mice showing the range of increase in Fura2 fluorescence ratio over time following exposure to L-homocysteine (L-Hcy, 50 µM). (E) Temporal profile of increase in Fura2 fluorescent ratio in the somata of L-Hcy-treated and control cells from GluN2A KO mice. (F) Temporal profile of increase in $[Ca^{2+}]_i$ in the somata of L-Hcy-treated and control cells from GluN2A KO mice. (G) Temporal profile of increase in Fura2 fluorescent ratio in dendrites of L-Hcy-treated and control cells from WT mice. (H) Temporal profile of increase in $[Ca^{2+}]_i$ in dendrites of L-Hcy-treated and control cells from WT mice. (I) Temporal profile of increase in Fura2 fluorescent ratio in dendrites of L-Hcy-treated and control cells from GluN2A KO mice. (J) Temporal profile of increase in $[Ca^{2+}]_i$ in dendrites of L-Hcy-treated and control cells from GluN2A KO mice. Values are mean±SEM. *p<0.0001 from control cells at the given time point.

Figure 32:
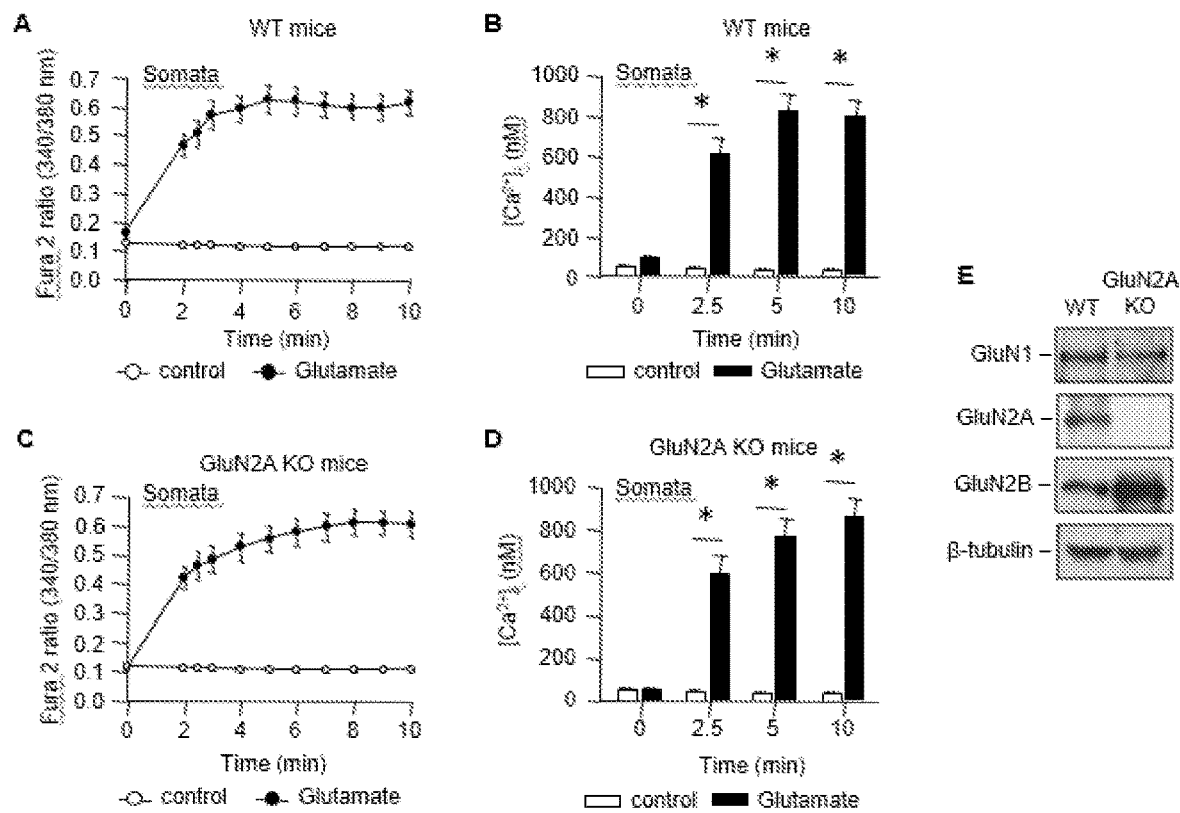

FIG. 32. Knockdown of GluN2A subunit does not affect glutamate-induced $Ca^{2+}$ influx. (A) Temporal profile of increase in Fura2 fluorescent ratio in the somata of glutamate (50 µM)-treated and control cells from WT mice. (B) Temporal profile of increase in $[Ca^{2+}]_i$ in the somata of glutamate (50 µM)-treated and control cells from WT mice. (C) Temporal profile of increase in Fura2 fluorescent ratio in the somata of glutamate (50 µM)-treated and control cells from GluN2A KO mice. (D) Temporal profile of increase in $[Ca^{2+}]_i$ in the somata of glutamate (50 µM)-treated and control cells from GluN2A KO mice. Values are mean±SEM. *p<0.0001 from control cells at the given time point. (E) Immunoblot analysis of neuronal lysates from WT and GluN2A-KO mice with anti-GuN1, anti-GuN2A, anti-GuN2B and anti-β-tubulin antibodies.

Figure 33:
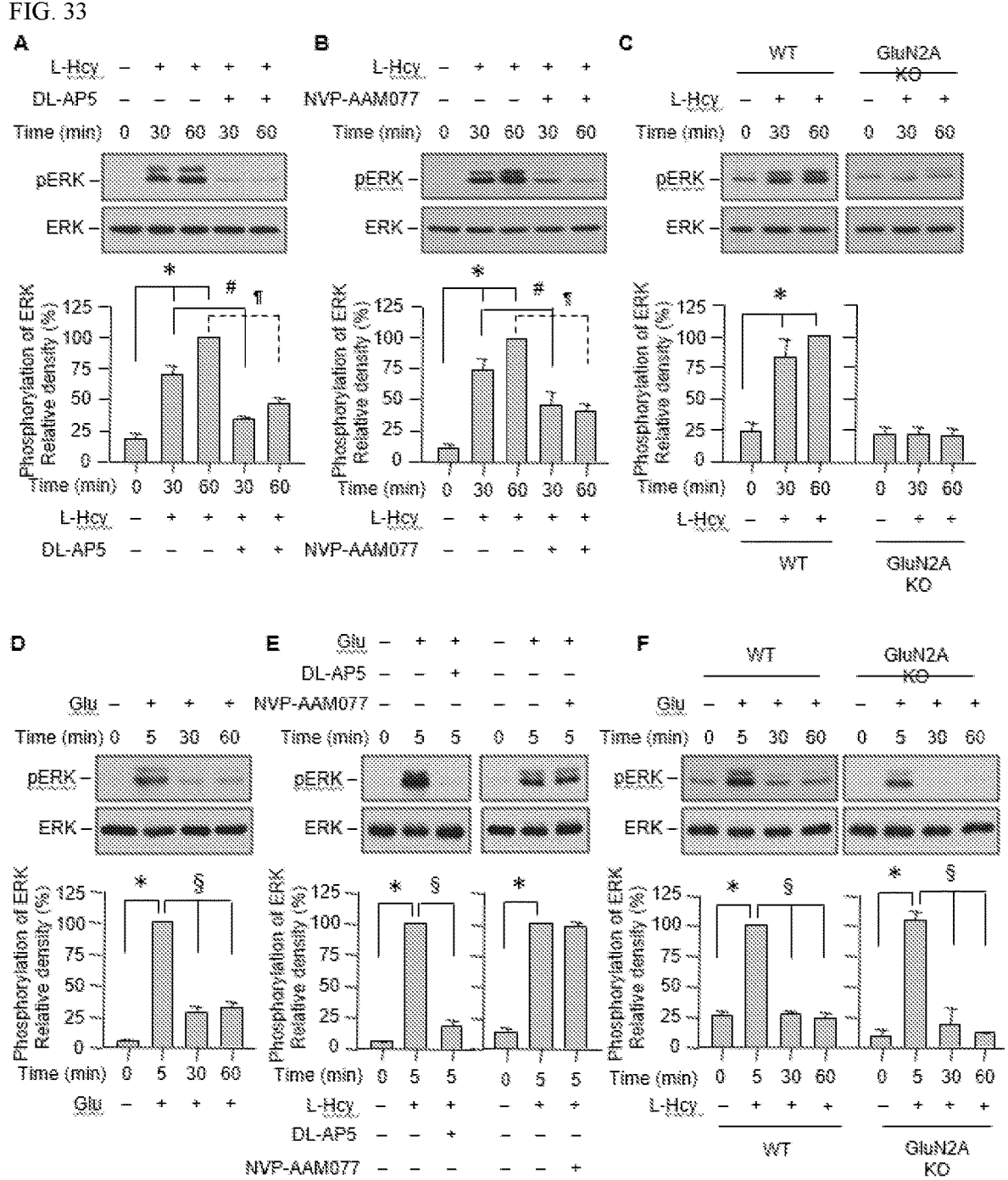

FIG. 33. Homocysteine-induced ERK MAPK phosphorylation is mediated through GluN2A-NMDAR. (A) Rat neuron cultures were exposed to L-Hcy (50 µM) for 30 minutes or 60 minutes in the absence and presence of DL-AP5 (200 µM). (B) Rat neuron cultures were exposed to L-Hcy (50 µM) for 30 minutes or 60 minutes in the absence and presence of NVP-AAM077 (30 nM). (C) Neuronal cultures from WT and GluN2A KO mice were treated with L-Hcy (50 µM) for 30 minutes or 60 minutes. (D) Rat neuron cultures were exposed to glutamate (50 µM) for five minutes, 30 minutes, or 60 minutes. (E) Rat neuronal cultures were exposed to glutamate for five minutes in the presence or absence of DL-AP5 (200 µM) or NVP-AAM077 (30 nM). (F) Neuronal cultures from WT and GluN2A KO mice were treated with glutamate (50 µM) for five minutes, 30 minutes, or 60 minutes. Immunoblot analysis of cell lysates with anti-phospho-ERK (top) and anti-ERK (bottom) antibodies. Values are mean±SEM (n=5). *p<0.001 from corresponding 0 minutes, #p<0.001 from 30 minutes L-Hcy treatment, ¶p<0.001 from 60 minutes L-Hcy treatment and § p<0.0001 from five minutes glutamate treatment.

Figure 34:
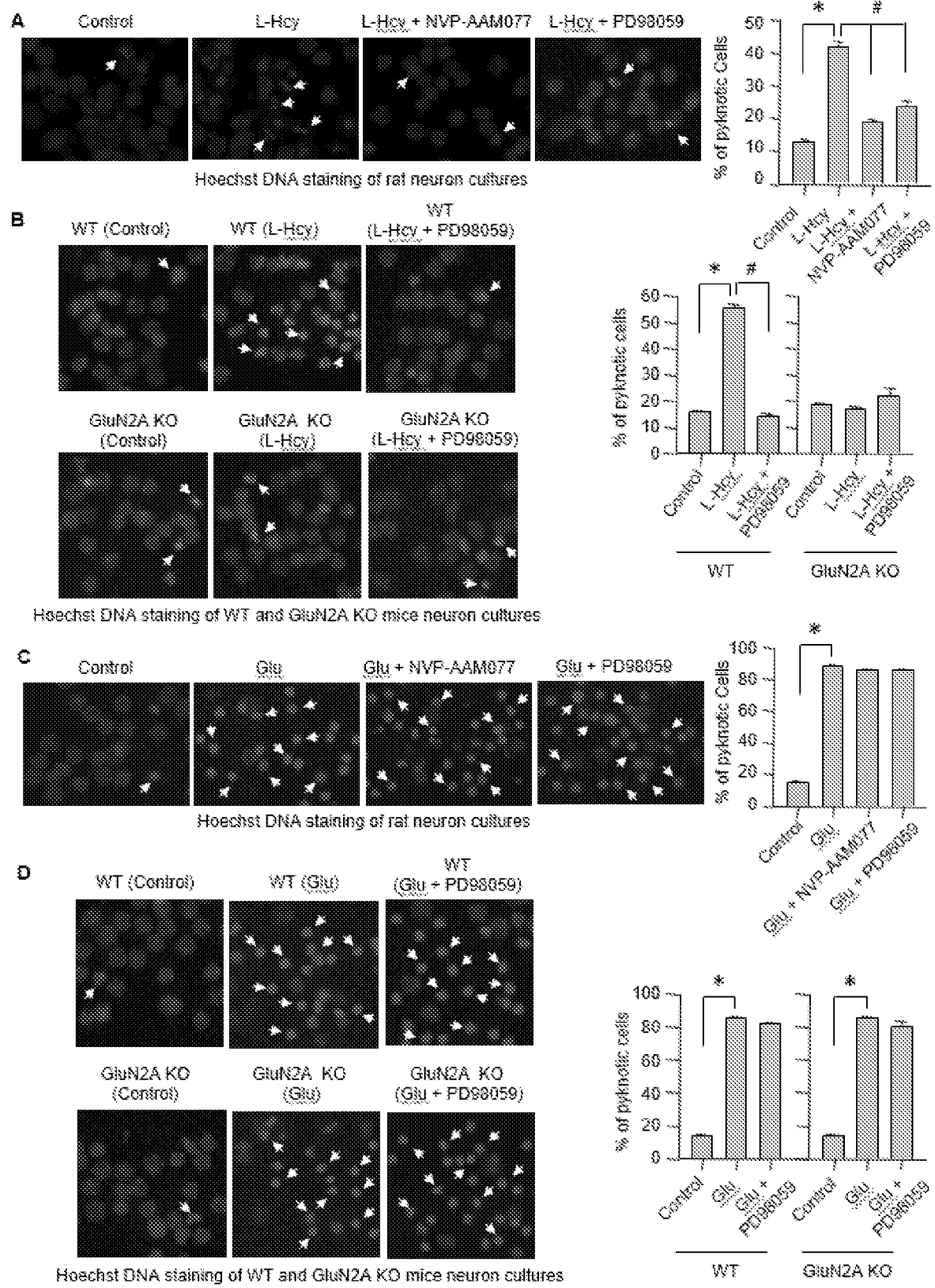

FIG. 34. Homocysteine-induced neurotoxicity is mediated through GuN2A-NMDAR dependent ERK MAPK activation. (A) Rat neuronal cultures were exposed to L-Hcy (50 µM, 18 hours) in the absence and presence of NVP-AAM077 (30 nM) or PD98059 (15 µM). (B) Neurons from WT and GluN2A KO mice were exposed to L-Hcy (50 µM, 18 hours) in the absence or presence of PD98059 (15 µM). (C) Rat neuronal cultures were exposed to glutamate (50 µM, one hour) in the absence and presence of NVP-AAM077 (30 nM) or PD98059 (15 µM) and then maintained in original medium for 17 hours. (D) Neurons from WT and GluN2A KO mice were exposed to glutamate (50 µM, one hour) in the absence or presence of PD98059 (15 µM) and then maintained in original medium for 17 hours. Representative photomicrographs showing pyknotic DNA stained with Hoechst 33342 (indicated with arrows). Percentage of neurons with pyknotic nuclei is represented as mean±SEM (n=1500 cells/condition from four experiments). *p<0.001 from corresponding control and #p<0.001 from L-Hcy treatment.

Figure 35:
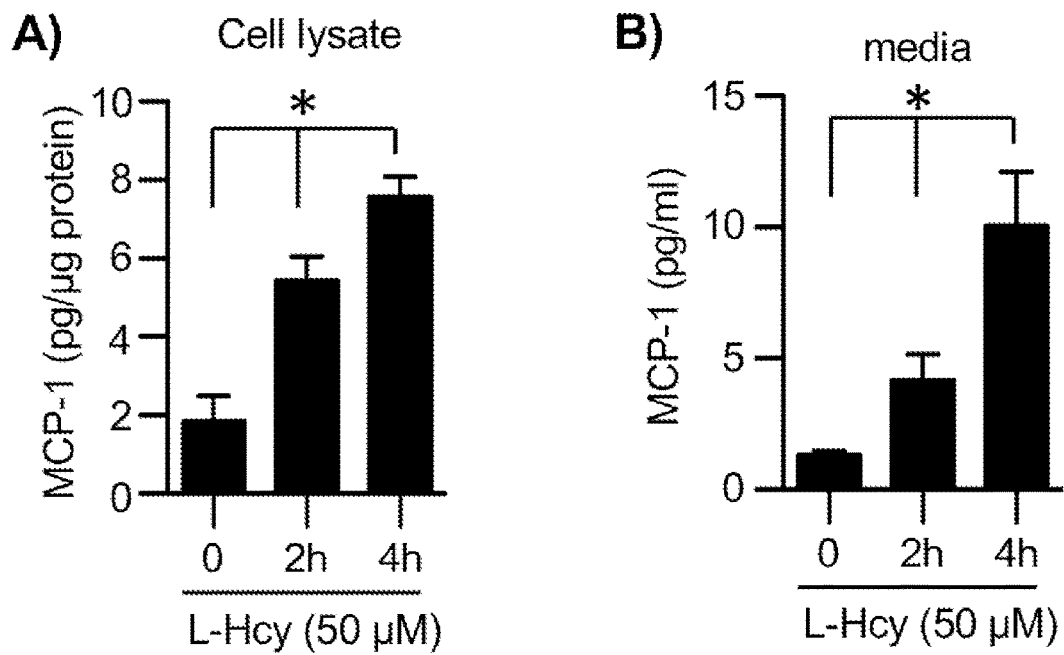

FIG. 35. Homocysteine-induces MCP1 expression and release from neurons. Neuron cultures were treated with 50 µM L-homocysteine (L-Hcy) for 0 hours, two hours, and four hours. (A) Protein cell extract prepared in PBS was analyzed using enzyme immunoassay to estimate the level of chemokine Monocyte Chemoattractant Protein-1 (MCP-1). (B) Culture media was analyzed using enzyme immunoassay to estimate the level of chemokine Monocyte Chemoattractant Protein-1 (MCP-1). Values are represented as mean±SEM (n=3). *p<0.05 compared to control and #p<0.05 compared to L-Hcy treatment.

Figure 36:
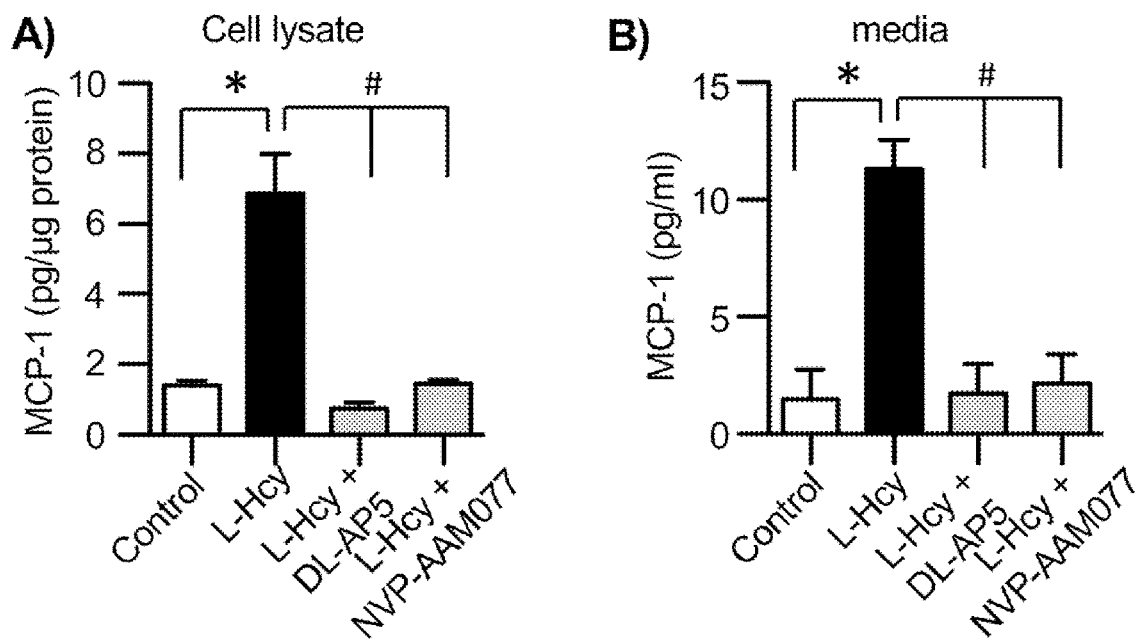

FIG. 36. Homocysteine-induced neuronal MCP-1 is GluN2A-NMDAR-dependent. Neuron cultures were treated with 50 µM L-homocysteine (L-Hcy) for four hours in the absence and presence of DL-AP5 (200 µM) and NVP-AAM077 (30 nM). (A) Protein cell extract was analyzed using enzyme immunoassay to estimate the level of MCP-1. (B) Culture media was analyzed using enzyme immunoassay to estimate the level of MCP-1. Values are represented as mean±SEM (n=3). *p<0.05 compared to control and p<0.05 compared to L-Hcy treatment.

Figure 37:
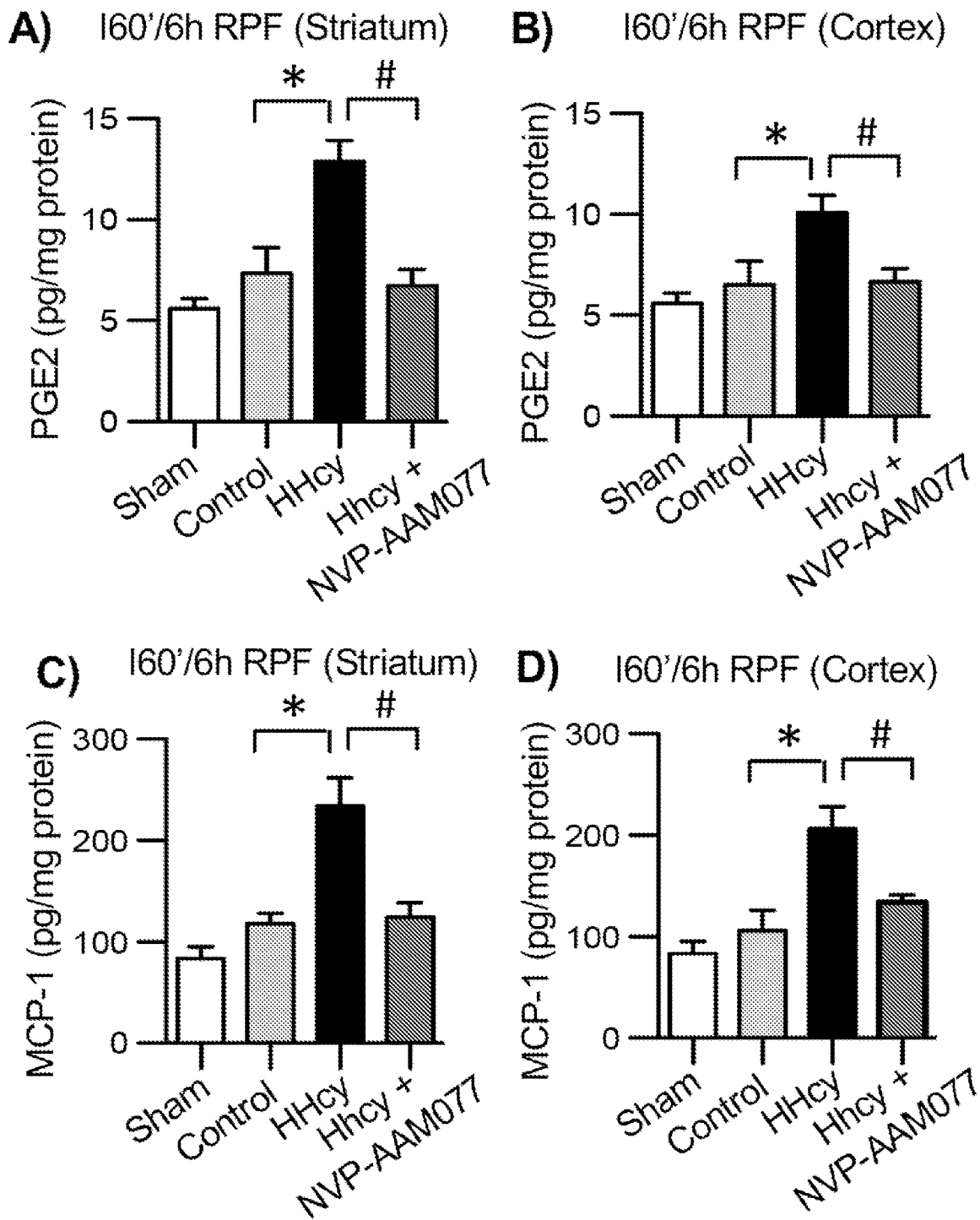

FIG. 37. Hyperhomocysteinemia increases MCP-1 and PGE2 in post-ischemic brain. Control and hyperhomocysteinemic (HHcy) rats were subjected to MCAO (60 minutes) and six hours of reperfusion. (A) Level of PGE2 was measured by enzyme immunoassay in striatum. (B) Level of PGE2 was measured by enzyme immunoassay in cortex. (C) Level of MCP-1 was measured by enzyme immunoassay in striatum. (D) Level of MCP-1 was measured by enzyme immunoassay in cortex. (n=3); *p<0.05 compared to control; #p<0.05 compared to HHcy.

DETAILED DESCRIPTION OF ILLUSTRATIVE EMBODIMENTS

This disclosure describes compositions and method for treating hyperhomocysteinemic subjects having cerebral ischemic stroke. Generally, the method involves administering to a hyperhomocysteinemic subject having cerebral ischemic stroke a composition that includes an inhibitor of a GluN2A-containing NMDAR (N-methyl-D-aspartate receptor) in an amount to ameliorate at least one symptom or clinical sign of cerebral ischemic stroke.

Hyperhomocysteinemia has been implicated in several neurodegenerative disorders including ischemic stroke. However, the pathological consequences of ischemic insult in individuals predisposed to hyperhomocysteinemia and the associated etiology are unknown. In one aspect, this disclosure evaluates the outcome of transient ischemic stroke in a rodent model of mild hyperhomocysteinemia, developed by subcutaneous implantation of osmotic pumps containing L-homocysteine into male Wistar rats. Ischemic stroke leads to a 42.3% mortality rate in hyperhomocysteinemic rats as compared to 7.7% in control rats. Magnetic resonance imaging of the brain in the surviving rats shows that mild hyperhomocysteinemia leads to exacerbation of ischemic brain injury within 24 hours, which remains elevated over time. Behavioral studies further demonstrate significant deficit in sensorimotor functions in hyperhomocysteinemic rats when compared to control rats.

In another aspect, this disclosure evaluates whether treatment with homocysteine triggers the release of proinflammatory mediators from neurons. Treatment of cortical neuron cultures with homocysteine leads to a time-dependent increase in the release of the pro-inflammatory prostanoid, Prostaglandin E2 (PGE2) from neurons that reaches significantly high levels within one hour. A corresponding increase in the activity of $Ca^{2+}$-dependent enzyme phospholipase A2 (cPLA2) that is involved in the production of arachidonic acid, and increase in the level of cyclooxygenase-2 (COX2) that catalyzes the conversion of arachidonic acid into PGE2 are also observed in these homocysteine-treated neurons. Selective inhibition of GluN2A-subtype of NMDAR (GluN2A-NMDAR) significantly attenuated the homocysteine-mediated increase in COX2 expression and cPLA2 activity as well as the subsequent release of PGE2 from neurons. Complementary studies with cortical neuron cultures from wild type and GluN2A-NMDAR knockout mice show that homocysteine exposure failed to enhance COX2 expression in the knockout mice, confirming the role of GluN2A-NMDAR in homocysteine-induced neuroinflammatory response. Pharmacological inhibition of ERK or p38 MAPK, where p38 MAPK is shown to be downstream of ERK MAPK in homocysteine-signaling pathway, also reduced the homocysteine-induced COX2 expression, cPLA2 activity and PGE2 release. The disclosure therefore not only reveals that homocysteine triggers proinflammatory response but also provides a novel mechanism highlighting the role of GluN2A-NMDAR-mediated crosstalk between ERK and p38 MAPK in promoting inflammation.

Treatment of cortical neuron cultures with homocysteine also leads to a time-dependent increase in the expression and release of the pro-inflammatory chemokine, monocyte chemoattractant protein-1 (MCP-1) from neurons that reaches significantly high levels within two hours. Selective inhibition of GluN2A-GuN2A-NMDAR significantly attenuated the homocysteine-mediated increase in MCP-1 expression and release from neurons.

In vivo studies in control and hyperhomocysteinemic rats (MCAO 60 minutes followed by reperfusion for six hours) further shows significant increase in both MCP-1 and PGE2 levels in the ischemic hemisphere (striatum and cortex) of hyperhomocysteinemic rats. Inhibition of GluN2A-NMDAR attenuated the increase in MCP-1 and PGE2 levels.

Ischemic Stroke

Using pharmacological inhibitors targeting the NMDAR subtypes, this disclosure demonstrates that inhibiting GluN2A-containing NMDARs significantly reduces ischemic brain damage in hyperhomocysteinemic rats but not in control rats, indicating that hyperhomocysteinemia-mediated exacerbation of ischemic brain injury involves GluN2A-NMDAR signaling. Complementary studies in GluN2A-knockout mice show that hyperhomocysteinemia-associated exacerbation of ischemic brain injury is blocked in the absence of GluN2A-NMDARs, confirming that GluN2A-NMDAR activation influences the severity of ischemic damage under hyperhomocysteinemic conditions. Taken together, the findings show that hyperhomocysteinemia triggers unique signaling pathways that in conjunction with ischemia-induced pathways enhance the pathology of stroke under hyperhomocysteinemic conditions. In addition, this in vivo study provides the first evidence for a pathological role of GluN2A-NMDARs, leading to a major paradigm shift in the field of NMDAR signaling.

Establishment of a Mild Hyperhomocysteinemic Rat Model

Figure 1:
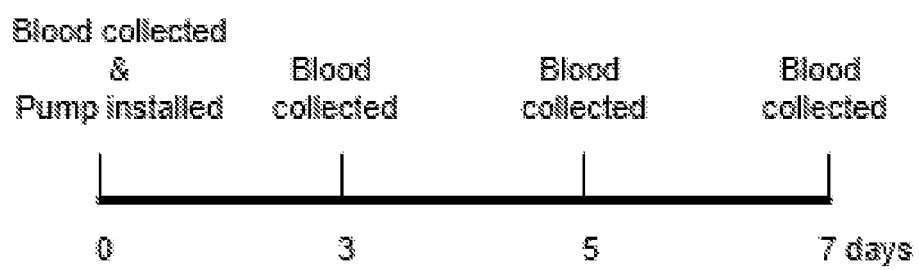
FIG. 1. Evaluation of total plasma homocysteine levels in hyperhomocysteinemic rats by HPLC. (A) Schematic representation of the timeline of implantation of saline or homocysteine containing osmotic pumps and blood collection. (B) Quantitative analysis of total plasma homocysteine levels in rats implanted with saline (control) or homocysteine (HHcy) pumps, before (0 day) and after (3, 5 and 7 days) pump implantation. Values expressed as mean±SEM (control: n=4-9, HHcy: n=7-10). *$p<0.0001$ for control vs. HHcy rats.
Figure 1:
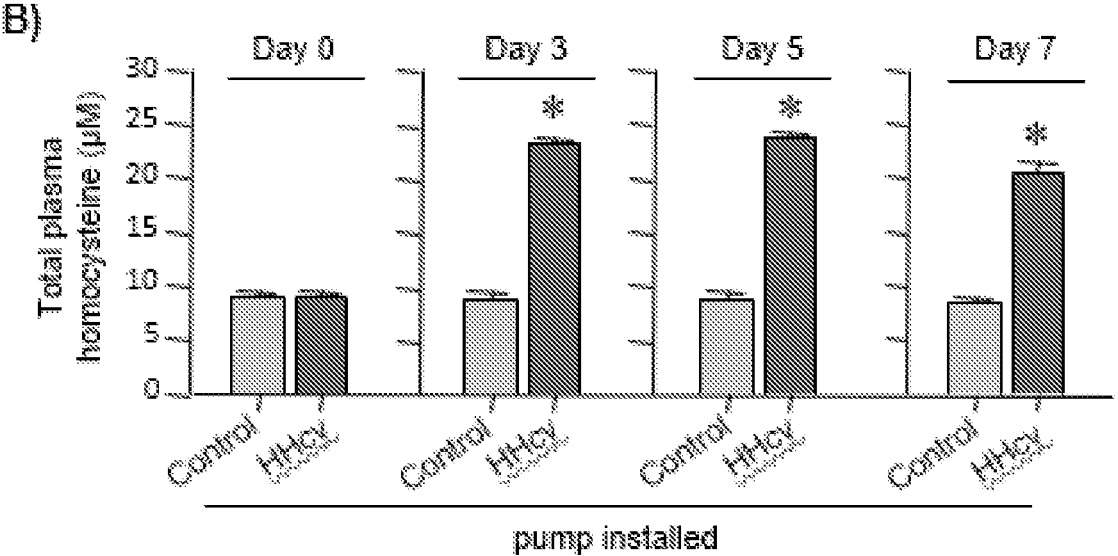

In initial studies, male Wistar rats were made hyperhomocysteinemic by subcutaneous implantation of osmotic pumps containing 200 mM L-homocysteine. For control rats, the osmotic pump contained saline. Total plasma homocysteine levels were analyzed from blood obtained from hyperhomocysteinemic (HHcy) and control rats at different time intervals (FIG. 1A). FIG. 1B shows that basal level of total plasma homocysteine in rats is 8.8±0.76 µM prior to pump implantation. This basal level does not change significantly in the control rats with the installation of saline containing pumps. However, installation of L-homocysteine containing pumps increases total plasma homocysteine level to 23.2±0.52 µM ($p<0.0001$; $r=0.969$) within 3 days that remains sustained for the time period of the study (day 5: 23.57±0.57 µM; $p<0.0001$; $r=0.9663$, day 7: 20.52±0.88; $p<0.0001$, $r=0.954$).

Hyperhomocysteinemia Exacerbates Ischemic Brain Injury in Rats

In subsequent experiments, rats with normal (control) and elevated levels of homocysteine (hyperhomocysteinemic) were subjected to either sham surgery or MCAO for 60 min, 4 days after pump implantation, followed by reperfusion and assessment of infarct size and functional outcome, as outlined in FIG. 2A. Ischemic insult under hyperhomocysteinemic (HHcy) condition increases the mortality rate substantially when compared with the control group (FIG. 2B; control: 7.69% vs. HHcy: 42.3%). Evaluation of the extent of brain injury in the surviving animals at 24 hours after the insult using MRI show regions of increased T2 signal intensity in the stroked hemisphere of both control and hyperhomocysteinemic rats indicating ischemic lesion (FIG. 2C, compare T2 maps from control MCAO and hyperhomocysteinemic MCAO group). FIG. 2C further show that hyperhomocysteinemia by itself does not cause any brain lesion in the absence of an ischemic insult (compare control sham vs. hyperhomocysteinemic sham). Quantitative analysis of lesion volume in control and hyperhomocysteinemic rats subjected to MCAO (FIG. 2D) shows a significant increase in infarct size under hyperhomocysteinemic condition (control: 18.36±2.85% vs. HHcy: 37.41±2.33%; $p<0.0001$, $r=0.716$).

Long-Term Progression of Ischemic Damage in Hyperhomocysteinemic Rats

Longitudinal evaluation of ischemic lesion volume in control and hyperhomocysteinemic rats up to 14 days post-MCAO show significant group effect [$F_{(1, 22)}=26.39$, $p<0.0001$] and day effect [$F_{(2, 44)}=17.702$, $p<0.0001$] between the two groups. However, treatment by day interaction is not significant. The representative T2 maps and quantitative measurement of lesion volume from the T2 maps (FIG. 3A) show that the infarct size remains significantly higher in the hyperhomocysteinemic rats at both day 3 (control: 21.94±2.74% vs. HHcy: 38.63±2.75%) and day 14 (control: 13.81±2.77% vs. HHcy: 27.16±2.18%) after MCAO. To assess the structural integrity of the tissue in the damaged area of the ischemic brain, changes in ADC and FA values were evaluated at 14-day post-MCAO. The representative ADC and FA maps and the quantitative analysis of ADC and FA values show a significant increase in the ADC value (control: $1.01 \times 10^3 \pm 0.01 \times 10^3$ $mm^2/sec$ vs. HHcy: $1.41 \times 10^3 \pm 0.06 \times 10^3$ $mm^2/sec$; $p=0.002$; $r=0.587$) with a concomitant decrease in FA value (control: 0.3±0.02 vs. HHcy: 0.25±0.01; $p=0.049$; $r=0.405$) in the hyperhomocysteinemic rats (FIGS. 3B and C). This pattern of increased mean diffusion with decreased directional diffusion as observed from the ADC and FA data respectively suggests that an ischemic insult under hyperhomocysteinemic condition accelerates tissue breakdown resulting in greater loss of structural integrity and orientation of the brain tissue in the infarcted area. For histopathological confirmation of the ischemic lesion observed using MRI at 14-day post-MCAO brain sections from both control and hyperhomocysteinemic rats were processed for cresyl violet staining. The representative photomicrographs presented in FIG. 3D shows that the characteristic pattern of lesion observed by cresyl violet staining is comparable to the ischemic lesion detectable in T2 maps (FIG. 3A). These data support the feasibility of the non-invasive MRI approach for quantitation of lesion size.

Figure 4:
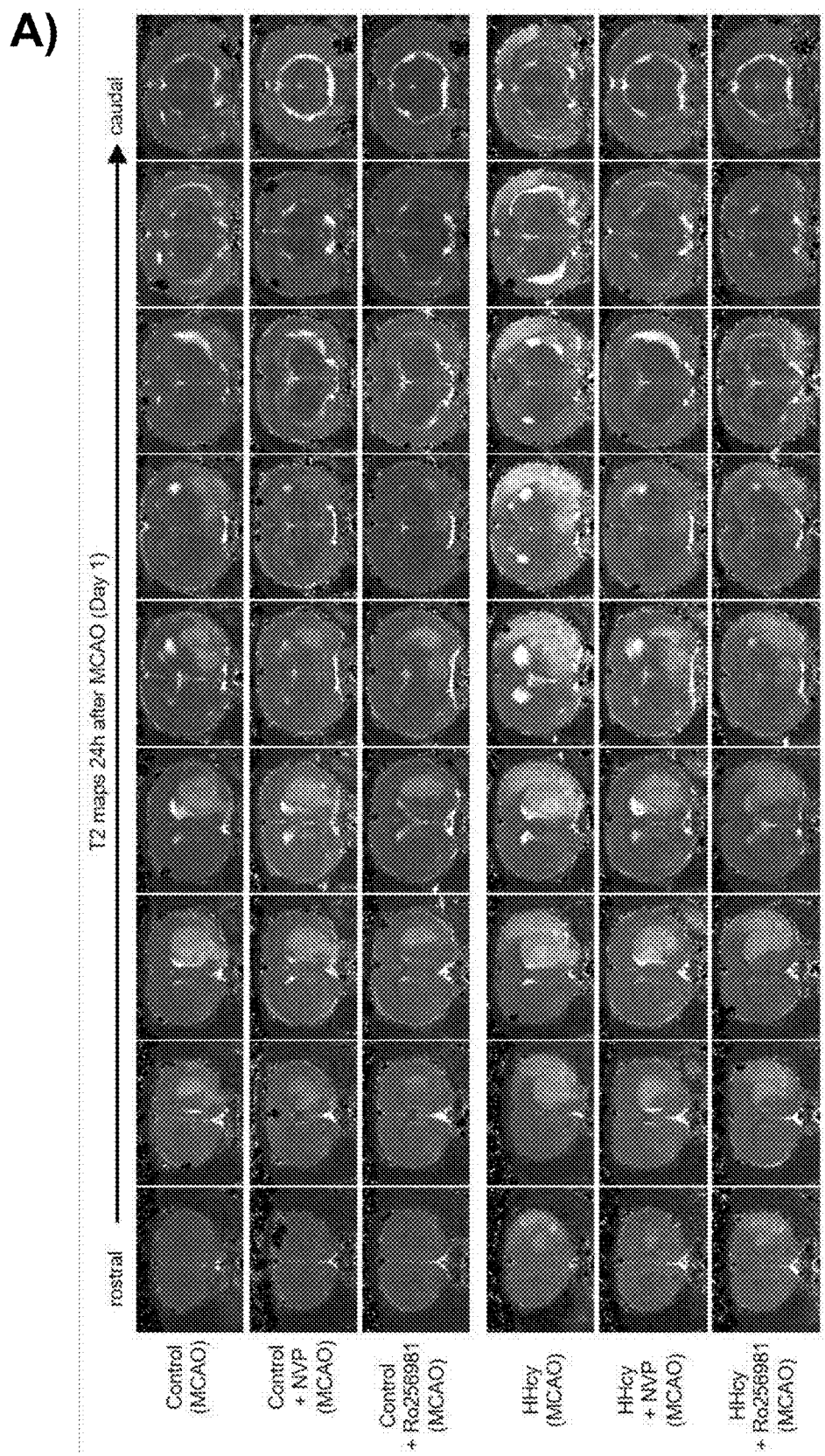
FIG. 4. Pharmacological inhibition of GluN2A-NMDAR with NVP-AAM077 attenuates hyperhomocysteinemia-induced exacerbation of ischemic brain damage. (A) Representative T2 maps at 24 hours post-MCAO acquired from control and hyperhomocysteinemic (HHcy) rats treated with vehicle, NVP-AAM077 (NVP) or Ro 256981 at the onset of the ischemic insult. (B) Quantitative analysis of total infarct volume in control rats treated with NVP. (C) Quantitative analysis of total infarct volume in HHcy rats treated with NVP. (D) Quantitative analysis of total infarct volume in control rats treated with Ro 256981. (E) Quantitative analysis of total infarct volume in HHcy rats treated with Ro 256981. Values are expressed as mean±SEM (control: n=11, control+NVP: n=12, vehicle+Ro 256981: n=10, HHcy: n=15, HHcy+NVP: n=11, HHcy+Ro 256981: n=7). *p<0.005 for control vs. control+Ro 256981 treated rats and **p<0.001 for HHcy vs. HHcy+NVP treated rats.
Figure 4:
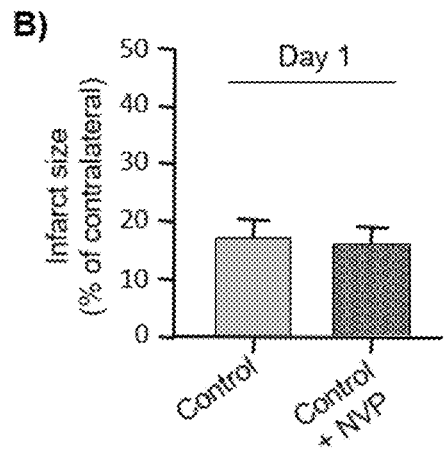
Figure 4:
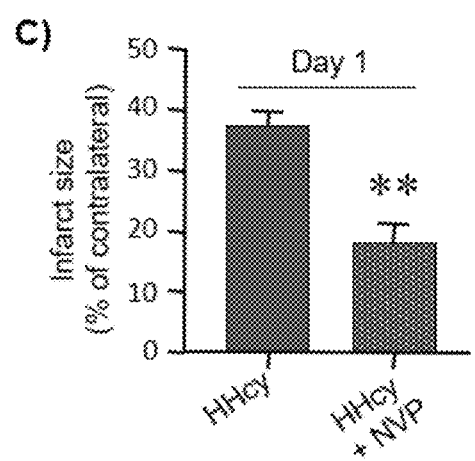
Figure 4:
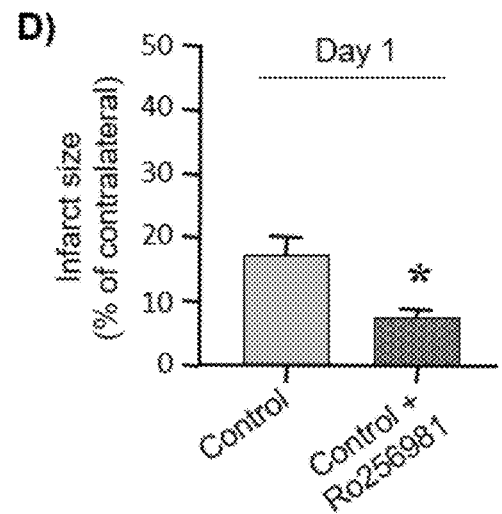
Figure 4:
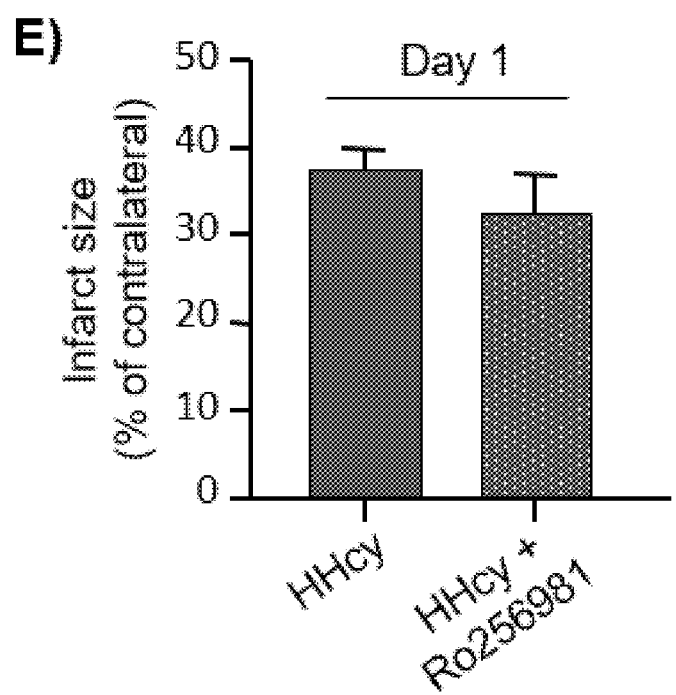

GluN2A-NMDAR Activity Exacerbates Ischemic Brain Damage in Hyperhomocysteinemic Rats Pharmacological inhibition of NMDAR subunits revealed mechanisms associated with the exacerbation of ischemic brain injury under hyperhomocysteinemic condition. Functional NMDARs typically include a GluN1 subunit with at least one GluN2 subunit. In the adult forebrain, where stroke most frequently occurs, GluN2A and GluN2B are the most predominant GluN2 subunits. Therefore, the effects of two subunit specific antagonists, NVP-AAM077, which preferentially inhibits GluN2A-NMDARs, and Ro 25-6981, which specifically blocks GluN2B-NMDARs, were evaluated. Both control and hyperhomocysteinemic rats were subjected to MCAO (60 min) and NVP-AAM077 (1.2 mg/kg body weight) or Ro 256981 (6 mg/kg body weight) was injected intravenously (through the femoral vein) at the onset of the ischemic insult, followed by reperfusion. The representative MRI T2 maps acquired 24 hours after MCAO (FIG. 4A), and quantitative analysis of the ischemic lesion volume from T2 maps show that inhibition of GluN2A-NMDARs with NVP-AAM077 fails to reduce the infarct size in the control rats (FIG. 4B; control: 18.65±2.89% vs. control+NVP: 16.07±2.8%; $p=0.530$; $r=0.137$), which has also been observed in an earlier study (Liu et al., 2007). In contrast, inhibition of GluN2A-NMDARs in hyperhomocysteinemic rats with NVP-AAM077 significantly reduces ischemic infarct size in hyperhomocysteinemic rats to a level that is comparable with the ischemic infarct size observed in the control rats (FIG. 4C; HHcy: 37.41±2.33% vs. HHcy+NVP: 17.98±3.24%; $p<0.0001$; $r=0.714$). On the other hand, treatment with GluN2B-NMDAR antagonist Ro 256981 significantly reduces infarct size in the control rats (FIG. 4D; control: 18.65±2.89% vs. control+Ro 256981: 7.46±1.24%; $p=0.002$; $r=0.618$). Treating hyperhomocysteinemic rats with Ro 256981 also results in a small but non-significant decrease in infarct size (FIG. 4E: HHcy: 37.41±2.33% vs. HHcy+Ro 256981: 32.48±4.32%; $p=0.286$; $r=0.237$). The inability of the GluN2A-NMDAR inhibitor to reduce ischemic lesion volume in the control rats suggests that in the absence of any underlying comorbidity, the progression of ischemic brain damage is primarily mediated through GluN2B-NMDAR signaling. However, in the presence of the comorbid condition of hyperhomocysteinemia GluN2A-NMDAR activation plays an additional role in the exacerbation of the ischemic brain damage.

Figure 5:
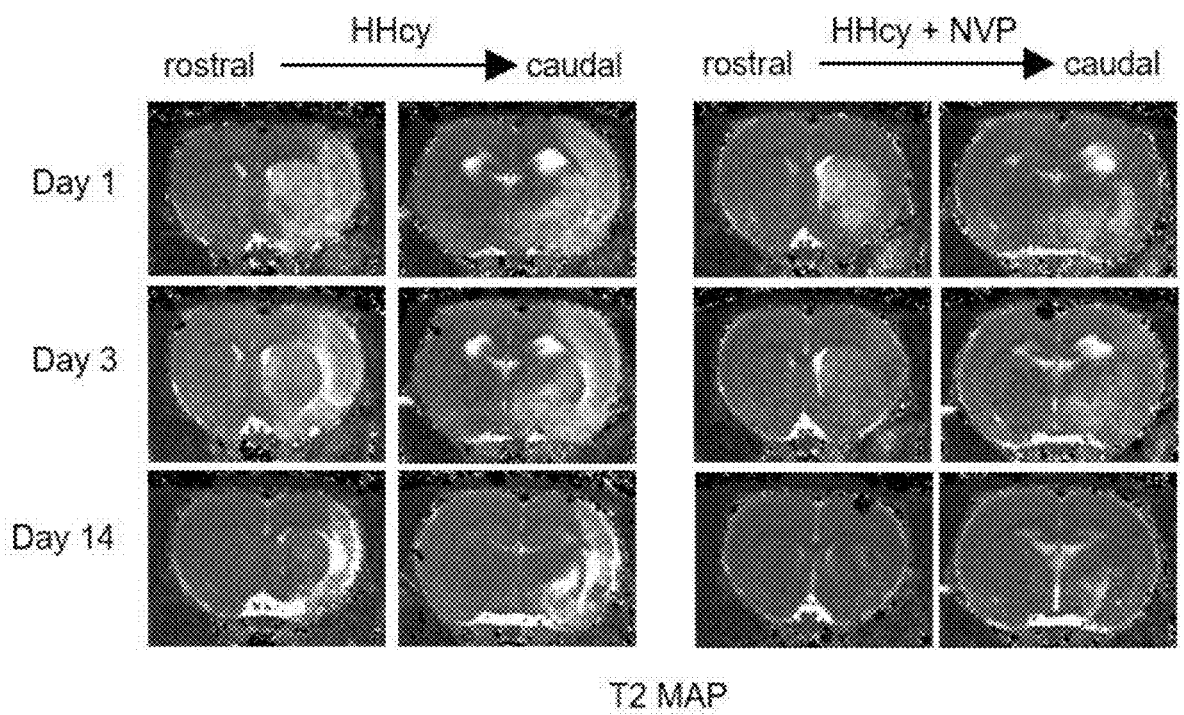
FIG. 5. Effect of GluN2A-NMDARs inhibition on the progression of ischemic brain damage in hyperhomocysteinemic rats. (A) Representative T2 maps from day 1, day 3, and day 14 after MCAO, acquired from hyperhomocysteinemic rats treated with vehicle (HHcy) or NVP-AAM077 (HHcy+NVP), showing changes in ischemic lesion size from rostral to caudal regions of the brain. Corresponding bar diagram provide quantitative analysis of total infarct volume, expressed as mean±SEM (on days 1 and 3—HHcy: n=15; on day 14—HHcy: n=14; on days 1, 3 and 14—HHcy+NVP: n=11). (B) Representative ADC maps acquired from HHcy and HHcy+NVP treated rats at day 14 post-MCAO, featuring hyperintense areas that co-loacalize with the lesion area in the T2 maps at day 14 post-MCAO. Quantitative analysis of ADC values in the lesion area, expressed as mean±SEM (HHcy: n=14, HHcy+NVP: n=10). (C) Representative FA maps acquired from the same slices as ADC and T2 maps at 14 days post-MCAO as well as quantitative analysis of FA values expressed as mean±SEM (HHcy: n=14, HHcy+NVP: n=10). *p<0.01, p<0.005 and *p<0.001 for HHCy vs. HHcy+NVP treated rats.
Figure 5:
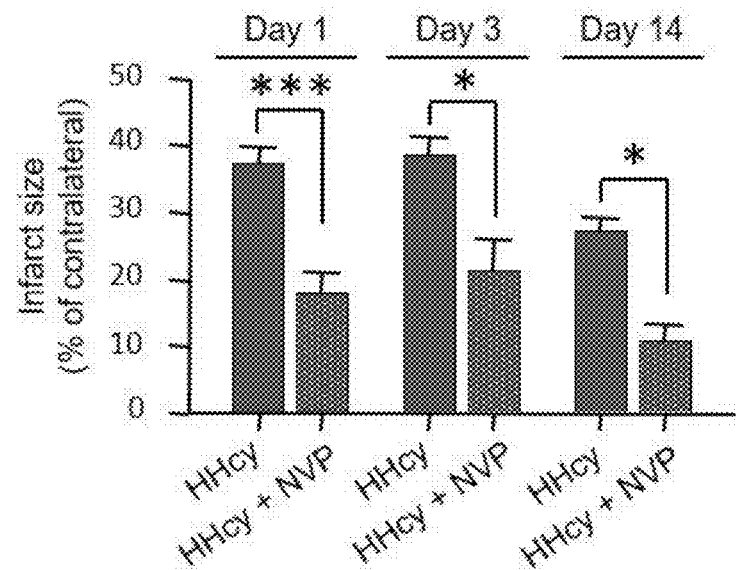
Figure 5:
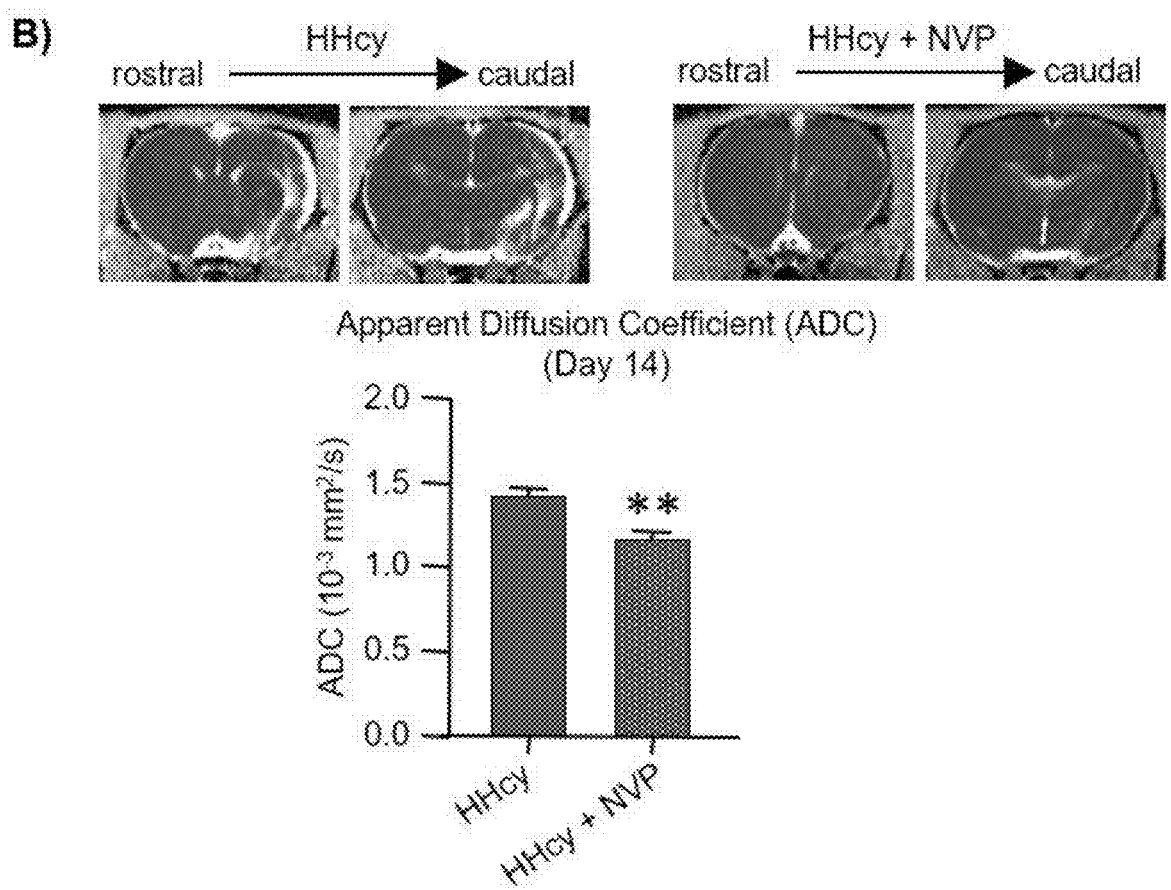
Figure 5:
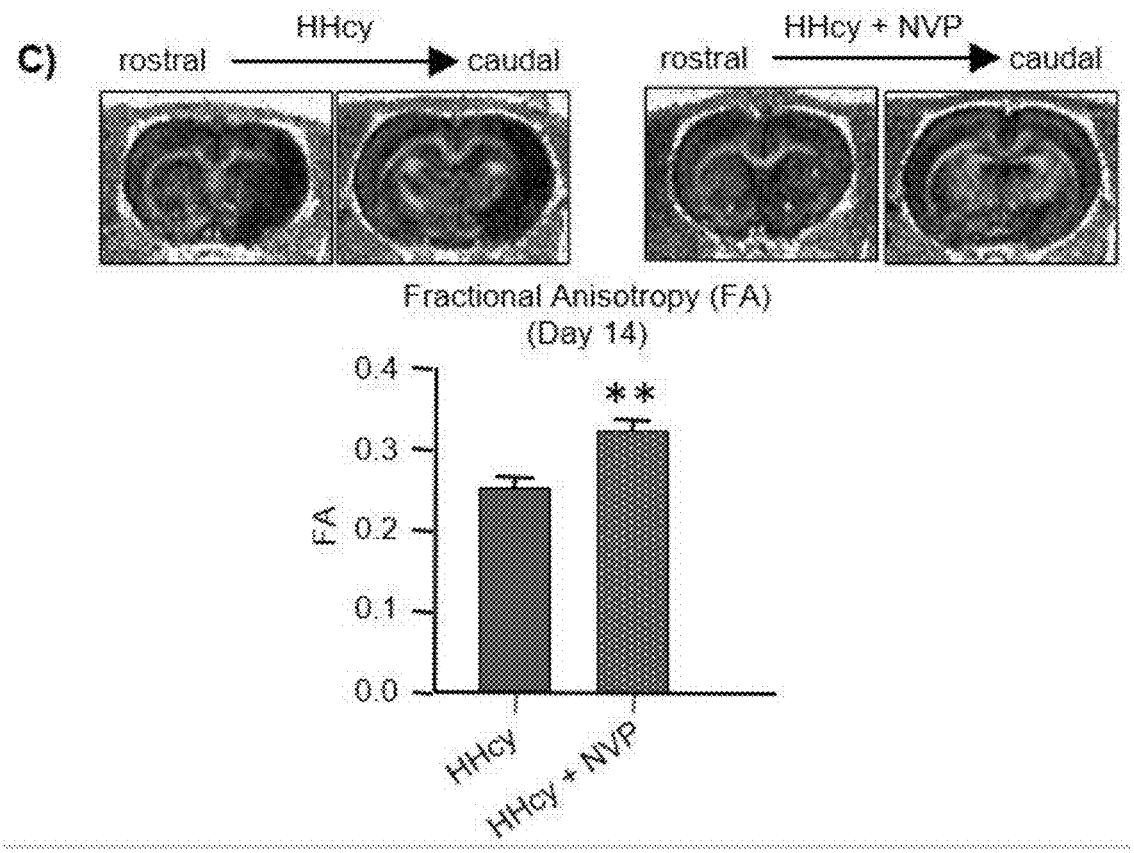

In subsequent studies, ischemic lesion volume in hyperhomocysteinemic rats treated with or without NVP-AAM077 (1.2 mg/kg body weight) was evaluated up to 14 days post-MCAO to assess the late manifestation of brain injury following treatment. Longitudinal evaluation of the infarct size shows significant group difference [$F_{(1, 23)}=26.891$, $p<0.0001$] and day effect [$F_{(2, 46)}=14.891$, $p<0.0001$] between NVP-AAM077 treated and untreated hyperhomocysteinemic rats. However, treatment by day interaction is not significant. The representative T2 maps and post hoc analysis of the lesion volume from the T2 maps (FIG. 5A) show that NVP-AAM077 treated group has significantly smaller lesion size at both day 3 (HHcy: 38.63±2.75% vs. HHcy+NVP-AAM077: 19.61±4.48%) and day 14 (HHcy: 27.16±2.18% vs. HHcy+NVP-AAM077: 10.76±2.40%) after MCAO. Evaluation of the structural integrity of the brain tissue in the infarcted area at day 14 show a significant decrease in ADC value (HHcy: $1.41\times10^3\pm0.06\times10^3$ mm²/sec vs. HHcy+NVP-AAM077: $1.16\times10^3\pm0.05\times10^3$ mm²/sec; $p=0.003$; $r=0.574$) and a concomitant increase in FA value (HHcy: 0.25±0.01 vs. HHcy+NVP-AAM077: 0.32±0.01; $p=0.002$; $r=0.599$) following treatment with NVP-AAM077, reflecting reduced tissue breakdown and less accumulation of extracellular water in the residual stroke cavity (FIG. 5B, C). These findings indicate that the effect of early treatment with NVP-AAM077 is not transient.

Figure 6:
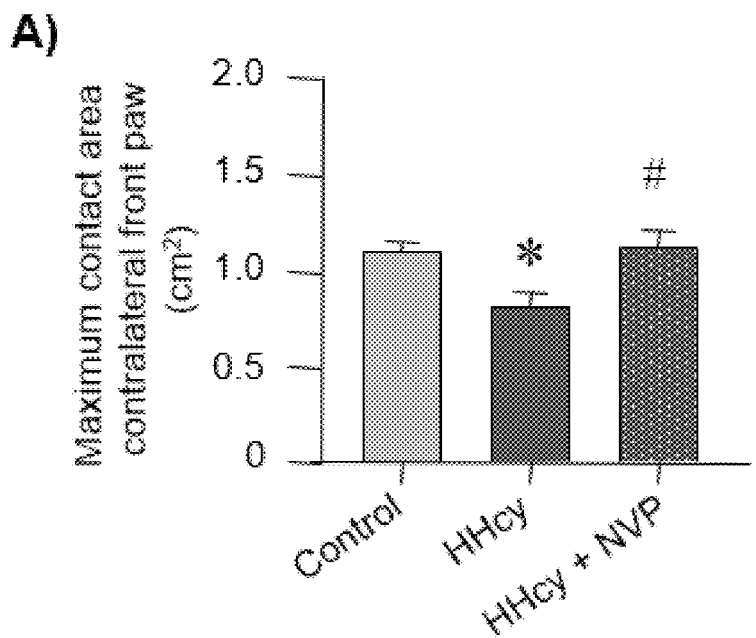
FIG. 6. Effect of GluN2A-NMDAR inhibition on ischemia-induced normal gait impairment in hyperhomocysteinemic rats. Quantitative analysis of (A) Maximum contact area (mm2); (B) Print area (cm$^2$) in the affected forepaw (contralateral) 7 days after MCAO in control, hyperhomocysteinemic (HHcy) and hyperhomocysteinemic rats treated with GluN2A-NMDAR inhibitor NVP-AAM077 (HHcy+NVP-AAM077). (C) Print position (cm) in the affected forepaw (contralateral) 7 days after MCAO in control, hyperhomocysteinemic (HHcy) and hyperhomocysteinemic rats treated with GluN2A-NMDAR inhibitor NVP-AAM077 (HHcy + NVP-AAM077). Values in (B) and (C) are represented as mean±SEM (control: n=11, HHcy: n=14, HHcy+NVP: n=11). *p<0.05 for control vs. HHcy rats and #p<0.05 for HHcy vs. HHcy+NVP treated rats.
Figure 6:
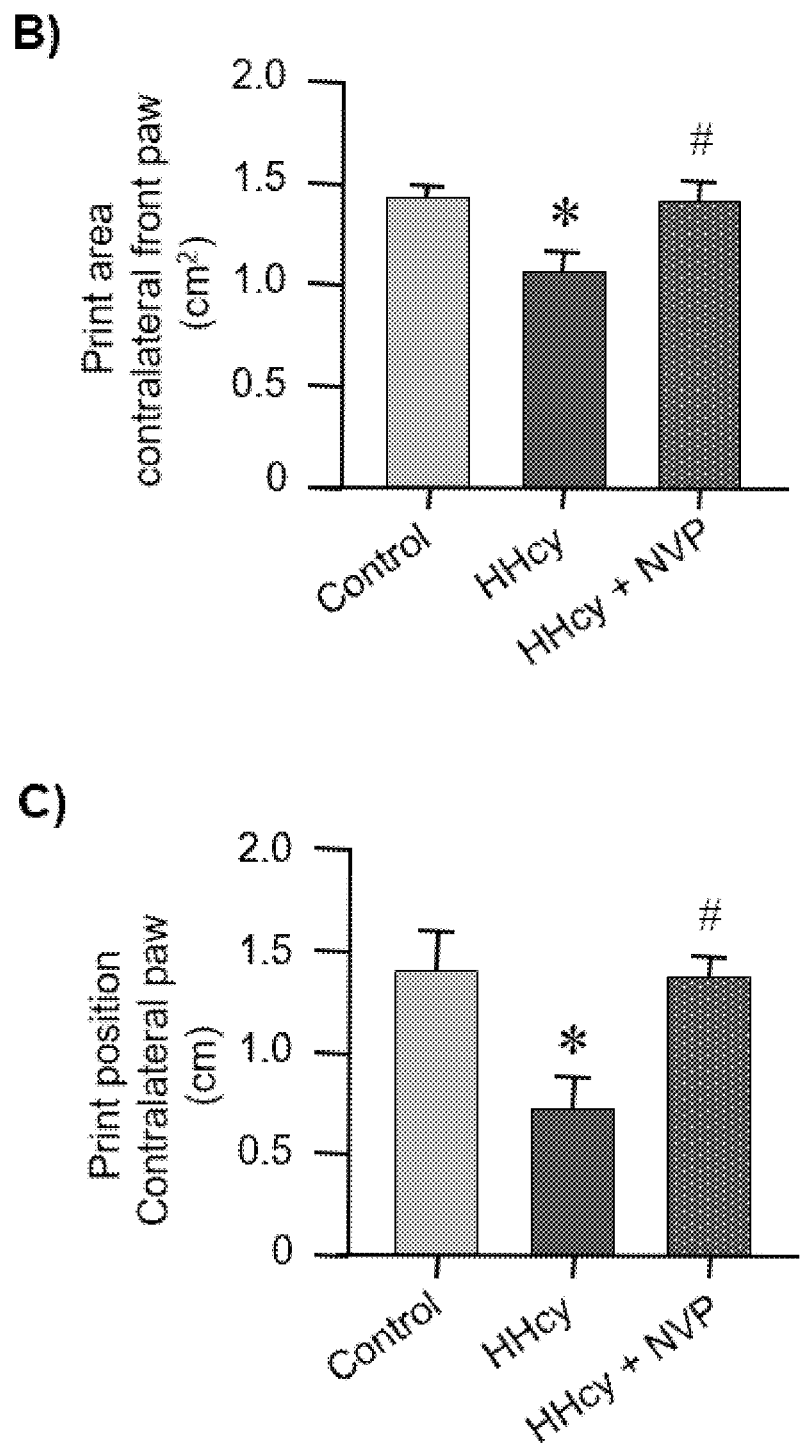
Figure 7:
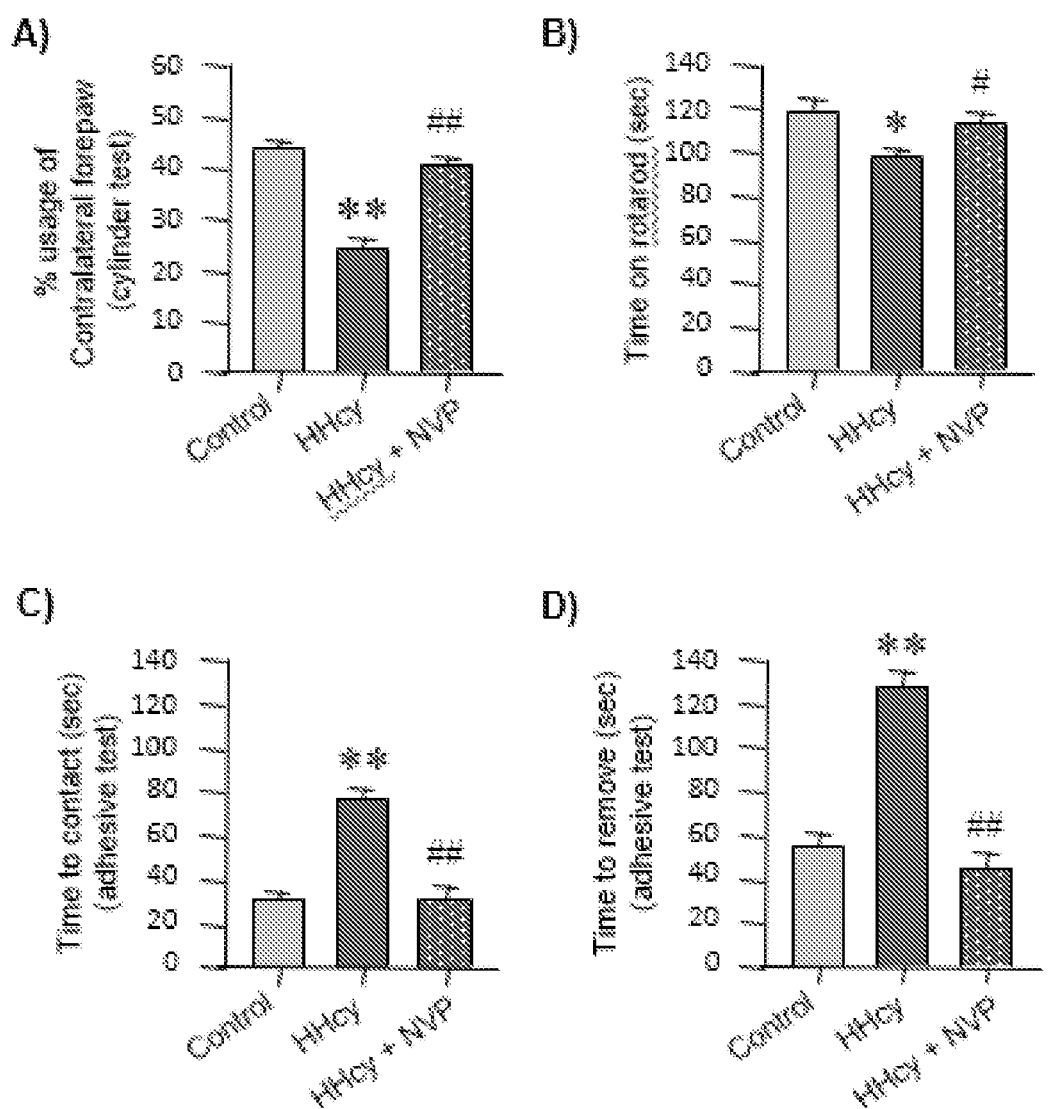
FIG. 7. Effect of GluN2A-NMDAR inhibition on ischemia-induced motor coordination and sensorimotor deficit in hyperhomocysteinemic rats. Control, hyperhomocysteinemic (HHcy) and hyperhomocysteinemic rats treated with GluN2A-NMDAR inhibitor NVP-AAM077 (HHcy+NVP) were subjected to MCAO followed by reperfusion. (A) Quantitative analysis of spontaneous contralateral forelimb use assessed using cylinder test (day 8 post MCAO; control: n=7, HHcy: n=14, HHcy+NVP: n=11). (B) Quantitative analysis of motor impairment and balance assessed using the rotarod test (day 8 post MCAO; control: n=12, HHcy: n=14, HHcy+NVP: n=11). (C) Quantitative analysis of mean latency to detect adhesive label from the contralateral forepaw (time in seconds) assessed as a measure of sensorimotor function (day 9 post MCAO; control: n=12, HHcy: n=15, HHcy+NVP: n=11). (D) Quantitative analysis of mean latency to remove an adhesive label from the contralateral forepaw (time in seconds) assessed as a measure of sensorimotor function (day 9 post MCAO; control: n=12, HHcy: n=15, HHcy+NVP: n=11). All data are expressed as mean±SEM; *p<0.01 and **p<0.001 for control vs. HHcy rats; #p<0.01 and ##p<0.001 for HHcy vs. HHcy+NVP treated rats.

Inhibiting GluN2A-NMDARs Reduces Behavioral Deficits Following Ischemia in Hyperhomocysteinemic Rats The effect of ischemic brain injury on post-stroke behavioral impairment was evaluated in both the control and hyperhomocysteinemic rats. In addition, the treatment effect of hyperhomocysteinemic rats with NVP-AAM077 (1.2 mg/kg body weight) was also evaluated. A computer-assisted gait imaging and analysis system for rodents (CatWalk) was used to assess the changes in normal gait. Changes in gait parameters (maximum contact area, print area and print position) of the contralateral forepaw were assessed one week after stroke in control, hyperhomocysteinemic, and NVP-AAM077-treated hyperhomocysteinemic rats. Data analysis by one-way ANOVA reveals significant differences between the treatment groups for maximum contact area [$F_{(2, 33)}=4.956$, $p=0.0131$], print area [$F_{(2, 33)}=5.776$, $p=0.007$] and print position [$F_{(2, 33)}=6.129$, $p=0.005$], Post hoc analyses further show that the maximum area of the affected forepaw that comes in contact with the floor during the stance phase of gait (contact area) in hyperhomocysteinemic rats is significantly reduced when compared to control rats (FIG. 6A; control: 1.09±0.056 vs. HHcy: 0.8±0.082; $p<0.05$). In contrast, treatment with NVP-AAM077 significantly increases the maximum contact area of the affected paw when compared to the untreated hyperhomocysteinemic group (FIG. 6A; HHcy: 0.8±0.082 vs. HHcy+NVP-AAM077: 1.11±0.092; $p<0.05$). Similarly, the maximum floor area that comes in contact with the affected forepaw during the stance phase (print area) is significantly lesser for hyperhomocysteinemic rats when compared with the control rats (FIG. 6B; control: 1.42±0.063 vs. HHcy: 1.06±0.097; $p<0.05$). However, a significant improvement in print area is observed following treatment with NVP-AAM077 (FIG. 6B; HHcy: 1.06±0.097 vs. HHcy+NVP-AAM077: 1.41±0.092; $p<0.05$). In addition, the distance between the fore paw and hind paw of the affected side during movement (print position) is significantly less in the hyperhomocysteinemic rats when compared to the control rats (FIG. 6C; control: 1.4±0.19 vs. HHcy: 0.72±0.15; $p<0.05$), which increases to control levels following treatment with NVP-AAM077 (FIG. 6C; HHcy: 0.72±0.15 vs. HHcy+NVP-AAM077: 1.37±0.097; $p<0.05$). Next, the deficit in spontaneous usage of the affected forelimb was evaluated using the cylinder test on day 8 after MCAO. Significant difference was observed between the treatment groups [$F_{(2, 29)}=22.98$, $p<0.0001$], FIG. 7A shows that the usage of the affected forepaw in hyperhomocysteinemic rats is significantly less as compared to control rats (control: 43.73±1.61% vs. HHcy: 24.24±2.37%; $p<0.0001$), and treatment with NVP-AAM077 results in significant improvement in spontaneous usage of the affected forepaw in hyperhomocysteinemic rats (HHcy: 24.24±2.37% vs. HHcy+NVP-AAM077: 40.51±1.86; $p<0.0001$).

The latency to fall from an accelerated rotarod was measured to evaluate balance and motor coordination. Data analyses show significant difference between the treatment groups [$F_{(2, 34)}$=5.813, p=0.006], Evaluation of rotarod performance of each group show that hyperhomocysteinemic rats are significantly less efficient in maintaining balance on the rotarod as compared to the control rats (FIG. 7B; control: 118.5±5.31 sec vs. HHcy: 96.99±4.11 sec; p<0.01), while treatment with NVP-AAM077 significantly enhances the performance of hyperhomocysteinemic rats (FIG. 7B; HHcy: 96.99±4.11 sec vs. HHcy+NVP-AAM077: 112.51±4.9 sec; p<0.05).

Sensory motor deficit in the contralateral forelimb of control, hyperhomocysteinemic, and NVP-AAM077-treated hyperhomocysteinemic rats was evaluated 9 days after MCAO by measuring the latency to contact and remove a stimulus (adhesive tape) from the paw. Data analyses show significant group differences for both the time to make contact [$F_{(2, 35)}$=26.42, p<0.0001] and the time to remove [$F_{(2, 35)}$=42.57, p<0.0001] the adhesive tape from the contralateral forepaw. FIGS. 7C and D shows that hyperhomocysteinemic rats take significantly longer time to contact (control: 30.61±4.69 s vs. HHcy: 76.82±5.45 s; p<0.0001) and remove (control: 54.53±6.51 s vs. HHcy: 127.86±7.29 s; p<0.0001) the tape when compared to the control rats. On the other hand, treatment of hyperhomocysteinemic rats with NVP-AAM077 significantly reduces both the time to contact (HHcy: 76.82±5.45 s vs. HHcy+NVP-AAM077: 31.18±5.68 s; p<0.0001) and remove (HHcy: 127.86±7.29 s vs. HHcy+NVP-AAM077: 44.24±7.59 s; p<0.0001) the tape, indicating an improvement in both sensory and motor skill. Taken together these findings demonstrate that GluN2A-NMDAR plays a role in the worsening of behavioral deficits in hyperhomocysteinemic rats following an ischemic insult.

Figure 8:
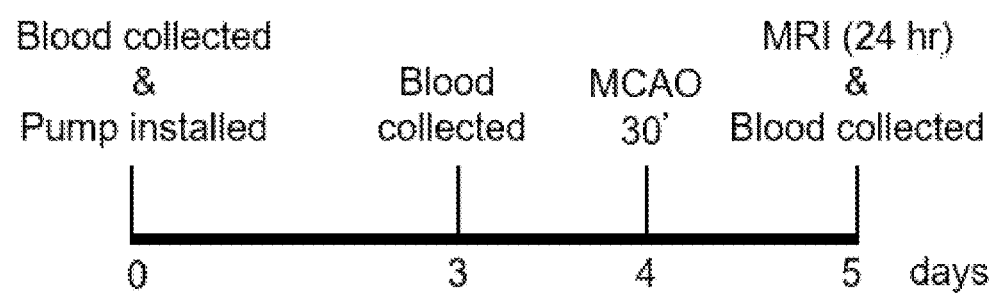
FIG. 8. Effect of GluN2A-NMDAR gene deletion on the exacerbation of ischemic brain damage in hyperhomocysteinemic mice. (A) Schematic representation of the timeline of blood collection following implantation of osmotic pump, MCA, reperfusion and MRI scan in wildtype (WT) and GluN2A-KO mice. (B) Quantitative analysis of total plasma homocysteine level in WT and hyperhomocysteinemic (HHcy) mice before (0 day) and after (3 days and 5 days) implantation of pump. Values are expressed as mean±SEM (n=3-5/group). (C) Representative photomicrographs of T2 maps acquired from control-WT, HHcy-WT, control-GluN2A-KO and HHcy-GluN2A-KO mice following MCAO (30 minutes) and reperfusion (24 hours). (D) Quantitative analysis of total infarct volume in WT (control and HHcy) and GluN2A-KO (control or HHcy) mice. Values are expressed as mean±SEM (control-WT: n=8, HHcy-WT: n=5, control-GluN2A: n=3, HHcy-GluN2A-KO: n=3). *p<0.01 for WT mice day 0 vs. WT mice day 3 or 5; #p<0.01 for GluN2A-NMDAR-KO mice day 0 vs. GluN2A-NMDAR-KO mice day 3 or 5. **p<0.001 for control-WT vs. HHcy-WT mice.
Figure 8:
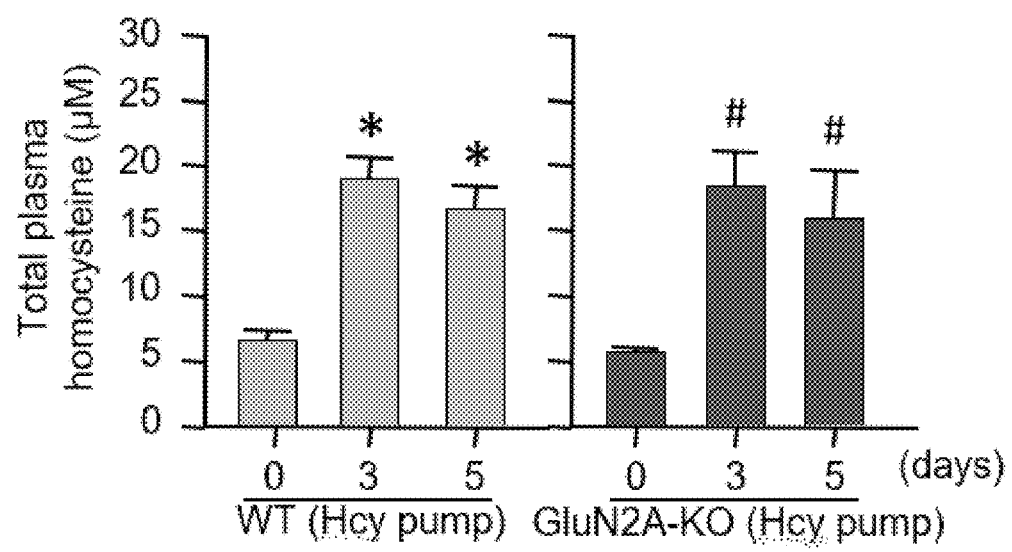
Figure 8:
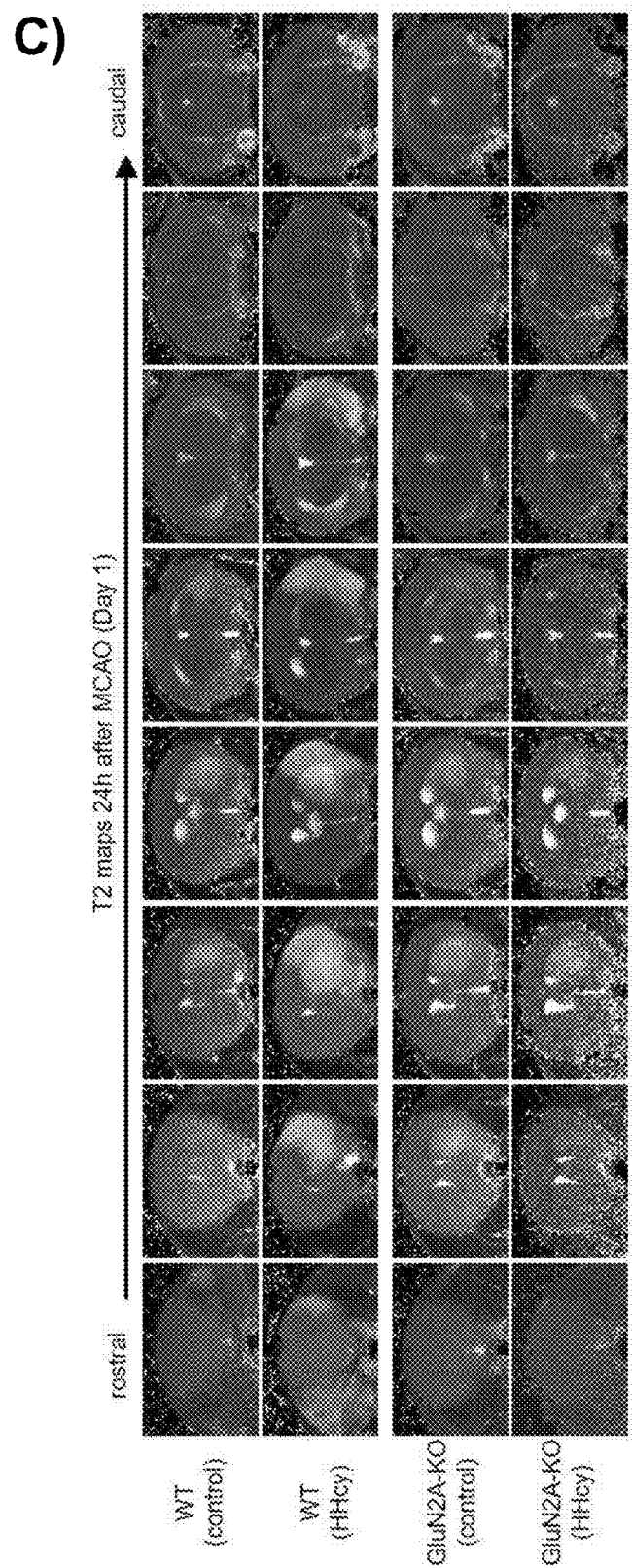
Figure 8:
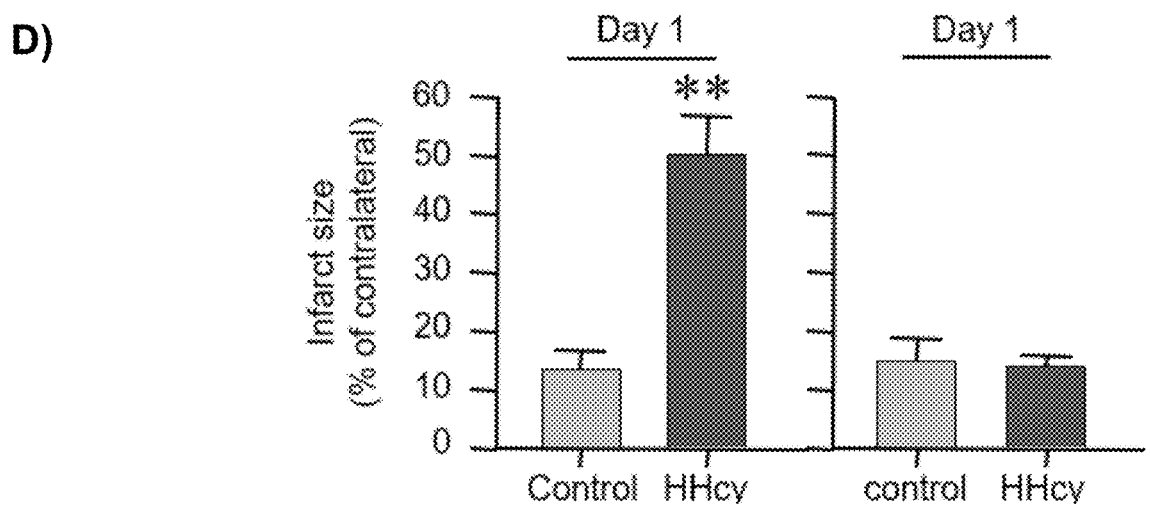

Genetic Deletion of GluN2A-NMDARs Mitigates Ischemic Brain Injury in Hyperhomocysteinemic Mice Deletion of endogenous GluN2A-NMDARs attenuates the exacerbation of ischemic brain damage observed under hyperhomocysteinemic conditions. For these studies, osmotic pumps containing 200 mM L-homocysteine were installed in WT and GluN2A-KO mice to render them hyperhomocysteinemic. As outlined in FIG. 8A, blood samples were collected from the different groups of mice on day 0 (before pump installation) and days 3 and 5 after pump implantation for analysis of plasma homocysteine level. In WT mice, the total plasma homocysteine increased from 6.6±0.73 µM (day 0) to 18.97±1.68 µM on day 3 (p<0.01) and remained elevated at 16.68±1.73 µM on day 5 (p<0.01). In GluN2A-KO mice, the total plasma homocysteine level also increased from 5.72±0.33 µM (day 0) to 18.46±2.55 µM on day 3 (p<0.01) and remained elevated at 15.92±2.09 µM on day 5 (p<0.01). Both WT and GluN2A-KO mice implanted with saline pump (control) or homocysteine pump (hyperhomocysteinemic) were subjected to MCAO (30 min) 4 days after pump implantation. This was followed by reperfusion and assessment of infarct size by MRI 24 hours after MCAO as outlined in FIG. 8A. The representative T2 maps (FIG. 8C) and quantitative analysis of infarct volume (FIG. 8D) show that ischemic insult in both the WT control mice and GluN2A-KO control mice resulted in a small infarct size that is limited to the striatum (WT control: 13.52±3.13% vs. GluN2A-KO control: 14.85±3.8%, p=0.82; r=0.077). However, ischemic insult in the hyperhomocysteinemic WT mice resulted in significant exacerbation of the ischemic brain damage that encompassed the striatum and the cortex (WT control: 13.52±3.12% vs. WT HHcy: 50.28±6.54%; p=0.0001; r=0.864). These findings are consistent with data shown in rats (FIGS. 2C and D), suggesting that regardless of species, hyperhomocysteinemic condition exacerbates ischemic brain injury. However, such exacerbation of ischemic brain injury was not observed in the hyperhomocysteinemic GluN2A-KO mice (GluN2A-KO control: 14.85±3.8% vs. GluN2A-KO HHcy: 14.1±1.77; p=0.867; r=0.088), confirming a role of GluN2A-NMDARs in hyperhomocysteinemia-induced exacerbation of ischemic brain injury.

Thus, mild hyperhomocysteinemia leads to exacerbation of brain damage and deficits in sensory motor function following a transient cerebral ischemia. Importantly, the studies also show that pharmacological inhibition of GluN2A-NMDARs reduces ischemic brain damage in hyperhomocysteinemic rats but does not alter ischemic lesion size in rats with normal homocysteine level, indicating that exacerbation of brain injury under hyperhomocysteinemic condition involves GluN2A-NMDAR activation. Consistent with this interpretation, studies in GluN2A-KO mice further show that in the absence of GluN2A-NMDARs, hyperhomocysteinemia fails to exacerbate ischemic brain damage, validating the role of GluN2A-NMDARs in hyperhomocysteinemia-induced brain injury during an ischemic insult.

This disclosure provides strong evidence for GluN2A-NMDAR signaling being involved in ischemic brain injury under hyperhomocysteinemic condition. A comparison of the anatomical T2 maps, ADC, and FA values acquired from hyperhomocysteinemic animals subjected to a mild ischemic insult and treated with or without NVP-AAM077, a model inhibitor of GluN2A-NMDAR activation, show a significant reduction in ischemic lesion size and improved structural integrity within the lesion area following treatment. Behavioral studies also show a significant improvement in normal gait and sensory motor function following treatment. To further assess any potentially nonselective effect of NVP-AAM077 on GluN2B-NMDARs, the effect of blocking GluN2A-NMDAR or GluN2B-NMDAR on ischemic brain damage was studied in the control rats. Administering GluN2B-NMDAR antagonist Ro 25-6981, but not GluN2A-NMDAR inhibitor NVP-AAM077, reduces ischemic brain damage in the control rats, indicating the role of GluN2B-NMDARs in mediating ischemic brain damage in the control rats. The findings confirm the role of NVP-AAM07 in selectively blocking GluN2A-NMDARs in attenuating ischemic brain damage under hyperhomocysteinemic conditions. Further validation for a role of GluN2A-NMDAR in the exacerbation of ischemic brain injury under hyperhomocysteinemic condition comes from additional studies in GluN2A-KO mice. The findings show that in the absence of GluN2A-NMDARs, ischemic lesion volume does not increase with elevated levels of total plasma homocysteine and is in agreement with the results obtained with the pharmacological blockade of GluN2A-NMDARs in rats.

Taken together, the above findings demonstrate that transient focal ischemia under hyperhomocysteinemic conditions triggers two divergent pathogenic pathways resulting in exacerbation of brain injury. While activation of GluN2B-NMDARs contributes to glutamate-mediated ischemic brain injury, GluN2A-NMDAR stimulation is involved in homocysteine-dependent brain damage. These unique findings not only establish that homocysteine-dependent neuronal injury and subsequent brain damage is distinctly different from the mechanisms generally implicated in ischemic brain injury but also highlights the differential response of NMDAR subtypes to homocysteine and glutamate in facilitating neurotoxicity. Thus, it appears that the view that GluN2B-

NMDARs promotes apoptosis whereas GluN2A-NMDARs opposes apoptosis in neurons is overly simplistic, and detailed analysis of these pathways is warranted in any model of neurotoxicity.

Figure 9:
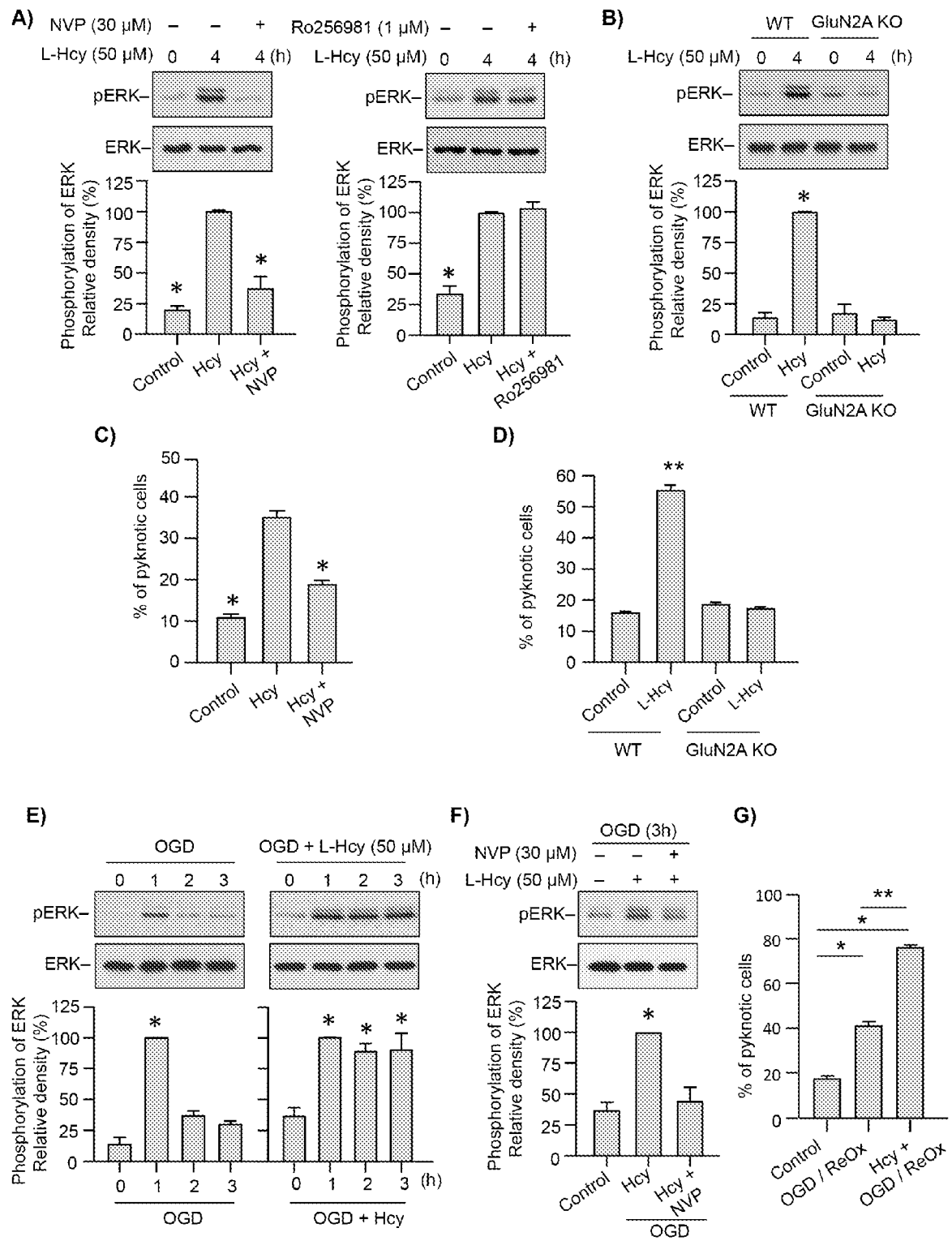
FIG. 9. Cortical neuron cultures from embryonic rat brain were treated with 50 µM L-homocysteine (L-Hcy) for four hours in the absence or presence of NVP-AAM077 (30 nM, left panel) or Ro 2506981 (1 µM, right panel). (B) Cortical neuron cultures from WT and GluN2A KO mice embryonic brain were treated with 50 µM L-Hcy for four hours. (A, B) Cell lysates from both rat and mice neuron cultures were analyzed by immunoblotting using anti-phospho ERK MAPK (pERK) and anti-ERK MAPK (ERK) antibodies. Values are mean±SEM (n=5). (A) *p<0.001 from 4 hr homocysteine treatment; (B) *p<0.001 from control of corresponding wild type or GluN2A-NMDAR KO cultures. (C) Neurons cultures obtained from rat embryos were treated with L-homocysteine (50 µM, 18 h) in the absence or presence of NVP-AAM077 (30 nM). (D) Neuron cultures obtained from wild type and GluN2A-NMDAR KO mice embryonic brain were treated with L-homocysteine (50 µM) for 18 h. (C, D) Cells were subjected to Hoechst DNA staining followed by quantitative analysis of percentage of neurons with pyknotic nuclei. Values are mean±SEM (n=1500 cells/condition from 4 experiments). (C) *p<0.001 from 18 h homocysteine treatment. (D) **p<0.001 from control of corresponding wild type or GluN2A-NMDAR KO cultures. (E) Rat cortical neuron cultures were exposed to oxygen-glucose deprivation (OGD) for specified time periods in the absence (left panel) or presence of L-Hcy (50 µM, right panel). (F) Rat cortical neuron cultures were exposed to only OGD, or OGD in the presence of either L-Hcy (50 µM) or L-Hcy and NVP-AAM077 (30 nM) for 3 h. (E, F) Cell lysates were analyzed by immunoblotting using anti-phospho ERK MAPK (pERK) and anti-ERK MAPK (ERK) antibodies. Values are mean±SEM (n=5).

Mechanistic Basis of GluN2A-NMDAR-Dependent Exacerbation of Ischemic Brain Injury Under Hyperhomocysteinemic Condition Homocysteine-NMDAR-mediated sustained ERK MAPK phosphorylation in neurons follows a two-tier pattern, where the delayed larger increase in ERK MAPK phosphorylation is predominantly responsible for homocysteine-dependent neuronal cell death. To examine the role of GluN2A-NMDARs in homocysteine induced delayed ERK MAPK phosphorylation, cortical neuronal cultures from rat brain were treated with L-homocysteine (50 µM, four hours) in the presence or absence of GluN2A-NMDAR inhibitor, NVP-AAM077, or GluN2B-NMDAR-selective inhibitor Ro 256981. FIG. 9A shows significant increase in ERK MAPK phosphorylation with homocysteine treatment. Incubating neurons with NVP-AAM077 blocks homocysteine-induced ERK MAPK phosphorylation. In contrast, Ro 256981 has no effect on the homocysteine-mediated ERK MAPK phosphorylation. The findings indicate that the inhibitory effect of NVP-AAM077 most likely resulted from GluN2A-NMDAR blockade. To confirm this interpretation, neuron cultures obtained from WT and GluN2A-KO mice were exposed to L-homocysteine treatment (50 µM, four hours). FIG. 9B shows that homocysteine treatment leads to significant increase in ERK MAPK phosphorylation in the neuronal cultures obtained from WT mice, while it remains unchanged in the neurons obtained from GluN2A-KO mice, when compared to the respective untreated controls. The findings confirm the role of GluN2A-NMDAR in homocysteine-induced delayed ERK MAPK phosphorylation responsible for neuronal cell death. Additional studies evaluated the role of GluN2A-NMDARs in homocysteine-mediated neuronal injury. For these experiments rat cortical neuronal cultures were treated with L-homocysteine (50 µM, 24 hours) in the presence or absence of NVP-AAM077 (30 nM). Twenty-four hours later cells were precessed for Hoechst DNA staining to test for cell viability. Quantitative analysis of the extent of cell death (FIG. 9C) shows a significant increase in the number of apoptotic cells following L-homocysteine treatment as compared to untreated controls. Application of NVP-AAM077 during L-homocysteine treatment significantly reduced the number of apoptotic cells compared to L-homocysteine treatment alone.

To confirm the role of GluN2A-NMDAR in homocysteine-mediated neuronal cell death in subsequent studies mouse neuronal cultures obtained from WT and GluN2A-KO mice were exposed to L-homocysteine (50 µM) for 24 hours, followed by Hoechst staining and quantitative analysis of the extent of cell death. FIG. 9D shows a significant increase in cell death in the homocysteine treated neuronal cultures obtained from WT mice. In contrast, treatment of neuronal cultures obtained from GluN2A-NMDAR knock-out mice with homocysteine fails to alter cell death, when compared to untreated control (FIG. 9D).

Next, neuronal cultures were exposed to oxygen-glucose deprivation (OGD) to mimic ischemic injury, then the ERK MAPK phosphorylation profile in the absence or presence of homocysteine was assessed. Immunoblot analysis shows that OGD insult alone leads to a transient increase in ERK MAPK phosphorylation within 1 h (FIG. 9E). In contrast, OGD in the presence of homocysteine causes sustained ERK MAPK phosphorylation throughout the time course examined (FIG. 9E). To evaluate the role of GluN2A-NMDAR in the sustained ERK MAPK phosphorylation, neurons were exposed to OGD and L-homocysteine in the presence or absence of NVPAAM077 for three hours. FIG. 9F shows that treatment with NVP-AAM077 inhibits the activation of ERK MAPK in neurons. To further determine whether the sustained ERK MAPK phosphorylation observed following OGD in the presence of L-homocysteine is also associated with enhanced neuronal injury, neuronal cultures were subjected to OGD for two hours in the presence of homocysteine (50 µM) and then maintained in re-oxygenated conditions for 22 hours. Quantitative analysis of the extent of cell death shows that OGD-induced cell death increases by two-fold in the presence of homocysteine (FIG. 9G). Together, these findings provide a basis for further evaluation of the role of GluN2A-NMDAR in exacerbation of hypoxic-ischemia induced neuronal injury in the presence of homocysteine.

Next, whether a mild ischemic insult under hyperhomocysteinemic condition could lead to prolonged increase in ERK MAPK phosphorylation was evaluated using a middle cerebral artery occlusion (MCAO) model. Normal and hyperhomocysteinemic Wistar rats were subjected to MCAO for 60 minutes followed by reperfusion for specified time periods (0, 3, 6, 12 h). Immunoblot analysis of tissue punches from the ipsilateral cortex show that, during the insult, (I60/0 h RPF) ERK MAPK phosphorylation increases significantly in the hyperhomocysteinemic rats and it remains sustained during reperfusion (FIG. 10A). NVP-AM077, however, blocks the prolonged phosphrylation of ERK MAPK in hyperhomocysteinemic rats at three hours of reperfusion. FIG. 10B shows that a significant reduction ERK MAPK phosphorylation in NVP-AAM077-treated rats when compared with the vehicle treated rats. These findings are consistent with GluN2A-NMDAR signaling and sustained ERK MAPK phosphorylation exacerbating brain injury following a mild ischemic insult under hyperhomocysteinemic condition.

In conclusion, the present study provides the first direct evidence that mild hyperhomocysteinemia accelerates the progression of ischemic brain injury. The study also identifies that hyperhomocysteinemia-induced neuronal damage involves signaling mediated through GluN2A-NMDARs that, together with ischemia-induced intracellular pathways, exacerbate brain injury. The findings provide a mechanistic basis for mitigating the adverse effects of hyperhomocysteinemia on ischemic stroke injury that may be extrapolated for mitigating adverse effects of hyperhomocysteinemia in individuals having other neurodegenerative disorders.

Inflammation:

Homocysteine Induces Increase in Neuronal COX2 Protein Level and PGE2 Release

Both cPLA2 and COX2 play important roles in PGE2 biosynthesis. To evaluate whether cPLA2 activation is regulated by homocysteine, primary cortical neuron cultures (12-14 days in vitro) were treated with L-homocysteine (50 µM) for varying time periods (0, 1 hour, 2 hours, 4 hours, or 6 hours) and cPLA2 activity was assessed in the cell lysates. Quantitative analysis in FIG. 11A shows that treatment of neurons with homocysteine significantly increases cPLA2 activity with time. To evaluate the effect of homocysteine on COX2 protein expression, cortical neuron cultures treated with L-homocysteine (50 µM) for the specified time periods were subjected to immunoblot analysis with COX2 antibody. The representative immunoblot (FIG. 11B) show a progressive increase in COX2 protein levels with increasing time of homocysteine exposure. The corresponding mean data obtained from densitometric analysis show that significantly high levels are reached within two hours of homocysteine exposure that further increases at four hours of treatment. Immunoblot analysis with β-tubulin confirms that equal amount of total protein was analyzed in each case. Estimation of PGE2 levels released from the cultured neurons into the medium following L-homocysteine treatment (50 μM) show significant increase in PGE2 levels within two hours of homocysteine exposure that increases considerably at four hours. (FIG. 11C).

Homocysteine-Induced cPLA2 Activity, COX2 Protein Level and PGE2 Release is Dependent on GluN2A-NMDAR Stimulation To determine the role of NMDARs in modulating cPLA2 activity following exposure to homocysteine, neurons were treated with L-homocysteine (50 μM, four hours) in the presence of the NMDAR inhibitor MK801 (10 μM). FIG. 12A shows that homocysteine-mediated increase in cPLA2 activity is blocked in the presence of MK801. To delineate the role of GluN2A-NMDAR and GluN2B-NMDAR in homocysteine-induced increase in cPLA2 activity, neurons were treated with L-homocysteine (50 μM, four hours) in the presence of NVP-AAM077 (30 nM) or Ro 25-6981 (1 μM), selective inhibitors of GluN2A-NMDAR and GluN2B-NMDAR, respectively. FIG. 12B shows that co-incubation with NVP-AAM077 inhibits homocysteine-mediated increase in cPLA2 activity. In contrast, treatment with Ro 25-6981 fails to attenuate homocysteine-mediated increase in cPLA2 activity (FIG. 12C). To further confirm the role of GluN2A-NMDAR in homocysteine-mediated increase in cPLA2 activity, neuronal cultures obtained from WT and GluN2A-KO mice were subjected to L-homocysteine treatment for four hours. FIG. 12D shows that following homocysteine treatment, cPLA2 activity increase significantly in the neuron cultures obtained from WT mice, while cPLA2 activity remain unchanged in the neuron cultures obtained from GluN2A-KO mice.

To determine the role of NMDARs in homocysteine-induced increase in COX2 expression, cell lysates from neuronal cultures treated with L-homocysteine (50 μM, four hours) in the presence of MK801 were subjected to immunoblot analysis with anti-COX2 antibody. The results show that co-incubation with MK801 blocks homocysteine induced COX2 protein expression (FIG. 13A). Subsequent studies investigated the effect of GluN2A-NMDAR (NVP-AAM077, 30 nM) or GluN2B-NMDAR (Ro 25-6981, 1 μM) inhibition on the homocysteine-NMDAR induced increase in COX2 protein level. FIG. 13B shows that treatment with NVP-AAM007 blocks homocysteine-induced increase in COX2 protein expression, while treatment with Ro 25-6981 fails to ameliorate homocysteine-induced increase in COX2 protein level. Consistent with these observations, studies in neuron cultures obtained from WT and GluN2A-KO mice shows that exposure to L-homocysteine (50 μM, four hours) leads to increase in COX2 protein level in WT mice cultures, while it fails to augment COX2 protein expression in GluN2A-KO mice cultures (FIG. 13C).

To evaluate whether the GluN2A-NMDAR stimulation also play a role in homocysteine-dependent PGE2 release, culture media from neurons treated with L-homocysteine (50 μM, four hours) in the absence or presence of DL-AP5, MK801, NVP-AAM077, or Ro 25-6981 were analyzed for PGE2 level. FIG. 14 and FIG. 15 shows that homocysteine-induced increase in PGE2 release is significantly reduced in the presence of DL-AP5 (FIG. 14A), MK801 or NVP-AAM007 (FIG. 15A, B). However, treatment with Ro 25-6981 fails to alter homocysteine-induced increase in PGE2 level (FIG. 15C). Additional studies in neuronal cultures from WT and GluN2A-KO mice show that exposure to homocysteine (50 μM, four hours) significantly increases PGE2 release from WT mice cultures, while it fails to induce PGE2 release from cultures obtained from GluN2A-KO mice (FIG. 15D). These findings in conjunction with the observations in FIGS. 12 and 13 indicate that homocysteine-induced up-regulation of GluN2A-NMDARs plays a key role in cPLA2 activation, COX2 expression and PGE2 release.

Homocysteine-GluN2A-NMDAR Induced cPLA2 Activation and COX2 Expression Involves Crosstalk Between ERK and p38 MAPK To test the hypothesis that homocysteine-GluN2A-NMDAR induced crosstalk between ERK and p38 MAPK plays a role in the increase in cPLA2 activity, COX2 protein levels and subsequent PGE2 release, the effect of pharmacological inhibition of ERK and p38 MAPK were evaluated. Neurons were treated with L-homocysteine (50 μM, four hours) in the presence of selective inhibitors for ERK MAPK phosphorylation (PD98059, 15 μM; FIG. 24) or p38 MAPK phosphorylation (SB203580, 5 μM; FIG. 25). Assessment of cPLA2 activity in cell lysates shows that treatment with PD98059 during exposure to homocysteine significantly attenuates homocysteine-mediated increase in cPLA2 activity (FIG. 24A). Immunoblot analysis of cell lysates with anti-COX2 antibody show that homocysteine-induced COX2 protein expression is significantly reduced in the presence of PD98059 (FIG. 24B). PGE2 level in the culture medium also decreases significantly following exposure to homocysteine in the presence of PD98059 (FIG. 24C). Inhibition of p38 MAPK with SB203580 also shows significant reduction in homocysteine-mediated increase in cPLA2 activity (FIG. 25A), COX2 protein levels (FIG. 25B) and PGE2 release (FIG. 25C).

Homocysteine-Induced COX2 Expression Involves p38 MAPK Mediated Activation of NFκB Both ERK and p38 MAPKs are involved in NF-κB mediated regulation of inflammatory mediators in different cell types. To clarify the role NF-κB in homocysteine-GluN2A NMDAR induced activation of the COX2/PGE2 signaling pathway and the role of MAPKs in this process, the effect of homocysteine on IκB degradation was evaluated. Neurons were treated with L-homocysteine (50 μM, four hours) in the presence of ERK or p38 MAPK inhibitor. Immunoblot analysis of cell lysates with anti-IκB antibody shows that treatment with homocysteine (50 μM, four hours) alone led to significant decrease in the cellular level of IκB, indicating increased IκB degradation and NF-κB activation (FIG. 26A, lane 2). In contrast, exposure to homocysteine in the presence of ERK inhibitor or p38 MAPK inhibitor effectively blocks homocysteine induced degradation of IκB (FIG. 26A, lanes 3-4). In additional studies, neurons were incubated with homocysteine (50 μM, four hours) in the presence of Bengamide B (500 nM), a potent inhibitor of NF-κB activation. Immunoblot analysis shows that co-incubation with Bengamide B attenuates homocysteine-induced increase in COX2 protein level. Quantitative determination of PGE2 release in the culture medium obtained from the same experiment shows significant decrease in PGE2 level following exposure to homocysteine in the presence of Bengamide B (FIG. 26C). To further confirm that the release of PGE2 is a consequence of homocysteine-induced increase in COX2 protein expression, neurons were treated with L-homocysteine (50 μM, four hours) in the presence of CAY10404 (100 nM), a selective inhibitor of COX2. FIG. 26D shows that homocysteine-induced PGE2 release is significantly reduced in the presence of CAY10404.

Homocysteine Induces Sustained Increase in Intracellular $Ca^{2+}$ Level in Cortical Neurons To examine the changes in intracellular $Ca^{2+}$ dynamics, rat neuronal cultures were loaded with Fura2-AM and treated with L-homocysteine (50 µM, 60 minutes). FIG. 28A shows $Ca^{2+}$ responses (in false color maps) in a representative group of cells treated with homocysteine. The temporal profile of Fura2 fluorescence ratio measured in the soma of 20 individual neurons (FIG. 28B) and their mean data (FIG. 28C) illustrates a slow and progressive increase over time, when compared to the unstimulated cells (control). Quantification of $Ca^{2+}$ changes further show that intracellular $Ca^{2+}$ concentration ($[Ca^{2+}]_i$) remain unchanged in the control cells, whereas treatment with homocysteine results in significant increase in $[Ca^{2+}]_i$ over time with a maximum increase of approximately 7.2 folds by 60 minutes when compared to corresponding control cells (FIG. 28D). In contrast, neurons treated with the NMDAR agonist, glutamate (50 µM, 10 minutes) show a rapid change in Fura2 fluorescent ratio and an approximately 21-fold increase in $[Ca^{2+}]_i$ within 2.5 minutes, which then declines progressively with time (FIG. 28E, F). In neurons where the soma and its main dendritic process (out to at least 40 µm) were identifiable, the temporal profile of $[Ca^{2+}]_i$ increase in the processes were further analyzed following exposure to homocysteine. The findings show a slow and progressive increase in both Fura2 fluorescent ratio and $[Ca^{2+}]_i$ in the processes over time (FIG. 28G, H). A comparison of the progressive change in $[Ca^{2+}]_i$ between somata and processes show a similar profile (FIG. 28I, J).

Homocysteine-Induced Increase in Intracellular $Ca^{2+}$ Level is Dependent on GluN2A Containing NMDAR To determine the primary source of $[Ca^{2+}]_i$ increase, neurons were exposed to L-homocysteine (50 µM, 60 minutes) in the presence of the $Ca^{2+}$ chelator EGTA. FIG. 29(A-D) shows that homocysteine-mediated increase in Fura2 fluorescence ratio and $[Ca^{2+}]_i$ level are blocked in the presence of EGTA in both somata and processes, suggesting that homocysteine mediated $[Ca^{2+}]_i$ increase is derived from extracellular sources. To examine the role of NMDARs in homocysteine-mediated $Ca^{2+}$ influx, neurons were treated with L-homocysteine (50 µM, 60 minutes) in the presence of NMDAR inhibitor DL-AP5. FIG. 29(E-H) shows that DL-AP5 attenuates homocysteine-induced increases in Fura2 fluorescence ratio and $[Ca^{2+}]_i$ in both the somata and processes.

To evaluate the role of GluN2A- and GluN2B containing NMDARs in homocysteine-induced $Ca^{2+}$ influx, rat neuronal cultures were incubated with L-homocysteine (50 µM, 60 minutes) in the presence of selective antagonists for GluN2A subunit (NVP-AAM077) or GluN2B subunit (Ro 25-6981). FIG. 30(A-D) shows that co-incubation with NVP-AAM077 attenuates homocysteine-induced increase in Fura2 fluorescence ratio and $[Ca^{2+}]_i$ in both somata and processes. In contrast, exposure to Ro 25-6981 fails to attenuate homocysteine-induced $[Ca^{2+}]_i$ increase in either the somata or processes (FIG. 30E-H). To establish more directly the role of GluN2A-NMDAR in homocysteine-induced $[Ca^{2+}]_i$, neuronal cultures obtained from WT and GluN2A KO mice were treated with L-homocysteine (50 µM, 60 min). FIG. 31 (A-C, G, H) shows progressive increase in Fura2 fluorescence ratio and $[Ca^{2+}]_i$ in both the somata and processes of neurons from WT mice as compared to control cells. However, treatment of neurons from GluN2A KO mice with homocysteine fails to increase Fura2 fluorescence ratio or $[Ca^{2+}]_i$ in the somata and processes (FIG. 31D-F, I, J), when compared to control cells. In contrast, treatment with glutamate (50 µM) leads to rapid increase in Fura2 fluorescence ratio and $[Ca^{2+}]_i$ in neurons from both WT and GluN2A-KO mice (FIG. 32). Additional studies evaluating the protein expression of GluN1, GluN2A, and GluN2B subunits in neuronal lysates from WT and GluN2A KO mice show no change in the protein level of GluN1 subunit. The findings also confirm the loss of expression of GluN2A subunit in the neurons from GluN2A KO mice. However, neuronal GluN2B subunit expression goes up substantially in the GluN2A KO mice.

Homocysteine-Induced Stimulation of GluN2A Containing NMDAR Leads to Sustained ERK MAPK Phosphorylation and Neuronal Death Sustained increase in ERK MAPK phosphorylation is involved in promoting homocysteine-NMDAR induced neuronal cell death. To evaluate the role of GluN2A-NMDAR in homocysteine-induced ERK MAPK phosphorylation, rat neuronal cultures were treated with L-homocysteine (50 µM) for 30 minutes or 60 minutes in the presence of DL-AP5 (NMDAR inhibitor) or NVP-AAM077 (GluN2A inhibitor). FIG. 22A and FIG. 22B show that pharmacological inhibition with either DL-AP5 or NVP-AAM077 attenuates homocysteine-induced ERK MAPK phosphorylation at both the time points. To further confirm the role of GluN2A-NMDAR in homocysteine-induced ERK MAPK phosphorylation, neuron cultures from WT and GluN2A KO mice were treated with L-homocysteine (50 µM) for 30 minutes or 60 minutes. FIG. 33C shows that treatment with homocysteine leads to sustained increase in ERK MAPK phosphorylation in neurons obtained from WT mice, while it fails to induce ERK MAPK phosphorylation in neurons obtained from GluN2A KO mice. Subsequent studies evaluated the effect of glutamate (50 µM) on the temporal profile of ERK MAPK phosphorylation (5 minutes, 30 minutes, or 60 minutes) in rat neuron cultures. FIG. 33D shows that treatment with glutamate leads to rapid but transient increase in ERK MAPK phosphorylation within five minutes of stimulation, which returns to basal level by 30 minutes. Treatment with DL-AP5 blocks, while treatment with NVP-AAM077 fails to ameliorate, glutamate-induced transient increase in ERK MAPK phosphorylation at five min (FIG. 33E), indicating that GluN2A-NMDAR does not play a role in glutamate-induced ERK MAPK phosphorylation. Consistent with this interpretation, studies in neuron cultures from WT and GluN2A-KO mice shows that exposure to glutamate (50 µM) leads to rapid but transient increase in ERK MAPK phosphorylation in both WT and GluN2A-KO mice cultures (FIG. 33F).

To evaluate the role of GluN2A-NMDARs in homocysteine-induced neuronal cell death, rat neuronal cultures were treated with L-homocysteine (50 µM, 18 h) in the presence of NVP-AAM077. Cell death was assessed by Hoechst DNA staining, an early indicator of apoptosis. The representative photomicrographs and quantitative analysis of pyknotic nuclei show a significant increase in cell death following exposure to homocysteine (FIG. 34A). Pharmacological Treatment with NVP-AAM077 Significantly Reduces Homocysteine-Induced Neuronal Death (FIG. 34A).

To assess the role of ERK MAPK activation in homocysteine-GluN2A NMDAR-induced neurotoxicity, neurons were treated with L-homocysteine (50 µM, 18 hours) in the presence of the ERK MAPK inhibitor, PD98059 (15 µM). FIG. 34A shows ERK MAPK inhibition also attenuates homocysteine-induced neurotoxicity. Additional studies in neuron cultures obtained from WT and GluN2A-KO mice show that exposure to homocysteine (50 µM) significantly increases neuronal death in cultures obtained from WT mice, while it fails to induce neurotoxicity in cultures obtained from GluN2A KO mice (FIG. 34B). The findings also show that homocysteine-induced neurotoxicity observed in neurons from WT mice is significantly reduced in the presence of ERK MAPK inhibitor (FIG. 34B). In contrast, glutamate (50 µM) induced neuronal cell death in rat neuron cultures remain unaffected by pharmacological inhibition of either GluN2A-NMDAR or ERK MAPK (FIG. 34C). A comparison of the neurotoxic effects of glutamate in neuron cultures obtained from WT and GluN2A-KO mice further show that deletion of GluN2A subunit of NMDAR fails to reduce the neurotoxic effects of glutamate (FIG. 34D). Pharmacological inhibition of ERK MAPK also fails to reduce glutamate-induced neurotoxicity in neurons from either WT or GluN2A KO mice (FIG. 34D).

This disclosure therefore shows that homocysteine-GluN2A NMDAR signaling pathway in neurons triggers a proinflammatory response that involves release of PGE2. The findings show that homocysteine-GluN2A-NMDAR stimulation increases cPLA2 activity and COX2 protein expression, the combined action of which result in enhanced PGE2 biosynthesis and release. Complementary studies using GluN2A-NMDAR KO mice confirm the role of GluN2A-NMDAR in homocysteine-mediated PGE2 release. This disclosure reveals for the first time a novel role of GluN2A-NMDAR in promoting neuroinflammation, which is particularly important in the field of NMDAR signaling, as GluN2A-NMDARs have been so far only implicated in neuronal survival and synaptic plasticity.

Another finding of the current study is that the homocysteine-induced increase in the biosynthesis and subsequent release of the proinflammatory prostanoid PGE2 from neurons is time-dependent. Stimulation of GluN2A-NMDAR leads to concomitant up-regulation of cPLA2 activity and COX2 expression, two enzymes involved in PGE2 synthesis. The concerted regulation of cPLA2 and COX2 by GluN2A-NMDAR involves crosstalk between ERK and p38 MAPKs. The findings highlight the role of GluN2A-NMDAR in regulating PGE2 release from neurons and a schematic representation of this signaling pathway is presented in FIG. 27.

Cyclooxygenases catalyze the first committed step in the formation of prostaglandins from arachidonic acid. The two isoforms of cyclooxygenase, COX1 and COX2 are enzymatically indistinguishable but differ in their expression levels, distribution, and transcriptional regulation. In the brain, COX1 expression levels are low in all regions and in all cell types, including neurons and astrocytes. In contrast, COX2, the inducible isoform is expressed in high levels in specific populations of neurons of cerebral cortex, hippocampus, amygdala and hypothalamus. The cyclooxygenases catalyze the formation of the prostaglandin precursor Prostaglandin H2 from arachidonic acid, which serves as the substrate for the synthesis of biologically active prostanoids (e.g., PGE2, PGD2, PGF2α, PGI2) by specific prostaglandin synthases. Although COX2 may be involved in synaptic plasticity, increased COX2 expression also may trigger distinct proinflammatory signals and may be involved tissue damage during early phase of acute inflammatory response. Furthermore, unregulated COX2 expression influences chronic inflammatory conditions. In brain, COX2 appears to be the dominant source of prostaglandin formation during inflammation and PGE2 is one of the most abundant prostaglandins produced in the body. Although PGE2 can mediate many biological functions, deregulation of PGE2 synthesis, leading to either increased amounts or degradation of PGE2, is associated with multiple pathological conditions. This disclosure presents data showing that increased levels of homocysteine induce COX2 expression and subsequent PGE2 release in cultured cortical neurons, suggesting that hyperhomocysteinemia may contribute to the inflammatory milieu of the brain by inducing proinflammatory mediators and thereby promoting the pathology of neurodegenerative diseases. Since the extent of inflammatory response directly correlates with the severity of ischemic brain damage, these findings provide a basis for the increased ischemic brain injury observed in hyperhomocysteinemic conditions.

The data presented herein show that homocysteine-induced COX2 expression and PGE2 release is mediated by GluN2A-NMDAR stimulation. This strongly supports the notion that GluN2A-NMDAR promotes inflammation and subsequent increase in the pathology of ischemic injury under hyperhomocysteinemic conditions. Moreover, inhibition of GluN2A-NMDAR can reduce inflammation and thereby decrease the pathology of ischemic injury under hyperhomocysteinemic conditions.

The findings that homocysteine-GluN2A-NMDAR stimulation induces pro-inflammatory processes also may influence progression of other neurological diseases and, therefore, reveal other indications for which inhibiting GluN2A-NMDAR may be therapeutically effective. Hyperhomocysteinemia has been associated with multiple neurological disorders including, but not limited to, Parkinson's disease, multiple sclerosis, amyotrophic lateral sclerosis, mild cognitive impairment, and Alzheimer's disease. Inflammation may influence the progression and/or severity of each of these diseases and as such, inhibiting GluN2A-NMDAR-mediated inflammation may inhibit the progression and/or decrease the severity of each of these diseases.

This disclosure provides data establishing the role of GluN2A-NMDAR in triggering neuroinflammation. NMDARs include heteromeric assemblies of GluN1/GluN2A, GluN1/GluN2B, or GluN1/GluN2A/GluN2B subunits. The subunit composition determines the function of the receptor. GluN2B-NMDAR stimulation following excessive release of glutamate in the brain results in long-term depression and excitotoxicity. On the other hand, GluN2A-NMDAR stimulation by glutamate has been generally implicated in synaptic plasticity and promoting cell survival. However, homocysteine-mediated GluN2A-NMDAR stimulation leads to sustained activation of ERK MAPK resulting in neurotoxicity, emphasizing that GluN2A-NMDAR could play dual roles determining neuronal survival or death depending on the nature of the agonist. The data presented in this disclosure show that homocysteine preferentially stimulates GluN2A-NMDAR subtype to also induce pro-inflammatory signaling pathways. Thus, inhibiting GluN2A-NMDAR, and the consequent GluN2A-NMDAR-mediated inflammation, can decrease the neuroinflammation and neurotoxicity in hyperhomocysteinemic conditions.

The above finding is especially important in the field of NMDAR signaling since the subunit composition of NMDARs can determine whether NMDAR-mediated signaling has beneficial or detrimental effects in neurons. The detrimental signaling cascade downstream of homocysteine-mediated GluN2A-NMDAR stimulation involves a crosstalk between ERK and p38 MAPKs where AMPARs play an intermediary role (FIG. 27). The data presented herein highlight the role of homocysteine-mediated GluN2A-NMDAR stimulation in triggering a pro-inflammatory response involving cPLA2/COX2-dependent PGE2 release. The role of GluN2A-NMDAR in neuronal PGE2 release is not only based on selective pharmacological inhibition of GluN2A-subunit, but also by using GLuN2A-KO mice. The inability of a GluN2B-NMDAR inhibitor to attenuate the activation of cPLA2/COX2 signaling pathway and PGE2 release further confirms the selective role of GluN2A-NMDARs in mediating the detrimental effects of homocysteine in neurons. Thus, these findings modify the current perception that GluN2A-NMDAR-mediated signaling in neurons exclusively enhances plasticity and survival promoting genes.

Phosphorylation of cPLA2 at $Ser^{505}$ by either ERK or p38 MAPK augments cPLA2 activity and the specific MAPK involved in this process depends on the type of stimulus. Also, depending on the stimuli and cell type, ERK or p38 MAPK can enhance the transcription and/or stability of COX2 mRNA, resulting in increased protein levels. The data presented herein show inhibition of either ERK or p38 MAPK can attenuate homocysteine-GluN2A NMDAR-induced enhanced cPLA2 activity and COX2 protein level. Since homocysteine-GluN2A NMDAR-mediated p38 MAPK activation is downstream of, and dependent on, ERK MAPK activation, sequential activation of either ERK or p38 MAPK is involved in activating cPLA2/COX2 signaling pathway in neurons following exposure to homocysteine. These findings reveal an important additional mechanism of regulation for the cPLA2/COX2 pathway that involves concerted effort of both ERK and p38 MAPK. Consistent with this interpretation, inhibition of both ERK and p38 MAPK blocks the degradation of IκB that is known to result in activation of NFκB signaling cascade, a major stress response pathway for COX2 gene expression. Our findings also show that pharmacological inhibition of NFκB attenuates homocysteine-induced increase in COX2 protein level and PGE2 release. Together these findings demonstrate that NFκB activation plays an intermediary role in ERK-dependent and p38 MAPK-dependent COX2 expression, and provides a molecular basis for homocysteine-GluN2A NMDAR mediated release of PGE2 from neurons.

Homocysteine also leads to progressive increase in expression and release of the monocyte chemoattractant protein-1 (MCP-1) from neurons (FIG. 35). Inhibition of GluN2A-NMDAR with NVP-AAM077 or DL-AP5 attenuates the expression and release of MCP-1 (FIG. 36), indicating that homocysteine-induced MCP-1 release is mediated through GluN2A-NMDAR stimulation. MCP-1 is a member of the CC chemokine family and regulates migration and infiltration of monocytes/macrophages. MCP-1 is produced by a variety of cell types in response to different stimuli and has been shown to be involved in several diseases such as, for example, atherosclerosis, rheumatoid arthritis, and insulin-resistant diabetes. However, the role of MCP-1 in ischemic brain injury is not completely understood.

In subsequent studies both control (normal homocysteine) and hyperhomocysteinemic rats were exposed to a mild ischemic insult (MCAO, 60 minutes) followed by reperfusion. The mild ischemic insult under hyperhomocysteinemic condition leads to a significant increase in the level of both PGE2 and MCP-1 in the ischemic hemisphere, when compared to the control or sham (no stroke) animals (FIG. 37). The increase in PGE2 and MCP-1 level is observed within six hours of reperfusion in both the cortex and the striatum. Pharmacological inhibition of GluN2A-NMDAR with intravenous administration of NVP-AAM077 (1.2 mg/kg body weight) at the onset of the insult attenuated the increase in the level of both PGE2 and MCP-1 (FIG. 37).

Thus, this disclosure presents the novel concept that homocysteine-induced GluN2A-NMDAR stimulation triggers the release of PGE2 and/or MCP-1, two pro-inflammatory mediators, from neurons. Excessive or persistent release of PGE2 in the brain has been associated with microglial activation, which is a major source for the production of pro-inflammatory cytokines and matrix metalloproteinases. This in turn could lead to blood-brain barrier disruption and peripheral immune cell infiltration, resulting in an inflammatory response that has been associated with the progression of both acute and chronic neurological disorders. Increased MCP-1 has been associated with infiltration of leucocytes, particularly monocytes, following blood brain barrier disruption, resulting in recruitment of leukocytes into the ischemic hemisphere. Therefore, a neurological insult under hyperhomocysteinemic conditions can contribute to the inflammatory milieu of the brain through induction of PGE2 and/or MCP-1 release from neurons. The subsequent microglial activation and peripheral immune cell infiltration can accelerate and/or exacerbate brain injury.

This disclosure also provides data demonstrating the role of GluN2A-NMDAR in homocysteine-induced $Ca^{2+}$ influx. $Ca^{2+}$ is an important intracellular messenger that regulates multiple neuronal functions including cellular growth, membrane excitability, and synaptic activity. As such, intracellular $Ca^{2+}$ level in neurons is tightly regulated to ensure efficient control on downstream signaling cascades involved in maintaining cellular physiology. The cellular mechanisms that help maintain $Ca^{2+}$ homeostasis include transmembrane $Ca^{2+}$ gradient, the route of $Ca^{2+}$ entry, and the presence of various $Ca^{2+}$ buffering and extrusion systems. Any changes in these homeostatic control mechanisms under pathological condition can lead to an aberrant increase in intracellular $Ca^{2+}$ level.

Overactivation of NMDARs in neurodegenerative disorders involving excessive release of glutamate may lead to aberrant increase in $[Ca^{2+}]_i$ level. However, the extent of $Ca^{2+}$ increase varies depending on the severity of the stimuli and NMDAR subunit composition. A moderate and transient influx of $Ca^{2+}$ has been coupled to GluN2A-NMDAR, while rapid large $Ca^{2+}$ overload is associated with GluN2B-NMDAR. Glutamate-mediated intracellular $Ca^{2+}$ increases can occur in two phases, a rapid but low level of initial increase followed by a delayed larger increase. The larger delayed increase in $[Ca^{2+}]_i$ can be blocked by selective antagonists of GluN2B-NMDAR, indicating that the initial smaller $Ca^{2+}$ influx is dependent on GluN2A-NMDAR.

Thus, the sole role of GluN2A-NMDAR in homocysteine-induced low level of $Ca^{2+}$ influx is not only confirmed using a selective pharmacological inhibitor for GluN2A-NMDAR, but also by genetic deletion of GluN2A-subunit of NMDAR. The inability of homocysteine to induce $[Ca^{2+}]_i$ increase in neurons obtained from GluN2A-KO mice, in spite of the higher expression of the GluN2B-subunit of NMDAR, further emphasizes the contribution of GluN2A-NMDARs in homocysteine-induced $[Ca^{2+}]_i$ influx. In this context, GluN1/2B NMDARs undergo rapid desensitization upon exposure to homocysteine while GluN1/2A receptors do not exhibit desensitization.

The distinctly different contribution of GluN2A-containing and GluN2B-containing NMDARs in homocysteine-mediated and glutamate-mediated $[Ca^{2+}]_i$ influx suggests differential role of these subunits in regulating intracellular signaling cascades. This interpretation is substantiated by findings that homocysteine-mediated NMDAR stimulation leads to sustained increase in ERK MAPK phosphorylation, which is completely blocked by pharmacological inhibition of GluN2A-NMDAR or genetic deletion of GluN2A subunit. In contrast, in the glutamate treatment paradigm, an increase in ERK MAPK phosphorylation is found to be rapid but transient, which remains unaffected by pharmacological inhibition or genetic deletion of GluN2A-NMDAR. This difference in ERK MAPK signaling by the two NMDAR agonists has considerably different effect on the neurotoxic profile. Pharmacological inhibition GluN2A-NMDAR or genetic deletion of GluN2A subunit as well as pharmacological inhibition of ERK MAPK activity attenuates homocysteine-induced neuronal death, while they fail to attenuate glutamate-induced neuronal cell death. The findings highlight the role of sustained ERK MAPK activation in GluN2A-NMDAR mediated neurotoxicity.

Sustained ERK MAPK activation leads to a decrease in surface expression of GluA2 subunit of AMPA receptor (α-Amino-3-hydroxy-5-methyl-4-isoxazolepropionic acid), resulting in $Ca^{2+}$ influx through GluA2-lacking $Ca^{2+}$-permeable AMPA receptors, which leads to p38 MAPK activation. This interplay between ERK and p38 MAPK results in caspase-3 dependent neuronal cell death. The transient increase in ERK MAPK phosphorylation following exposure to glutamate and its inability to attenuate glutamate-induced neurotoxicity further indicate that transient ERK MAPK activation has different consequences as compared to sustained activation.

Thus, this disclosure describes the role of increased $[Ca^{2+}]_i$ in homocysteine-induced neurotoxicity at homocysteine levels generally observed in individuals predisposed to mild to moderate hyperhomocysteinemia. Together these findings present the novel concept that homocysteine-mediated stimulation of GluN2A-NMDARs may promote neurotoxicity through sustained activation of $Ca^{2+}$-dependent ERK MAPK signaling.

Thus, in one aspect, this disclosure describes a method for treating a hyperhomocysteinemic subject having ischemic stroke. Generally, the method includes administering to a hyperhomocysteinemic subject suffering from ischemic stroke a composition that includes an inhibitor or antagonist of GluN2A-NMDAR in an amount that ameliorates brain infarct size and/or improve functional outcome.

In another aspect, this disclosure describes a method for treating a hyperhomocysteinemic subject having a neurological disorder in which homocysteine-induced neuroinflammatory response exacerbates brain injury under hyperhomocysteinemic conditions. Exemplary neurological disorders include ischemic stroke, traumatic brain injury, and vascular dementia. Generally, the method includes administering to a hyperhomocysteinemic subject suffering from such a neurological disorder a composition that includes an inhibitor or antagonist of GluN2A-NMDAR in an amount that reduces prostaglandin E2-mediated neuroinflammation.

The GluN2A-NMDAR inhibitor or antagonist may be any suitable compound that inhibits GluN2A-NMDAR signaling or is an antagonist of GluN2A-NMDAR. In some embodiments, the GluN2A-NMDAR inhibitor may be NVP-AAM077 (also known as PEAQX; ({[(1S)-1-(4-bromophenyl)ethyl]amino}-(2,3-dioxo-1,4-dihydroquinoxalin-5-yl)methyl)phosphonic acid; and CAS 459836-30-7). In some embodiments, the GluN2A-NMDAR antagonist may be ST3 ({(S)-5-[(R)-2-amino-2-carboxyethyl]-1-[4-(3-fluoropropyl) phenyl]-4,5-dihydro-1H-pyrazole-3-carboxylic acid}), ST1 {(S)-5-[(R)-2-amino-2-carboxyethyl]-1-(4-fluorophenyl)-4,5-dihydro-1H-pyrazole-3-carboxylic acid}), ST6 ({(S)-5-[(R)-2-amino-2-carboxyethyl]-1-(4-bromophenyl)-4,5-dihydro-1H-pyrazole-3-carboxylic acid}) FRA-19 ({(S)-5-[(R)-2-amino-2-carboxyethyl]-1-phenyl-4,5-dihydro-1H-pyrazole-3-carboxylic acid}), MPX-004 (5-(((3-chloro-4-fluorophenyl)sulfonamido)methyl)-N-((2-methylthiazol-5-yl)methyl)pyrazine-2-carboxamide), TCN-201 (3-chloro-4-fluoro-N-[(4-{[2-phenylcarbonyl)hydrazine]carbonyl}phenyl)methyl}benzenesulfonamide)), MPX-007 ((5-(((3,4-difluorophenyl)sulfonamido)methyl)-6-methyl-N-((2-methylthiazol-5-yl)methyl)pyrazine-2-carboxamide), or a derivative of TCN-201.

The GluN2A-NMDAR inhibitor may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with GluN2A-NMDAR inhibitor without causing any undesirable biological effects or interacting in a deleterious manner with any of the other components of the pharmaceutical composition in which it is contained.

The GluN2A-NMDAR inhibitor may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, the GluN2A-NMDAR inhibitor may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a stabilizer, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the GluN2A-NMDAR inhibitor into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of GluN2A-NMDAR inhibitor administered can vary depending on various factors including, but not limited to, the weight, physical condition, and/or age of the subject, and/or the route of administration. Thus, the absolute weight of GluN2A-NMDAR inhibitor included in a given unit dosage form can vary widely, and depends upon factors such as the species, age, weight and physical condition of the subject, and/or the method of administration. Accordingly, it is not practical to set forth generally the amount that constitutes an amount of GluN2A-NMDAR inhibitor effective for all possible applications. Those of ordinary skill in the art, however, can readily determine the appropriate amount with due consideration of such factors.

In some embodiments, the method can include administering sufficient GluN2A-NMDAR inhibitor to provide a dose of, for example, from about 100 ng/kg to about 50 mg/kg to the subject, although in some embodiments the methods may be performed by administering GluN2A-NMDAR inhibitor in a dose outside this range. In some of these embodiments, the method includes administering sufficient GluN2A-NMDAR inhibitor to provide a dose of from about 10 µg/kg to about 5 mg/kg to the subject, for example, a dose of from about 100 µg/kg to about 2 mg/kg. In some embodiments, the method includes administering sufficient GluN2A-NMDAR inhibitor to provide a dose of from about 0.5 mg/kg to 2.0 mg·kg, such as, for example, a dose of about 1.2 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: $m^2=(wt\ kg^{0.425} \times height\ cm^{0.725}) \times 0.007184$.

In some embodiments, the method can include administering sufficient GluN2A-NMDAR inhibitor to provide a dose of, for example, from about 0.01 mg/m$^2$ to about 10 mg/m$^2$.

In some embodiments, the GluN2A-NMDAR inhibitor may be administered, for example, from a single dose to multiple doses per week, although in some embodiments the method can be performed by administering GluN2A-NMDAR inhibitor at a frequency outside this range. When multiple doses are used within a certain period, the amount of each dose may be the same or different. For example, a dose of 1 mg per day may be administered as a single dose of 1 mg, two 0.5 mg doses, or as a first dose of 0.75 mg followed by a second dose of 0.25 mg. Also, when multiple doses are used within a certain period, the interval between doses may be the same or be different.

In certain embodiments, GluN2A-NMDAR inhibitor may be administered as a once off treatment. In other embodiments, the method may be practiced by administering multiple doses of the GluN2A-NMDAR inhibitor. Typically, when multiple doses are administered, all doses are administered within 72 hours of the initial dose.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials and Reagents:

L-homocysteine thiolactone hydrochloride was obtained from Sigma-Aldrich (St. Louis, Mo.). Selective pharmacological inhibitors were: Ro 256981 was purchased from Tocris Bioscience (Bristol, United Kingdom) and NVP-AAM077 ([(R)-[(S)-1-(4-bromo-phenyl)-ethylamino]-(2,3-dioxo-1,2,3,4-tetrahydro-quinoxalin-5-yl)-methyl]phosphonic acid) was a gift from Dr. Yves P. Auberson, Novartis International AG (Basel, Switzerland). Male Wistar rats were purchased from Envigo Corporation (Huntingdon, United Kingdom). Rats were maintained in a 12-hour light/dark vivarium (light off at 18.00 h) and with access to food and water ad libitum. GluN2A-NMDAR knockout mice (GluN2A-KO) generated as previously described (Sakimura et al., 1995, *Nature* 373:151-155) and were obtained from Dr. Andrew Holmes, NIH/NIAAA, (Rockville, Md.). All experiments were performed in accordance with protocols approved by the Institutional Animal Care Committee of University of New Mexico and were in compliance with the ARRIVE guidelines.

Development of Hyperhomocysteinemic Rat and Mouse Models

L-homocysteine (200 mM) was freshly prepared by alkali hydrolysis of L-homocysteine thiolactone hydrochloride followed by neutralization, and maintained in 0.02 mM of N-Tris(hydroxymethyl)methyl-2-aminoethanesulfonic acid buffer pH 7.4 as previously described (Poddar et al., 2001, *Circulation*, 103:2717-2723). Osmotic pumps (Alzet, 2ML1, flow rate 10 µl/hr; Durect Corp., Cupertino, Calif.) containing either 2 ml of freshly prepared 200 mM L-homocysteine (for hyperhomocysteinemia) or normal saline (for control) were surgically implanted subcutaneously on the back and posterior to the scapulae of male Wistar rats under anesthesia (2% isoflurane in medical grade oxygen). The incision was closed after implantation and the rats were allowed to recover in their cage. For both WT and GluN2A-KO mice, osmotic pumps (Alzet, 2001, flow rate 1 µl/hr; Durect Corp., Cupertino, Calif.) containing either 200 µl of freshly prepared 200 mM L-homocysteine (for hyperhomocysteinemia) or normal saline (for control) were implanted similarly.

Measurement of Total Plasma Homocysteine in Rats and Mice

Blood was obtained from rats (retro-orbital) and mice (cardiac puncture) under anesthesia with 2% isoflurane in medical grade oxygen, before installation of osmotic pumps (0 day) and at various time points after installation of osmotic pumps (rats: day 3, day 5, and day 7; mice: day 3 and day 5). Blood was collected in standardized VACUTAINER venous blood collection EDTA-tubes (ThermoFisher Scientific, Inc., Waltham, Mass.) and centrifuged at 3,500 rpm for 15 minutes. The plasma obtained was analyzed for total plasma homocysteine levels using high performance liquid chromatography with post-column fluorescence detection as previously described (Gilfix et al., 1997, *Clin Chem* 43:687-688; Jacobsen et al., 1994, *Clin Chem* 40:873-881; Miller et al., 2013, *Am J Clin Nutr* 97:827-834).

Induction of Transient Focal Cerebral Ischemia

Middle cerebral artery occlusion (MCAO) was performed on both male rats and mice. For rat studies, control and hyperhomocysteinemic male Wistar rats (8-9 weeks, 290-295 g) were subjected to MCAO under anesthesia (2% isoflurane in medical grade oxygen), using the intraluminal method as previously described (Candelario-Jalil, E., et al., 2004, *Brain Res* 1007:98-108; Deb et al., 2013, *J Neurosci* 33:17814-17826). Briefly, the right common carotid artery (CCA) was exposed through an incision made in the ventral midline neck region. To prevent improper insertion of the occluding filament, both the external carotid artery and pterygopalatine branch of the internal carotid artery were clipped. A silicon-rubber-coated monofilament (403756, Doccol Corp., Sharon, Mass.) was inserted into the internal carotid artery through an incision made in the CCA, 2 mm proximal from the bifurcation of the CCA, and advanced 18-19 mm from the bifurcation, to occlude the origin of the anterior cerebral, middle cerebral, and posterior communicating arteries. The incision was closed and the rats were allowed to recover from anesthesia. A quick assessment of neurological deficit was done immediately prior to reperfusion and only those animals that had more than 50% of contralateral forelimb flexion and walked in circles to the contralateral side were considered for the study, as previously described (Longa et al., 1989, *Stroke* 20:84-91). Following 60 minutes of occlusion, the rats were anesthetized and the filament was gently retracted to allow reperfusion. The incision was closed and the rats were allowed to recover from anesthesia. A subset of control and hyperhomocysteinemic rats received a single intravenous injection of GluN2A-NMDAR selective inhibitor NVP-AAM077 (1.2 mg/kg body weight) through the femoral vein, and another subset received a single intraperitoneal injection of GluN2B-NMDAR inhibitor Ro 256981 (6 mg/kg body weight), as previously described (Chaperon et al., 2003, *Behav Pharmacol* 14:477-87; Fox et al., 2006, *Hippocampus* 16:907-015). Both NVP-AAM077 and Ro 256981 were administered at the onset of ischemic insult. The rats were then subjected to MRI on days 1, 3, and 14 post-MCAO and a series of behavioral tests was performed between days 7-9 post-MCAO.

For studies using WT and GluN2A KO mice (12-14 weeks, 26.5-27.5 g), MCAO was performed by the intraluminal method as described above. A silicon-rubber-coated monofilament (602234, Doccol Corp., Sharon, Mass.) was advanced from an incision in the CCA through the internal carotid artery to a length of 10-11 mm from the bifurcation, occluding the middle cerebral artery. After 30 minutes of MCAO, the filament was removed to allow reperfusion, and the incision was closed. The mice were then subjected to MRI24 hours after the ischemic insult.

Quantitation of Infarct Size and Structural Integrity by MRI

Multimodal MRI of rat brain that includes relaxation time imaging and diffusion imaging was performed at 1, 3 and 14 days after MCAO and reperfusion. The rats were placed in a dedicated holder and positioned in the isocenter of a 4.7-Tesla MRI scanner (Bruker Biospin) that is equipped with a 40-cm bore and a gradient of 660 mT/m at rise time within 120 psec. To obtain good signal-to-noise ratio, a small-bore linear RF coil (inner diameter=72 mm) was used for signal excitation, and a single tuned surface coil (RAPID Biomedical, Rimpar, Germany) was used for signal detection (Sood et al., 2009, *J Cereb Blood Flow Metab* 29:308-316; Taheri, S. and Sood, R., 2007, *Magn Reson Imaging* 25:613-625; Yang et al., 2013 *J Cereb Blood Flow Metab* 33:1104-1114). For mice, the MRI was performed only at day 1. The mice were placed in its dedicated holder of inner diameter 72 mm in the 4.7-Tesla MRI scanner with a 40-cm bore size and a gradient rise time/maximum speed of 9000 T/m/s. During MRI, the rats and mice were kept anesthetized with 2% isoflurane in medical grade oxygen. Respiration and heart rate were monitored continuously and body temperature was maintained at 37.0±0.5° C.

For rats, T2-weighted images were acquired with a rapid acquisition with relaxation enhancement (RARE) sequence of Repetition Time (TR)/Echo Time (TE)=5,000 ms/56 ms, Field of View (FOV)=4 cm×4 cm, slice thickness=1 mm, inter-slice distance=1.1 mm, number of slices=12, matrix=256×256 and number of average=3. For mice, T2 weighted images were acquired with a RARE sequence of Repetition Time/Echo Time=5,000 ms/56 ms, Field of View=4 cm×4 cm, slice thickness=1 mm, number of slices=12, matrix=256×256 and number of average=3. The infarcted area was determined from T2 maps derived from the T2-weighted images by comparing regions of hyperintensity (infarcted or damaged area) and hypointensity (non-infarcted or undamaged area). An observer blinded to the experimental conditions evaluated the volume of ischemic brain damage from the T2 maps. For each slice, regions of hypointensity were highlighted on the ipsilateral side and the area measured. The total area on the contralateral side was also determined. The areas of hypointensity for the ipsilateral side and contralateral side were obtained by adding all slices together and the respective volumes were calculated by multiplying each sum by 1 (thickness of each section). The percentage of infarction volume was calculated as follows: [(volume of contralateral side—noninfarcted volume of the lesioned side)/volume of contralateral side]×100 (Swanson et al., 1990 *J Cereb Blood Flow Metab* 10:290-293).

Multi-slice, multi-shot, diffusion-weighted echo-planar imaging (Repetition Time/Echo Time=3,800 ms/38 ms; b-values=600 and 1,900 s/mm$^2$ in 30 directions; Field of View=4 cm×4 cm, slice thickness=1 mm, matrix=256×256) was performed to assess tissue architecture. Quantitative apparent diffusion coefficient (ADC) maps were calculated on a voxel-wise basis, with a linear least squares fit on the logarithm of the signal intensity versus the b-value for each diffusion direction. Based on the ADC maps, fractional anisotropy (FA) maps were generated using ParaVision 5.1 (Bruker Biospin MRI, Billerica, Mass., USA). Both the ADC and FA values were computed for each slice and averaged over all the slices for the tissue. For MRI study, thirteen rats were subjected to MCAO in the control group, out of which one died within 24 hours. MRI scans were too noisy for one rat on day 1, one rat on day 3 and two rats on day 14. In the hyperhomocysteinemic group, MCAO was performed on twenty-six rats, out of which eleven died within 24 h. MRI scan was too noisy for one rat on day 14. These animals were therefore excluded from the MRI study on those days. In addition, ADC and FA values were not computed for one NVP-AAM077 treated hyperhomocysteinemic rat, as the processed maps were too noisy.

Behavioral Studies

All rats were subjected to a battery of behavioral tests on day 7 (CatWalk), day 8 (cylinder and rotarod tests) and day 9 (adhesive test) after MCAO to evaluate normal gait, motor coordination and sensory motor functions. Habituation and training (3 days) was performed for one week before MCAO. The first two trainings days were before osmotic pump implantation and the third training day was after pump implantation. An experienced observer blinded to the experimental conditions evaluated all behavioral parameters.

Catwalk: An automated quantitative gait analysis system (Catwalk XT 10.5, Noldus) was used to assess deficits in normal gait in the control, hyperhomocysteinemic and NVP-AAM077 treated hyperhomocysteinemic rats as described earlier (Parkkinen et a., 2013, *Stroke Res Treat* 2013: 410972; Wang et al., 2008, *J Cereb Blood Flow Metab* 28:1936-50). Briefly, rats were trained to walk on a glass platform or walkway (1.3 m long and 90 mm wide) with a fluorescent light reflected internally in the glass floor as the rats cross the walkway, scattering at points where the paws touch the glass. A camera was positioned 56 cm below the walkway with intensity threshold set to 0.15, camera gain set to 17 and the maximum allowed speed variation set to 60%. Pixels below the light intensity of 16 units on a 0-255 arbitrary scale were filtered out. A trial was regarded as successful if the animal did not have a maximum speed variation greater than 60% or did not stop on the runway. If an animal failed to complete a trial within 10 sec, walked backwards, or reared during the run, an additional re-run was performed. The camera recorded three such complete or successful runs across the walkway and the average of the three runs is reported. An experienced observer, blinded to the experimental group, labeled each paw on the recorded video and paw-related parameters were analyzed. The steps were automatically labeled as right forepaw (RF), right hind paw (RH), left forepaw (LF), and left hind paw (LH), where the right represents the non-impaired side and the left represents the impaired or affected side. Faulty labels caused by tail, whiskers, or genitalia were corrected. Automated analysis of wide range of parameters was performed: (A) The maximal contact area (expressed in $mm^2$), which is the paw area contacted at the moment of maximal paw-floor contact during stance was measured; (B) The print area (expressed in $mm^2$), which is the total floor area contacted by the paw during the stance phase was measured; (C) The print position (expressed in cm), which is the space relationship or distance between the former fore paw position to the consecutive hind paw position of the same side during one crossing of the walkway was evaluated. One control rat and one hyperhomocyteinemic rat were excluded from the study as they paused repeatedly during the run.

Cylinder test: Control, hyperhomocysteinemic and NVP-AAM077 treated hyperhomocysteinemic rats were subjected to cylinder test to assess the post-stroke asymmetry in fore-limb use (Balkaya, 2013, *J Cereb Blood Flow Metab* 33:330-338). The rats were placed individually inside a transparent plexiglass cylinder (diameter 20 cm, height 45 cm). A vertical exploration movement with either the left or right forelimb along the wall was scored as contact of each paw with the glass wall for a total period of 2 minutes. Simultaneous contact by both paws was scored separately. Two trials (10 min rest between trials) were recorded and the percentage use of the affected fore limb was calculated (Liu et al., 2013, *Behav Brain Res* 257:166-177; Schaar et al., 2010, *Exp Transl Stroke Med* 2:13). Six control rats and one hyperhomocysteinemic rat were excluded from the study, as they did not participate in the vertical exploration of the cylinder.

Accelerated Rotarod test: Control, hyperhomocysteinemic and NVP-AAM077 treated hyperhomocysteinemic rats were subjected to the accelerated Rotarod test to evaluate impairment of motor co-ordination and balance following stroke (Bouet et al., 2007, *Exp Neurol* 203:555-567; Schaar et al., 2010, *Exp Transl Stroke Med* 2:13). Rats were placed on a rotating cylindrical rod accelerating from 0 to 50 rpm for a period of 180 seconds, and their latency to fall was recorded. The mean of four runs (10 min rest between trials) was used for statistical analysis. One hyperhomocysteinemic rat was excluded from the study as the rat jumped off the rod repeatedly.

Adhesive removal test: Sensorimotor deficits following stroke was assessed by performing the adhesive removal test in control, hyperhomocysteinemic and NVP-AAM077 treated hyperhomocysteinemic rats. A small adhesive patch (7 mm×3 mm) was applied to the contralateral forepaw of each rat with equal pressure and the time taken to notice the presence of the patch (time to contact) and to remove it (time to remove) was recorded (Bouet et al., 2009, *Nat Protoc* 4:1560-1564). The time taken to notice the patch was recorded from the moment of placing the patch until the paw was shaken or touched by mouth. The time taken to remove the patch was recorded from the moment the mouth touched the paw to the time the patch was removed. The trial ended after the adhesive patch was removed or a maximum latency of three minutes. The mean of three trials (10-minute rest between tests) was used for statistical analysis.

Cresyl violet staining: On day 14 following MCAO, control, hyperhomocysteinemic and NVP-AAM077 treated hyperhomocysteinemic rats were anesthetized with isoflurane and perfused intracardialy with 4% paraformaldehyde in 0.01 M phosphate buffered saline pH 7.2 (PBS). Brains were removed, cryoprotected in 30% sucrose in PBS, and then frozen in Optimal Cutting Temperature compound (OCT) kept in dry ice. Cresyl Violet Acetate staining was performed on 12 µm cryosections. The fat was removed from the sections by immersing them in ethanol followed by chloroform. The sections were then re-hydrated by sequential exposure to decreasing concentrations of ethanol (100%, 95%, 70% and 0%) followed by staining with Cresyl Violet Acetate solution (5% Cresyl Violet acetate in glacial acetic acid-sodium acetate buffer, pH 3.7) for eight minutes. The sections were differentiated in 0.1% glacial acetic acid in 70% ethanol for 30 seconds followed by sequential dehydration in 95% and 100% ethanol and clearing with xylene. Finally, the sections were mounted with Cytoseal (DPX) and Multi Area Time Lapse images were obtained for the whole section using an Olympus microscope (10× objective).

Experimental design and statistical analysis: Data involving multiple groups were analyzed using one-way analysis of variance (ANOVA) and where assessment was performed across multiple days, the data was analyzed using repeated measure ANOVA (SPSS 24.0 software). Post-hoc analysis was done by Bonferroni's or Newman-Keuls multiple comparison tests. Vehicle vs. hyperhomocysteinemic groups or hyperhomocysteinemic vs. NVP-AAM077 treated hyperhomocysteinemic groups were considered as between group factor and days post-stroke as repeated factor. Analysis of two-group comparison was done using the Student's t-test. Data in the text and figures are expressed as means±SEM and differences were considered statistically significant when $p<0.05$. Pearson's r was used for effect size calculation for all t-test data (Mukaka, 2012, *Malawi Med J* 24:69-71).

Power calculations were run using G* power (3.1.9.2). For the one-way ANOVA, using an effect size of 0.60, an alpha of 0.05 and n=13 per treatment group produced 83% power. A sensitivity test using a one-way ANOVA with n=13 and a power of 80% at an alpha level of 0.05 indicates a sufficient sample size to detect an effect size of 0.57 and for the repeated measure ANOVA an effect size of 0.256 is detected with 80% power. Achieved power for the repeated measures ANOVA (2 between and 3 repeated measures) with an effect size of 0.7, an alpha of 0.05, and n=12 per treatment group produced a power of 99%. For the lowest significant t-test the effect size was 0.507, the calculated power was determined to be 0.76% with the given sample sizes n=10 for vehicle and n=12 for hyperhomocysteinemia. Thus, there is sufficient power in the data set to justify the conclusions.

Neuron Culture, L-Homocysteine Preparation and Stimulation

Primary cortical neuronal cultures were established from embryos obtained from pregnant Sprague Dawley female rats (16-17 day gestation) as previously described (Podder and Paul, 2009, *J Neurochem* 110:1095-1106; Poddar and Paul, 2013, *J Neurochem* 124: 558-570). Primary cortical neuronal cultures were also developed from pregnant wild-type or GluN2A-knockout mice (15-16 day gestation) using similar protocols. The cells were maintained in culture for 12-14 days prior to treatment with homocysteine. L-homocysteine (200 mM stock) was prepared by alkali hydrolysis of L-homocysteine thiolactone hydrochloride followed by neutralization with 2N HCL and maintained in 0.02 mM N-Tris(hydroxymethyl)methyl-2-aminoethanesulfonicd acid (TES) buffer pH 7.4 (Poddar et al., 2001, *Circulation* 103:2717-2723). For receptor stimulation neurons were treated with freshly prepared 50 µM of L-homocysteine in Hank's balanced salt solution (Podder and Paul, 2009, *J Neurochem* 110:1095-1106; Poddar and Paul, 2013, *J Neurochem* 124: 558-570) containing 50 µM of glycine (Lipton et al., 1997, *Proc Natl Acad Sci USA* 94:5923-5928). In a subset of culture plates, pharmacological inhibitors (NVP-AAM007) were added 10 minutes prior to homocysteine addition and maintained during homocysteine treatment. Cells were processed for immunoblotting or Hoechst DNA staining.

Immunoblotting

Equal protein from total cell lysates obtained from rat and mice neuronal cultures were resolved in 7.5% SDS-PAGE, and subjected to immunoblotting procedure as described earlier (Podder and Paul, 2009, *J Neurochem* 110:1095-1106). Blots were analyzed with antibodies as described in each experiment. All primary antibodies (anti-pERK, anti-ERK) and secondary-horse radish peroxidase conjugated antibody concentrations were used according to recommendations provided by the manufacturer. Signals from immune complexes in the blots were developed using West Pico supersignal chemiluminescence reagents and then captured on X-ray films. Densitometric analysis of the images was performed using the Image J software.

Hoechst DNA Staining

Neurons were subjected to staining with Hoechst 33342 dye for 15 minutes, washed extensively with PBS, and analyzed using fluorescent microscopy to assess nuclear damage. Imaging was performed with a Zeiss Axiovert 200M fluorescence microscope with attached AxioCam CCD camera using 20× objective lens (Carl Zeiss, Thomwood, N.Y.). To quantitatively assess the percentage of pyknotic nuclei a total of 1000 cells were counted for each set of experiments. Mean±SEM (n=3) were used for statistical comparison using ANOVA (Bonferroni's multiple comparison test). Differences were considered significant when $p<0.05$.

Oxygen Glucose Deprivation (OGD)

For OGD challenge, neurons were placed in an anaerobic chamber (Coy Laboratory Products, Inc., Grass Lake, Mich.) and incubated in balanced salt solution (116 mM NaCl, 5.4 mM KCl, 1 mM $NaH_2PO_4$, 1.8 mM $CaCl_2$, 26.2 mM $NaHCO_3$, 5 mM HEPES, 0.01 mM glycine, pH 7.4) lacking glucose and aerated with an anaerobic gas mixture (95:5% of $N_2:CO_2$ mixture) to remove residual oxygen. At specified time periods (one hour, two hours, and three hours) during OGD alone or OGD in the presence of L-Hcy (50 µM), cells were removed from the chamber and lysed for immunoblot analysis. Some cultures were treated with L-Hcy (three hours) during the OGD insult in the presence or absence of NVP-AAM077 (30 nM; 3 h). In some experiments after a two-hour insult (OGD alone or OGD+LHcy), the OGD medium was replaced with the original medium and then incubated for an additional 24 hours in a humidified atmosphere (95:5% of air/CO2 mixture). Cells were then subjected to staining with Hoechst 33342 dye for 15 minutes, washed extensively with PBS, and analyzed using fluorescent microscopy to assess nuclear damage. To quantitatively assess the percentage of pyknotic nuclei, a total of 1000 cells were counted for each set of experiments (Poddar et al., 2010, *J Neurochem* 115, 1350-1362).

Example 2

Materials and Reagents

Female Sprague-Dawley pregnant rats (gestation day 15; Envigo Corp., Huntingdon, United Kingdom) were used to establish primary neuron cultures. Institutional Animal Care and Use Committee of University of New Mexico, Health Sciences Center approved all animal procedures used in the current study. Reagents used for primary neuron cultures were obtained from Life Technologies (Carlsbad, Calif.). L-homocysteine thiolactone, cytosine D-arabinofuranoside, glycine and Hoechst 33342 were purchased from Sigma-Aldrich (St. Louis, Mo.). Anti-COX2 polyclonal antibody was obtained from Abeam (Canbridge, United Kingdom), anti-B-tubulin monoclonal antibody was obtained from Sigma-Aldrich (St. Louis, Mo.), and anti-rabbit and anti-mouse horse-radish-peroxidase conjugated secondary antibodies were obtained from Cell Signaling Technology (Beverly, Mass.). Bicinchoninic acid (BCA) protein estimation kit and West Pico supersignal chemiluminescence reagents for immunoblotting were purchased from Pierce (Rockland, Ill.). Selective pharmacological inhibitors were obtained as follows: MK801 hydrogen maleate from Sigma-Aldrich (St. Louis, Mo.), 1-Napthyl acetyl spermine trihydrochloride (NASPM) from Tocris, (Bristol, United Kingdom), D-(−)-2-Amino-5-phosphopentanoic acid (D-AP5), PD98059, SB203580, bengamide, and NVP-AAM007 were obtained from EMD biosciences (Billerica, Mass.). CAY100404 was purchased from Cayman Chemicals (Ann Arbor, Mich.). PGE2 enzyme immunoassay kit was purchased from Arbor assay (Ann Arbor, Mich.), and cPLA2 activity assay kit was obtained from Cayman chemicals (Ann Arbor, Mich.).

Neuron Culture, L-Homocysteine Preparation and Stimulation

Primary cortical neuronal cultures were established from embryos obtained from pregnant Sprague Dawley female rats (16-17 day gestation) as described earlier (Poddar and Paul, 2009, *J Neurochem* 110:1095-1106; Poddar and Paul, 2013, *J Neurochem* 124:558-570). Primary cortical neuronal cultures were also developed from pregnant wildtype or GluN2A-knockout mice (15-16 day gestation) using similar protocols. The cells were maintained in culture for 12-14 days prior to treatment with homocysteine. L-homocysteine (200 mM stock) was prepared by alkali hydrolysis of L-homocysteine thiolactone hydrochloride followed by neutralization with 2N HCl and maintained in 0.02 mM N-Tris (hydroxymethyl)methyl-2-aminoethanesulfonicd acid (TES) buffer pH 7.4 (Poddar et al., 2001, *Circulation* 103:2717-2723). For receptor stimulation neurons were treated with freshly prepared 50 µM of L-homocysteine in Hank's balanced salt solution (Poddar and Paul, 2009, *J Neurochem* 110:1095-1106; Poddar and Paul, 2013, *J Neurochem* 124:558-570) containing 50 µM of glycine (Lipton et al., 1997, *Proc Natl Acad Sci USA* 94:5923-5928). In a subset of culture plates, pharmacological inhibitors (D-AP5, MK801, NVP-AAM007, PD98059, SB203580, or bengamide) were added 10 min prior to homocysteine addition and maintained during homocysteine treatment. Cells were washed with buffer (PBS, pH 7.4, containing sodium pyrophosphate and sodium vanadate as phosphatase inhibitor), lysed in SDS Laemmli buffer and analyzed for immunoblotting.

Immunoblotting

Equal protein from total cell lysates obtained from rat and mice neuronal cultures were resolved in 7.5% SDS-PAGE, and subjected to immunoblotting procedure as described earlier (Poddar and Paul, 2009, *J Neurochem* 110:1095-1106). Blots were analyzed with antibodies as described in each experiment. All primary antibodies (anti-COX2, anti-B-tubulin) and secondary-horse radish peroxidase conjugated antibody concentrations were used according to recommendations provided by the manufacturer. Signals from immune complexes in the blots were developed using West Pico supersignal chemiluminescence reagents and then captured on X-ray films. Densitometric analysis of the images was performed using the Image J software.

Measurement of PGE2 Levels and cPLA2 Activity

Neuron cultures were treated with or without L-homocysteine in the presence or absence of pharmacological inhibitors for the time period specified in each experiment. The medium was collected from each experimental plate and centrifuged at 1000 rpm for five minutes to remove cellular debris. Equal amounts (100 µl) of the supernatant from each sample were used to determine the amount of PGE2 using the PGE2 enzyme immunoassay kit according to the manufacturer's instructions. For measurement of cPLA2 activity, the neuronal cells from the above treated conditions were harvested in ice-cold Tris-buffered saline (pH7.4) containing sodium pyrophosphate as phosphatase inhibitor, sonicated three times with five-second bursts and two minutes on ice between intervals. The lysed cell suspensions were centrifuged at 10,000 rpm for 10 minutes and the supernatant removed. Equal amounts of protein from the supernatant (assessed using BCA protein estimation kit) were estimated for activity of cPLA2 using cPLA2 activity assay kit according to the manufacturer's protocol.

Statistical Analysis

Statistical analysis and comparison was performed using One-way analysis of variance (ANOVA, Bonferroni's multiple comparison test) and differences were considered significant when $p<0.05$.

Example 3

Animals

Female Sprague-Dawley pregnant rats (RRTD: RGD_737903) were purchased from Envigo (Livermore, Calif.) for establishing primary neuron cultures. GluN2A NMDAR Knockout (GluN2A-KO) mice were obtained from Dr. Andrew Holmes, NIH/NIAAA (Sakimura et al., 1995, *Nature* 373:151-155; Brigman et al., 2008, *Learn Mem* 15:50-54), and bred at the animal facility of University of New Mexico. No custom made materials were generated using these mice for this study. Adult mice were bred in humidity and temperature controlled environment (20±1° C.) under standard cage density conditions with one female and one male per cage. The animals had access to food and water ad libitum. Each animal was genotyped (Sakimura et al., 1995, *Nature* 373:151-155; Brigman et al., 2008, *Learn Mem* 15:50-54) and wild type (WT) male and female mice as well as GluN2A-KO male and female mice were mated to generate timed pregnant female mice. The males were removed from the females after a 24-hour period, which was considered gestational day 1. Pregnancy was verified by the presence of vaginal plugs and/or weight gain.

Materials and Reagents

Reagents used for establishing primary neuronal cultures (Dulbecco's Modified Eagle's Medium, DMEM; Modified Eagle's Medium, MEM; Fetal bovine serum; Hanks Balanced Salt solution; antibiotic/antimycotic mixture; cytosine arabinoside) were obtained from Invitrogen, Thermo Fisher Scientific (Waltham, Mass.). L-homocysteine thiolactone, cytosine D-arabinofuranoside, N-Tris(hydroxymethyl)methyl-2-aminoethanesulfonicd acid (TES), glycine, and Hoechst 33342 were purchased from MilliporeSigma (Burlington, Mass.). Anti-COX2 polyclonal antibody (RRID: AB_2085144) was obtained from Abcam (Cambridge, United Kingdom), anti β-tubulin monoclonal antibody (RRID:AB_2241191) was obtained from Santa Cruz Biotechnology (Dallas, Tex.), and anti-rabbit (RRID: AB_2099233) and anti-mouse (RRID:AB_330924) horseradish-peroxidase conjugated secondary antibodies were obtained from Cell Signaling Technology (Beverly, Mass.). Bicinchoninic acid (BCA) protein estimation kit and West Pico supersignal chemiluminescence reagent were purchased from Pierce (Rockland, Ill.). Selective pharmacological inhibitors were obtained as follows: DL-2-Amino-5-phosphopentanoic acid (DL-AP5), MK-801 hydrogen maleate (MK801), PD98059, SB203580, Bengamide B and NVP-AAM077 were obtained from Millipore Sigma (St. Louis, Mo.). CAY10404 was purchased from Cayman Chemicals (Ann Arbor, Mich.). PGE2 enzyme-linked immunosorbent assay (ELISA) kit was purchased from Arbor assays (Ann Arbor, Mich.) and cPLA2 activity assay kit was obtained from Cayman chemicals (Ann Arbor, Mich.).

Neuron Culture, L-Homocysteine Preparation, and Stimulation

Embryos obtained from pregnant female Sprague Dawley rats (16-17 day gestation) or WT and GluN2A KO mice (15-16 day gestation) were used to establish primary neuronal cultures, as previously described (Poddar and Paul, 2009, *J Neurochem* 110:1095-1106; Poddar and Paul, 2013, *J Neurochem* 124:558-570). The pregnant females were sacrificed using inhaled $CO_2$ and death was confirmed by absence of heartbeat. Embryos were removed post-mortem and the cortex was dissected out. A single-cell suspension was made using fire-polished pasture pipettes, plated on poly-D-lysine coated 60 mm culture dishes (BD BioCoat plates; Thermo Fisher Scientific, Waltham, Mass.) for seven minutes. Following removal of non-adhering cells, the neurons were grown in DMEM supplemented with 5% fetal bovine serum and antibiotic/antimycotic mixture for three days, following which they were treated with 1 µM cytosine arabinoside at DIV 3 for 24 hours to prevent glial expansion. The cultures were thereafter maintained in culture MEM containing 5% fetal bovine serum and antibiotic/antimycotic mixture for 12-14 days prior to treatment with L-homocysteine.

L-homocysteine (200 mM stock) was prepared by alkali hydrolysis of L-homocysteine thiolactone hydrochloride followed by neutralization with 2N HCL and maintained in 0.02 mM of TES buffer pH 7.4 (Poddar et al. 2001, *Circulation*, 103:2717-2723). For receptor stimulation neurons were treated with freshly prepared 50 µM of L-homocysteine in Hank's balanced salt solution (Poddar and Paul, 2009, *J Neurochem* 110:1095-1106; Poddar and Paul, 2013, *J Neurochem* 124:558-570; Poddar et al., 2017, *J Neurochem* 142:560-573) containing 50 µM of glycine (Lipton et al., 1997, *Proceedings of the National Academy of Sciences of the United States of America* 94:5923-5928). The concentration of L-homocysteine used for all experiments in this study was based on a dose response study demonstrating that 50 µM of homocysteine has a detrimental effect on neurons (Poddar and Paul, 2009, *J Neurochem* 110:1095-1106). In a subset of experiments pharmacological inhibitors (MK801, NVP-AAM007, PD98059, SB203580, Bengamide or CAY10404) were added 10 minutes prior to treatment with L-homocysteine. Cells were processed for either immunoblotting or cPLA2 activity assay. The culture media were processed for measurement of PGE2 levels.

Immunoblotting

Rat and mice neuronal cultures were washed with PBS (pH 7.4), containing sodium pyrophosphate and sodium vanadate as phosphatase inhibitors, and harvested in SDS sample buffer (Laemmli, 1970, *Nature* 227:680-685). Equal protein from total cell lysates, estimated using BCA kit, was resolved by SDS-PAGE (7.5%) followed by western blotting on PVDF membranes. Immunoblot analysis was performed by first blocking with 5% non-fat dry milk for 1 h at room temperature followed by incubation with either COX2 immunoblot analysis (Poddar and Paul, 2009, *J Neurochem* 110:1095-1106) as described in each experiment. All primary antibodies and horseradish peroxidase conjugated secondary antibodies were used according to manufacturer's recommendations. Signals from immune complexes in the blots were developed using West Pico supersignal chemiluminescence reagents and then captured on X-ray films. Densitometric analysis of the images was performed using the NIH Image J software.

Measurement of cPLA2 Activity, MCP-1 Levels, and PGE2 Levels in Neuron Cultures

For measurement of cPLA2 activity and MCP-1 levels in cell lysates, neuronal lysates were prepared by harvesting neurons in ice-cold Tris-buffered saline (pH 7.4) containing phosphatase inhibitor, sonicated three times in five-second bursts and placed on ice (two minutes) between each burst of sonication. The lysed cell suspensions were centrifuged at 10,000 rpm (10 minutes) and the supernatant was collected in another tube. Equal amounts of protein from the supernatant were processed for cPLA2 activity assay according to the manufacturer's protocol. Equal protein from the lysates were also used to estimate MCP-1 levels using an MCP-1 ELISA kit.

For measurement of PGE2 levels and MCP-1 levels released from neurons, culture medium was collected from each experimental plate and centrifuged at 1000 rpm for five minutes to remove cellular debris. Equal volume (100 µl) of the supernatant from each sample was used to determine PGE2 level using the PGE2 ELISA kit according to the manufacturer's instructions.

Measurement of PGE2 and MCP-1 Levels in Ischemic Brain

Wistar rats were made hyperhomocysteinemic using osmotic pump containing L-homocysteine. Animals were hyperhomocysteinemic (19-23 µM) within three days of pump implantation. Ischemic stroke was induced by MCAO for 60 minutes followed by reperfusion for six hours. Tissue punches from the ipsilateral striatum and cortex were lysed in ice-cold Phosphate buffered saline (pH 7.4) containing phosphatase inhibitor, sonicated three times in five-second bursts and placed on ice (two minutes) between each burst of sonication. The lysed cell suspensions were centrifuged at 10,000 rpm (10 minutes) and the supernatant was collected in another tube. Equal amounts of protein from the supernatant were processed for PGE2 and MCP-1 levels using respective ELISA kit.

Statistical Analysis

Statistical analysis and comparison was performed using GraphPad Prism (version 5a) software. One-way analysis of variance (ANOVA, Bonferroni's multiple comparison test) were analyzed and differences were considered significant when $p<0.05$. Assessment of data normality and test for determining outliers were not performed for the datasets.

Example 4

Materials and Reagents

Pregnant female Sprague-Dawley rats were purchased from Envigo (Livermore, Calif.). GluN2A KO mice were obtained from Dr. Andrew Holmes, NIH/NIAAA (Sakimura et al., 1995, *Nature* 373:151-155) and time pregnant mice were generated at the animal facility of University of New Mexico. The Institutional Animal Care and Use Committee of University of New Mexico, HSC approved all animal procedures. L-homocysteine thiolactone, glycine, EGTA and Hoechst 33342 were purchased from Sigma-Aldrich (St. Louis, Mo.). Fura2 acetooxymethyl ester (Fura2-AM) and all cell culture reagents were purchased from Invitrogen (Thermo Fisher Scientific, Carlsbad, Calif.). Anti-phospho-ERK1/2 (Thr202/Tyr204) mAb (pERK), anti-rabbit and anti-mouse horseradish peroxidase-conjugated secondary antibodies were purchased from Cell Signaling Technology (Danvers, Mass.). Anti-ERK2 (ERK) and anti-β-tubulin polyclonal antibodies were purchased from SantaCruz Biotechnology (Dallas, Tex.). Anti-GluN2A rabbit monoclonal antibody was purchased from Abeam (Cambridge, United Kingdom). Anti-GluN1 monoclonal antibody and anti-GluN2B polyclonal antibody were purchased from MilliporeSigma (Burlington, Mass.). Ionomycin, DL-AP5 (DL-2-Amino-5-phosphopentanoic acid), Ro 25-6981, PD98059, NVP-AAM077 ([(R)-[(S)-1-(4-bromo-phenyl)-ethyl-amino]-(2,3-dioxo-1,2,3,4-tetrahydro-quinoxalin-5-yl)-methyl]phosphonic acid) were obtained from EMD Biosciences, Inc. (San Diego, Calif.).

Neuron Culture, L-Homocysteine Preparation and Stimulation

Embryos obtained from pregnant Sprague Dawley rats (16-17-day gestation) or wild type (WT) and GluN2A KO mice (15-16-day gestation) were used to establish primary cortical neuronal cultures as previously described (Poddar and Paul, 2009, *J Neurochem* 110:1095-1106; Poddar and Paul, 2013, *J Neurochem* 124:558-570; Poddar et al., 2017, *J Neurochem* 142:560-573). Neurons were grown on either (a) 35-mm culture dishes (MatTek Corp., Ashland, Mass.)

coated overnight with poly-D-lysine (50 µg/ml) and laminin (10 µg/ml) for $Ca^{2+}$ imaging studies, (b) poly-D-lysine-coated 60 mm dishes (Corning BIOCOAT, Corning Inc., Corning, N.Y.) for biochemical studies, or (c) poly-D-lysine-coated 4-well culture slides (Corning BIOCOAT, Corning Inc., Corning, N.Y.) for cell death assay. Neurons were maintained in culture for 12-13 days before experiment. The cells were treated with freshly prepared L-homocysteine (50 µM) in Hank's balanced salt solution containing 50 µM of glycine (Lipton et al., 1997, *Proceedings of the National Academy of Sciences of the United States of America* 94:5923-5928; Poddar and Paul, 2009, *J Neurochem* 110: 1095-1106; Poddar and Paul, 2013, *J Neurochem* 124:558-570; Poddar et al., 2017, *J Neurochem* 142:560-573) for the specified time periods. In a parallel series of experiments, cells were treated with glutamate (50 µM) for the specified time periods. Cells were then processed for live cell imaging, immunoblotting or cell death assay. In some experiments EGTA, DL-AP5, NVP-AAM077, Ro 25-6981 or PD98059 was added 15 minutes prior to L-homocysteine or glutamate treatment.

Calcium Measurements $[Ca^{2+}]_i$ in neurons was determined using the fluorescent indicator, Fura2-AM. Briefly, neurons were loaded with Fura2 (10 µM) in phenol red free Hank's balanced salt solution for 30 minutes at 37° C. followed by post-incubation for 20 minutes (Paul, S. and Connor, J. A., 2010, *J Neurochem* 114:1107-1118). Time lapse live cell imaging was performed following stimulation using a Nikon Ti Eclipse inverted microscope equipped with Tokai Hit stage top incubator maintained at 37° C. and infused with 95:5% air:$CO_2$ mixture. Fields of 5-8 cells were imaged using a 40× oil immersion objective (Nikon). Fluorescence excitations (340 and 380 nm) were provided with Sutter LB-LS/30 Lambda xenon arc lamp and fluorescence emissions (510 nm) were captured using a CCD camera (Teledyne Photometries, Tucson, Ariz.). NIS Elements AR software was used for data acquisition and analysis. Ratiometric data (340/380 nm) from regions of interest were corrected for background and converted into estimates of $[Ca^{2+}]_i$. as described previously (Paul, S. and Connor, J. A., 2010, *J Neurochem* 114:1107-1118) using the equation developed earlier (Grynkiewicz et al., 1985, *J Biol Chem* 260:3440-3450). Maximum and minimum fluorescence ratios were determined from Fura2 loaded cells treated with ionomycin (5 µM) in calcium containing medium (2 mM) or in calcium free media with EGTA (0.5 mM).

Immunoblotting

Rat and mice neuron cultures were harvested in SDS sample buffer (Laemmli, 1970, *Nature* 227:680-685). Equal protein from the cell lysates were resolved by SDS-PAGE (7.5%) and subjected to immunoblotting procedures as previously described (Poddar and Paul, 2009, *J Neurochem* 110:1095-1106; Poddar and Paul, 2013, *J Neurochem* 124: 558-570; Poddar et al., 2017, *J Neurochem* 142:560-573; Paul et al., 2003, *Nature Neuroscience* 6:34-42). The blots were analyzed with the specified antibodies according to the manufacturer's protocol. Densitometric analyses of the images captured on x-ray films were performed using the Image J software.

Hoechst DNA-Staining

Cortical neuron cultures from rat and mice were treated either with L-homocysteine for 18 hours or glutamate for one hour. Glutamate treated cells were then maintained in their original medium for another 17 hours. For some experiments, neurons were treated with L-homocysteine or glutamate in the presence of NVP-AAM077 or PD98059. The neurons were then fixed and stained with Hoechst 33342 dye as previously described (Poddar and Paul, 2009, *J Neurochem* 110:1095-1106). Percentage of pyknotic nuclei was quantitatively assessed by fluorescent microscopy to determine the extent of neuronal death.

Statistical Analysis

Statistical analysis and comparison was performed using One-way analysis of variance (ANOVA, Newman-Keuls multiple comparison test) and differences were considered significant when $p<0.05$.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure (s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for treating a hyperhomocysteinemic subject having cerebral ischemic stroke, the method comprising:
administering to a hyperhomocysteinemic subject following cerebral stroke a composition that includes an inhibitor or an antagonist of a GluN2A-containing N-methyl-D-aspartate receptor (NMDAR) in an amount effective to ameliorate at least one symptom or clinical sign of cerebral stroke.

2. The method of claim 1, wherein the inhibitor of GluN2A-NMDAR comprises NVP-AAM077.

3. The method of claim 1, wherein the antagonist of GluN2A-NMDAR comprises {(S)-5-[(R)-2-amino-2-carboxyethyl]-1-[4-(3-fluoropropyl) phenyl]-4,5-dihydro-1H-pyrazole-3-carboxylic acid} (ST3), {(S)-5-[(R)-2-amino-2-carboxyethyl]-1-(4-fluorophenyl)-4,5-dihydro-1H-pyrazole-3-carboxylic acid} (ST1), {(S)-5-[(R)-2-amino-2- carboxyethyl]-1-(4-bromophenyl)-4,5-dihydro-1H-pyrazole-3-carboxylic acid} (ST6), {(S)-5-[(R)-2-amino-2-carboxyethyl]-1-phenyl-4,5-dihydro-1H-pyrazole-3-carboxylic acid} (FRA-19), 3-chloro-4-fluoro-N-[(4-{[2-phenylcarbonyl)hydrazine]carbonyl}phenyl) methyl}benzenesulfonamide) (TCN-201), 5-(((3-chloro-4-fluorophenyl)sulfonamido)methyl)-N-((2-methylthiazol-5-yl)methyl)pyrazine-2-carboxamide (MPX-004), 5-(((3,4-difluorophenyl)sulfonamido)methyl)-6-methyl-N-((2-methylthiazol-5-yl)methyl)pyrazine-2-carboxamide (MPX-007), or a derivative of TCN-201.

4. A method for treating a hyperhomocysteinemic subject having a neurological disorder exacerbated by homocysteine-induced neuroinflammation, the method comprising:
administering to a hyperhomocysteinemic subject a composition that includes an inhibitor or an antagonist of a GluN2A-containing N-methyl-D-aspartate receptor (NMDAR) in an amount effective to decrease neuroinflammation.

5. The method of claim 4, wherein the neurological disorder comprises ischemic stroke, traumatic brain injury, vascular dementia, mild cognitive impairment, or Alzheimer's Disease.

6. The method of claim 4, wherein the inhibitor of GluN2A-NMDAR comprises NVP-AAM077.

7. The method of claim 4, wherein the antagonist of GluN2A-NMDAR comprises {(S)-5-[(R)-2-amino-2-carboxyethyl]-1-[4-(3-fluoropropyl) phenyl]-4,5-dihydro-1H-pyrazole-3-carboxylic acid} (ST3), {(S)-5-[(R)-2-amino-2-carboxyethyl]-1-(4-fluorophenyl)-4,5-dihydro-1H-pyrazole-3-carboxylic acid} (ST1), {(S)-5-[(R)-2-amino-2-carboxyethyl]-1-(4-bromophenyl)-4,5-dihydro-1H-pyrazole-3-carboxylic acid}(ST6), {(S)-5-[(R)-2-amino-2-carboxyethyl]-1-phenyl-4,5-dihydro-1H-pyrazole-3-carboxylic acid} (FRA-19), 3-chloro-4-fluoro-N-[(4-{[2-phenylcarbonyl)hydrazine]carbonyl}phenyl) methyl}benzenesulfonamide) (TCN-201), 5-(((3-chloro-4-fluorophenyl)sulfonamido)methyl)-N-((2-methylthiazol-5-yl)methyl)pyrazine-2-carboxamide (MPX-004), 5-(((3,4-difluorophenyl)sulfonamido)methyl)-6-methyl-N-((2-methylthiazol-5-yl)methyl)pyrazine-2-carboxamide (MPX-007), or a derivative of TCN-201.

8. The method of claim 4, wherein the neuroinflammation is mediated by prostaglandin E2 (PGE2).

\* \* \* \* \*